US011293029B2

(12) United States Patent
Serber et al.

(10) Patent No.: US 11,293,029 B2
(45) Date of Patent: *Apr. 5, 2022

(54) PROMOTERS FROM *CORYNEBACTERIUM GLUTAMICUM*

(71) Applicant: ZYMERGEN INC., Emeryville, CA (US)

(72) Inventors: Zachariah Serber, Sausalito, CA (US); Katherine G. Gora, Oakland, CA (US); Shawn P. Manchester, Oakland, CA (US)

(73) Assignee: Zymergen Inc., Emeryville, CA (US)

( * ) Notice: Subject to any disclaimer, the term of this patent is extended or adjusted under 35 U.S.C. 154(b) by 544 days.

This patent is subject to a terminal disclaimer.

(21) Appl. No.: 16/060,375

(22) PCT Filed: Dec. 7, 2016

(86) PCT No.: PCT/US2016/065464
§ 371 (c)(1),
(2) Date: Jun. 7, 2018

(87) PCT Pub. No.: WO2017/100376
PCT Pub. Date: Jun. 15, 2017

(65) Prior Publication Data
US 2018/0362991 A1 Dec. 20, 2018

Related U.S. Application Data

(60) Provisional application No. 62/431,409, filed on Dec. 7, 2016, provisional application No. 62/264,232, filed on Dec. 7, 2015.

(51) Int. Cl.
*C12N 15/77* (2006.01)
*C12N 15/113* (2010.01)
*C12P 13/08* (2006.01)

(52) U.S. Cl.
CPC ............ *C12N 15/77* (2013.01); *C12N 15/113* (2013.01); *C12P 13/08* (2013.01)

(58) Field of Classification Search
CPC .................................................. C12N 15/77
See application file for complete search history.

(56) References Cited

U.S. PATENT DOCUMENTS

| 4,435,504 | A | 3/1984 | Zuk et al. |
| 4,489,160 | A | 12/1984 | Katsumata et al. |
| 4,601,893 | A | 7/1986 | Cardinal |
| 4,855,240 | A | 8/1989 | Rosenstein et al. |
| 4,980,298 | A | 12/1990 | Blake et al. |
| 5,158,891 | A | 10/1992 | Takeda et al. |
| 5,275,940 | A | 1/1994 | Kino et al. |
| 5,487,993 | A | 1/1996 | Herrnstadt et al. |
| 5,516,670 | A | 5/1996 | Kuehnle et al. |
| 5,591,645 | A | 1/1997 | Rosenstein |
| 5,605,793 | A | 2/1997 | Stemmer |
| 5,753,477 | A | 5/1998 | Chan |
| 5,756,345 | A | 5/1998 | Camakaris et al. |
| 5,770,409 | A | 6/1998 | Pfefferle et al. |
| 5,811,238 | A | 9/1998 | Stemmer et al. |
| 5,827,698 | A | 10/1998 | Kikuchi et al. |
| 5,830,721 | A | 11/1998 | Stemmer et al. |
| 5,834,252 | A | 11/1998 | Stemmer et al. |
| 5,837,458 | A | 11/1998 | Minshull et al. |
| 5,928,905 | A | 7/1999 | Stemmer et al. |
| 5,990,350 | A | 11/1999 | Stevens et al. |
| 6,040,439 | A | 3/2000 | Hayakawa et al. |
| 6,060,296 | A | 5/2000 | Hoekstra |
| 6,090,592 | A | 7/2000 | Adams et al. |
| 6,117,679 | A | 9/2000 | Stemmer et al. |
| 6,136,565 | A | 10/2000 | Best et al. |
| 6,174,673 | B1 | 1/2001 | Short et al. |
| 6,251,674 | B1 | 6/2001 | Tobin et al. |
| 6,287,862 | B1 | 9/2001 | delCardayre et al. |
| 6,300,070 | B1 | 10/2001 | Boles et al. |
| 6,326,204 | B1 | 12/2001 | delCardayre et al. |
| 6,335,160 | B1 | 1/2002 | Paatten et al. |
| 6,335,198 | B1 | 1/2002 | delCardayre et al. |

(Continued)

FOREIGN PATENT DOCUMENTS

| CN | 101605890 A | 12/2009 |
| DE | 19548222 A1 | 6/1997 |

(Continued)

OTHER PUBLICATIONS

Rastegari et al: "Improvement in the production of L-lysine by overexpression of aspartokinase (ASK) in C. glutamicum ATCC 21799", 2013 Tropical Journal of Pharmaceutical Research 2013 Pharmacotherapy Group NGA, vol. 12, No. 1, pp. 51-56 (Year: 2013).*
Rytter et. al. Synthetic promoter libraries for Corynebacterium glutamicum. Appl Microbiol Biotechnol (2014) 98:2617-2623 (Year: 2014).*
Pfeifer et. al. 2013 Comprehensive analysis of the Corynebacterium glutamicum transcriptome . . . BMC Genomics 4:888 (Year: 2013).*
Lee et. al. 2013 Adaptive evolution of Corynebacterium glutamicum . . . Biotechnology Letters. (Year: 2013).*
Fazius et. al.Lysine biosynthesis in microbes: relevance as drug target and prospects for β-lactam antibiotics production. 2013. Appl Microbiol Biotechnol 97:3763-3772 (Year: 2013).*
GenBank: CP012194.1 Corynebacterium glutamicum strain CP18, complete genome (Year: 2015).*

(Continued)

*Primary Examiner* — Nancy J Leith
*Assistant Examiner* — Tiffany Nicole Grooms
(74) *Attorney, Agent, or Firm* — Cooley LLP

(57) ABSTRACT

Provided are native promoters comprising polynucleotides isolated from *Corynebacterium glutamicum*, and mutant promoters derived therefrom, which may be used to regulate, i.e., either increase or decrease, gene expression. Also provided are promoter ladders comprising a plurality of the promoters having incrementally increasing promoter activity. Also provided are host cells and recombinant vectors comprising the promoters, and methods of expressing genes of interest and producing biomolecules using the host cells.

20 Claims, 5 Drawing Sheets

Specification includes a Sequence Listing.

(56) References Cited

U.S. PATENT DOCUMENTS

| | | |
|---|---|---|
| 6,352,859 B1 | 3/2002 | delCardayre et al. |
| 6,358,709 B1 | 3/2002 | Short et al. |
| 6,379,964 B1 | 4/2002 | del Cardayre et al. |
| 6,479,258 B1 | 11/2002 | Short |
| 6,528,311 B1 | 3/2003 | delCardayre et al. |
| 6,586,214 B1 | 7/2003 | Dunican et al. |
| 6,605,449 B1 | 8/2003 | Short |
| 6,713,279 B1 | 3/2004 | Short |
| 6,716,631 B1 | 4/2004 | delCardayre et al. |
| 6,759,195 B1 | 7/2004 | Bentley et al. |
| 6,759,218 B2 | 7/2004 | Mockel et al. |
| 7,033,781 B1 | 4/2006 | Short |
| 7,115,400 B1 | 10/2006 | Adessi et al. |
| 7,118,904 B2 | 10/2006 | Mockel et al. |
| 7,127,379 B2 | 10/2006 | Palsson et al. |
| 7,138,266 B2 | 11/2006 | Debabov et al. |
| 7,148,054 B2 | 12/2006 | delCardayre et al. |
| 7,507,574 B2 | 3/2009 | Bill et al. |
| 7,510,854 B2 | 3/2009 | Pompejus et al. |
| 7,629,170 B2 | 12/2009 | delCardayre et al. |
| 7,711,490 B2 | 5/2010 | Maranas et al. |
| 7,826,975 B2 | 11/2010 | Maranas et al. |
| 7,842,485 B2 | 11/2010 | Gill et al. |
| 7,846,688 B2 | 12/2010 | Gill et al. |
| 7,987,056 B2 | 7/2011 | Gill et al. |
| 8,076,138 B2 | 12/2011 | delCardayre et al. |
| 8,108,152 B2 | 1/2012 | Maranas et al. |
| 8,110,360 B2 | 2/2012 | Serber et al. |
| 8,221,982 B2 | 7/2012 | Serber et al. |
| 8,332,160 B1 | 12/2012 | Platt et al. |
| 8,349,587 B2 | 1/2013 | Fischer et al. |
| 8,377,681 B2 | 2/2013 | delCardayre et al. |
| 8,467,975 B2 | 6/2013 | Gill et al. |
| 8,476,041 B2 | 7/2013 | Cervin et al. |
| 8,530,203 B2 | 9/2013 | Ikeda et al. |
| 8,546,136 B2 | 10/2013 | Serber et al. |
| 8,685,737 B2 | 4/2014 | Serber et al. |
| 8,697,359 B1 | 4/2014 | Zhang |
| 8,741,603 B2 | 6/2014 | Han et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,883,464 B2 | 11/2014 | Lynch et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,388,419 B2 | 7/2016 | Lynch et al. |
| 9,428,778 B2 | 8/2016 | Lynch et al. |
| 9,506,087 B2 | 11/2016 | Vroom et al. |
| 9,506,167 B2 | 11/2016 | Shetty et al. |
| 9,580,719 B2 | 2/2017 | Retallack et al. |
| 9,637,739 B2 | 5/2017 | Siksnys et al. |
| 9,677,090 B2 | 6/2017 | Donohue et al. |
| 9,688,972 B2 | 6/2017 | May et al. |
| 9,701,971 B2 | 7/2017 | Serber et al. |
| 9,738,687 B2 | 8/2017 | Guay et al. |
| 9,745,562 B2 | 8/2017 | Donohue et al. |
| 9,752,176 B2 | 9/2017 | Kung et al. |
| 9,771,795 B2 | 9/2017 | Knight et al. |
| 9,790,490 B2 | 10/2017 | Zhang et al. |
| 9,816,081 B1 | 11/2017 | Donohue et al. |
| 9,822,372 B2 | 11/2017 | Zhang et al. |
| 9,840,713 B2 | 12/2017 | Zhang |
| 9,902,980 B2 | 2/2018 | Fischer et al. |
| 9,988,624 B2 | 6/2018 | Serber et al. |
| 10,047,358 B1 | 8/2018 | Serber et al. |
| 10,544,390 B2 | 1/2020 | Manchester et al. |
| 2002/0169562 A1 | 11/2002 | Stephanopoulos et al. |
| 2002/0197605 A1 | 12/2002 | Nakagawa et al. |
| 2003/0027175 A1 | 2/2003 | Stephanopoulos et al. |
| 2004/0077090 A1 | 4/2004 | Short |
| 2004/0101963 A1 | 5/2004 | Bibb et al. |
| 2005/0054106 A1 | 3/2005 | Ow et al. |
| 2005/0124010 A1 | 6/2005 | Short et al. |
| 2005/0260707 A1 | 11/2005 | Pompejus et al. |
| 2006/0019301 A1 | 1/2006 | Hansen et al. |
| 2006/0084098 A1 | 4/2006 | Gill et al. |
| 2006/0269975 A1 | 11/2006 | Pompejus et al. |
| 2006/0286574 A1 | 12/2006 | Romesberg et al. |
| 2007/0166792 A1 | 1/2007 | Olson et al. |
| 2007/0042474 A1 | 2/2007 | Pompejus et al. |
| 2007/0059768 A1 | 3/2007 | Gill et al. |
| 2007/0118916 A1 | 5/2007 | Puzio et al. |
| 2007/0122890 A1 | 5/2007 | Park et al. |
| 2007/0218533 A1 | 9/2007 | Gill et al. |
| 2007/0274972 A1 | 11/2007 | Muller et al. |
| 2007/0292918 A1 | 12/2007 | Stelman et al. |
| 2008/0103060 A1 | 5/2008 | Gill et al. |
| 2008/0171371 A1* | 7/2008 | Yukawa ............... C12N 15/67 435/173.1 |
| 2008/0243397 A1 | 10/2008 | Peccoud et al. |
| 2008/0268502 A1* | 10/2008 | Haefner ............... C07K 14/34 435/69.1 |
| 2009/0029356 A1 | 1/2009 | Pompejus et al. |
| 2009/0221442 A1 | 9/2009 | Dower et al. |
| 2009/0253174 A1 | 10/2009 | Serber et al. |
| 2009/0280529 A1 | 11/2009 | Berg et al. |
| 2009/0325248 A1 | 12/2009 | Marx et al. |
| 2010/0048938 A1 | 2/2010 | Berg et al. |
| 2010/0105865 A1 | 4/2010 | Telford et al. |
| 2010/0124768 A1 | 5/2010 | Serber et al. |
| 2010/0136633 A1 | 6/2010 | Serber et al. |
| 2010/0137143 A1 | 6/2010 | Rothberg et al. |
| 2010/0210017 A1 | 8/2010 | Gill et al. |
| 2010/0216648 A1 | 8/2010 | Stabler et al. |
| 2010/0304982 A1 | 12/2010 | Hinz et al. |
| 2010/0317115 A1 | 12/2010 | Gill et al. |
| 2011/0054654 A1 | 3/2011 | Phillips et al. |
| 2011/0136688 A1 | 6/2011 | Scholl et al. |
| 2011/0172127 A1 | 7/2011 | Jacobsen et al. |
| 2011/0223638 A1 | 9/2011 | Wiedenheft et al. |
| 2011/0223671 A1 | 9/2011 | Yoder et al. |
| 2011/0244575 A1 | 10/2011 | Lipscomb et al. |
| 2011/0277179 A1 | 11/2011 | Puzio et al. |
| 2012/0070870 A1 | 3/2012 | Way et al. |
| 2012/0077681 A1 | 3/2012 | Gill et al. |
| 2012/0245056 A1 | 9/2012 | Serber et al. |
| 2012/0252681 A1 | 10/2012 | Del Cardayre et al. |
| 2012/0264902 A1 | 10/2012 | Lipscomb et al. |
| 2012/0277120 A1 | 11/2012 | Del Cardayre et al. |
| 2013/0004999 A1* | 1/2013 | Reth ................... C12N 9/0008 435/107 |
| 2013/0071893 A1 | 3/2013 | Lynch et al. |
| 2013/0078709 A1 | 3/2013 | Franklin et al. |
| 2013/0122541 A1 | 5/2013 | Lynch et al. |
| 2013/0149742 A1 | 6/2013 | Bower et al. |
| 2013/0217132 A1 | 8/2013 | Gill et al. |
| 2013/0252240 A1 | 9/2013 | Cutler et al. |
| 2014/0045231 A1 | 2/2014 | Lynch et al. |
| 2014/0068797 A1 | 3/2014 | Doudna et al. |
| 2014/0172318 A1 | 6/2014 | Fisher et al. |
| 2014/0180660 A1 | 6/2014 | Clancy et al. |
| 2014/0186942 A1 | 7/2014 | Serber et al. |
| 2014/0295457 A1 | 10/2014 | Broenstrup et al. |
| 2014/0356921 A1 | 12/2014 | Deng et al. |
| 2015/0031100 A1 | 1/2015 | Gill et al. |
| 2015/0056651 A1 | 2/2015 | Lynch et al. |
| 2015/0056684 A1 | 2/2015 | Lipscomb et al. |
| 2015/0132263 A1 | 5/2015 | Liu et al. |
| 2015/0140626 A1 | 5/2015 | Song et al. |
| 2015/0211013 A1 | 7/2015 | Emalfarb et al. |
| 2015/0275224 A1 | 10/2015 | Basra et al. |
| 2015/0284810 A1 | 10/2015 | Knight et al. |
| 2015/0284811 A1 | 10/2015 | Knight et al. |
| 2015/0299742 A1 | 10/2015 | Gill et al. |
| 2015/0315599 A1 | 11/2015 | Shetty et al. |
| 2015/0344916 A1 | 12/2015 | Lynch et al. |
| 2015/0368639 A1 | 12/2015 | Gill et al. |

(56) References Cited

U.S. PATENT DOCUMENTS

| | | |
|---|---|---|
| 2015/0376628 A1 | 12/2015 | Schoenherr et al. |
| 2016/0046961 A1 | 2/2016 | Jinek et al. |
| 2016/0060653 A1 | 3/2016 | Doudna et al. |
| 2016/0060654 A1 | 3/2016 | Doudna et al. |
| 2016/0068864 A1 | 3/2016 | Doudna et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0283651 A1 | 9/2016 | Knight et al. |
| 2016/0290132 A1 | 10/2016 | Knight et al. |
| 2016/0304905 A1 | 10/2016 | Hansen et al. |
| 2017/0009283 A1 | 1/2017 | Gill et al. |
| 2017/0051310 A1 | 2/2017 | Doudna et al. |
| 2017/0051312 A1 | 2/2017 | Jinek et al. |
| 2017/0067046 A1 | 3/2017 | Gill et al. |
| 2017/0073695 A1 | 3/2017 | Verruto et al. |
| 2017/0074889 A1 | 3/2017 | Shetty et al. |
| 2017/0114377 A1 | 4/2017 | Lynch et al. |
| 2017/0139078 A1 | 5/2017 | Knight et al. |
| 2017/0147742 A1 | 5/2017 | Jayaram et al. |
| 2017/0159045 A1 | 6/2017 | Serber et al. |
| 2017/0173086 A1 | 6/2017 | Boyle et al. |
| 2017/0240886 A1 | 8/2017 | Oleinikov |
| 2017/0240922 A1 | 8/2017 | Gill et al. |
| 2017/0240923 A1 | 8/2017 | Serber et al. |
| 2017/0316353 A1 | 11/2017 | Frewen et al. |
| 2017/0321198 A1 | 11/2017 | Severinov et al. |
| 2017/0321226 A1 | 11/2017 | Gill et al. |
| 2017/0342132 A1 | 11/2017 | Fraser et al. |
| 2017/0369870 A1 | 12/2017 | Gill et al. |
| 2017/0370213 A1 | 12/2017 | Knight et al. |
| 2018/0023120 A1 | 1/2018 | Kung et al. |
| 2018/0216099 A1 | 8/2018 | Serber et al. |
| 2018/0216100 A1 | 8/2018 | Serber et al. |
| 2018/0216101 A1 | 8/2018 | Serber et al. |
| 2020/0123496 A1 | 4/2020 | Manchester et al. |
| 2020/0123529 A1 | 4/2020 | Manchester et al. |
| 2020/0239897 A1 | 7/2020 | Serber et al. |

FOREIGN PATENT DOCUMENTS

| | | |
|---|---|---|
| DE | 19831609 A1 | 4/1999 |
| DE | 19947791 A1 | 4/2001 |
| DE | 19950409 A1 | 4/2001 |
| DE | 19959327 A1 | 6/2001 |
| DE | 19959328 A1 | 6/2001 |
| EP | 0131171 A1 | 1/1985 |
| EP | 0238023 A2 | 9/1987 |
| EP | 0197335 B1 | 2/1991 |
| EP | 0472869 A2 | 3/1992 |
| EP | 0356739 B1 | 12/1995 |
| EP | 0743016 A | 11/1996 |
| EP | 1108790 A2 | 6/2001 |
| EP | 0635574 B1 | 4/2003 |
| EP | 1331220 A2 | 7/2003 |
| EP | 0972081 B1 | 6/2007 |
| EP | 1546312 B1 | 7/2014 |
| GB | 1439728 A | 6/1976 |
| JP | 01-225487 A | 9/1989 |
| KR | 1020080042823 A | 5/2008 |
| WO | WO 1991/006628 A1 | 5/1991 |
| WO | WO 1995/022625 A1 | 8/1995 |
| WO | WO 1996/015246 A1 | 5/1996 |
| WO | WO 1996/033207 A1 | 10/1996 |
| WO | WO 1998/031837 A1 | 7/1998 |
| WO | WO 2000/020555 A2 | 4/2000 |
| WO | WO 2001/000843 A2 | 1/2001 |
| WO | WO 2001/012791 A1 | 2/2001 |
| WO | WO 2002/029032 A2 | 4/2002 |
| WO | WO 2003/014330 A2 | 2/2003 |
| WO | WO 2003/040373 A2 | 5/2003 |
| WO | WO 2004/054381 A1 | 7/2004 |
| WO | WO 2004/069996 A2 | 8/2004 |
| WO | WO 2005/006875 A2 | 1/2005 |
| WO | WO 2005/021772 A1 | 3/2005 |
| WO | WO 2006/069711 A1 | 7/2006 |
| WO | WO 2007/012078 A1 | 1/2007 |
| WO | WO 2007/015178 A2 | 2/2007 |
| WO | WO 2007/141580 A2 | 12/2007 |
| WO | WO 2008/088158 A1 | 7/2008 |
| WO | WO 2009/043803 A2 | 4/2009 |
| WO | WO 2009/126623 A2 | 10/2009 |
| WO | WO 2010/059763 A2 | 5/2010 |
| WO | WO 2010/075424 A2 | 7/2010 |
| WO | WO 2011/154147 A1 | 12/2011 |
| WO | WO 2012/082720 A2 | 6/2012 |
| WO | WO 2012/142591 A2 | 10/2012 |
| WO | WO 2012/149470 A1 | 11/2012 |
| WO | WO 2012/164565 A1 | 12/2012 |
| WO | WO 2013/066848 A1 | 5/2013 |
| WO | WO 2013/142578 A1 | 9/2013 |
| WO | WO 2014/011800 A1 | 1/2014 |
| WO | WO 2014/019527 A1 | 2/2014 |
| WO | WO 2014/089436 A1 | 6/2014 |
| WO | WO 2014/102782 A1 | 7/2014 |
| WO | WO 2015/070193 A1 | 5/2015 |
| WO | WO 2015/123339 A1 | 8/2015 |
| WO | WO 2015/148680 A1 | 10/2015 |
| WO | WO 2015/175793 A1 | 11/2015 |
| WO | WO 2006/028063 A1 | 3/2016 |
| WO | WO 2016/073690 A1 | 5/2016 |
| WO | WO 2016/196319 A1 | 12/2016 |
| WO | WO 2017/037304 A2 | 3/2017 |
| WO | WO 2017/100376 A2 | 6/2017 |
| WO | WO 2017/100377 A1 | 6/2017 |
| WO | WO 2017/189784 A1 | 11/2017 |
| WO | WO 2017/215790 A1 | 12/2017 |
| WO | WO 2017/223538 A1 | 12/2017 |
| WO | WO 2018/005655 A2 | 1/2018 |
| WO | WO 2018/005793 A1 | 1/2018 |
| WO | WO 2018/009372 A1 | 1/2018 |
| WO | WO 2018/013990 A1 | 1/2018 |
| WO | WO 2018/022972 A1 | 2/2018 |
| WO | WO 2018/071672 A1 | 4/2018 |
| WO | WO 2018/226964 A2 | 12/2018 |

OTHER PUBLICATIONS

Database DGene [Online], Accession No. AWF58557, Apr. 2, 2009, also published on Database Geneseq [Online] "C. glutamicum and fine chemical production (MCP) DNA SEQ ID:2731." XP002787739, retrieved from EBI accession No. GSN:AWF58557, Apr. 2, 2009.

Database Geneseq [Online] "Corynebacterium glutamicum tatE gene for Sec-independent protein secretion pathway component, complete cds." XP002787740, retrieved from EBI accession No. EM_STD:AB247377 sequence, Jan. 22, 2006, 1 page.

International Application No. PCT/US2016/065464, Invitation to Pay Additional Fees, dated Mar. 21, 2017, 5 pages.

International Application No. PCT/US2018/036472, International Preliminary Report on Patentability dated Dec. 10, 2019, 12 pages.

International Application No. PCT/US2018/036472, International Search Report and Written Opinion, dated Apr. 12, 2019, 25 pages.

International Application No. PCT/US2018/036472, Invitation to Pay Additional Fees, dated Sep. 10, 2018, 14 pages.

Kikuchi, et al., "Functional Analysis of the Twin-Arginine Translocation Pathway in Corynebacterium glutamicum ATCC 13869". Appl Environ Microbiol. (Nov. 2006); 72(11): 7183-7192. Epub Sep. 22, 2006.

Pátek, Miroslav, et al. "Promoters of Corynebacterium glutamicum". Journal of Biotechnology (2003); 104: 311-323.

U.S. Appl. No. 16/620,188, filed Jun. 7, 2018, US 2020-0239897 A1, Jul. 30, 2020, Pending.

"Designing a Million Genomes: Machine Learning, Automation and Biotech.", Strata + Hadoop World, Make Data Work conference, London, UK, May 5, 2015; https://www.youtube.com/watch?v=658kvYgrJBE&feature=youtu.be, Published on Oct. 7, 2015, Business-focused talk at Strata UK 2015 by Aaron Kimball, CTO of Zymergen Inc.

"The Data-Driven future of biotechnology." https://www.youtube.com/watch?v=IYmgJUHcG9g&feature=youtu.be&t=915, Strata + Hadoop World, NY Sep. 28-Oct. 1, 2015, Published on Nov. 15,

(56) References Cited

OTHER PUBLICATIONS

2015, Technical talk at Strata NY 2015 by Aaron Kimball, CTO of Zymergen Inc. about Zymergen's technology.
Adrio, Jose-Luis et al., "Recombinant organisms for production of industrial products", Bioengineered Bugs, 2010, pp. 116-131, vol. 1, No. 2.
Almeida, Elionor R.P., et al. "Transgenic expression of two marker genes under the control of an *Arabidopsis* rbcS promoter: Sequences encoding the Rubisco transit peptide increase expression levels." Molecular and General Genetics MGG (1989); 218.1: 78-86.
Alper et al., "Construction of lycopene-overproducing *E. coli* strains by combining systematic and combinatorial gene knockout targets." Nature Biotechnology (2005); 23 (5): 612-616.
Anonymous: "ABI 3900 High Throughput DNA Synthesizer", Mar. 1, 2001 (Mar. 1, 2001), URL:https://assets.thermofisher.com/TFS-Assets/LSG/manuals/cms_095580.pdf [retrieved on Jan. 2, 2018], 144 pages.
Askenazi, M., et al., "Integrating transcriptional and metabolite profiles to direct the engineering of lovastatin-producing fungal strains." Nat. Biotechnol. (2003); 21: 150-156.
Aslanidis, Charalampos, et al. "Ligation-independent cloning of PCR products (LIC-PCR)." Nucleic Acids Research (1990); 18.20: 6069-6074.
Azhayev, Alex V., et al. "Amide group assisted 3'-dephosphorylation of oligonucleotides synthesized on universal A-supports." Tetrahedron (2001); 57.23: 4977-4986.
Barcellos, Fernando Gomes, et al. "Genetic analysis of Aspergillus nidulans unstable transformants obtained by the biolistic process." Canadian Journal of Microbiology (1998); 44.12: 1137-1141.
Bartley, Bryan, et al. "Synthetic biology open language (SBOL) version 2.0.0." Journal of Integrative Bioinformatics (JIB) (2015); 12(2): 902-991.
Beal, et al., "An End-to-End Workflow for Engineering of Biological Networks from High-Level Specifications." ACS Synth. Biol. (2012); 1 (8): 317-331. Publication Date (Web): Jul. 10, 2012.
Becker, Daniel M., and Guarente, Leonard. "[12] High-efficiency transformation of yeast by electroporation." Methods in Enzymology (1991); 194: 182-187.
Bentley, David R., et al. "Accurate whole human genome sequencing using reversible terminator chemistry." Nature (2008); 456. 7218: 53-59.
Bernard, Philippe, et al. "The F plasmid CcdB protein induces efficient ATP-dependent DNA cleavage by gyrase." Journal of Molecular Biology (1993); 234.3: 534-541.
Bilitchenko, Al., "Eugene—a domain specific language for specifying and constraining synthetic biological parts, devices, and systems." PLoS One (2011); 6.4: e18882 (and Supplemental Data).
Boyd, J., et al. "Analysis of the diphtheria tox promoter by site-directed mutagenesis." Journal of Bacteriology (1988);170.12: 5949-5952.
Buchholz et al., "Platform Engineering of Corynebacterium glutamicum with Reduced Pyruvate Dehydrogenase Complex Activity for Improved Production of L-Lysine, L-Valine, and 2-Ketoisovalerate." Applied and Environmental Microbiology (2013); 79(18): 5566-5575.
Chakraborty, B. N., and Kapoor, M., "Transformation of filamentous fungi by electroporation." Nucleic Acids Research (1990); 18.22: 6737.
Chandran, et al., "TinkerCell: modular CAD tool for synthetic biology." Journal of Biological Engineering (2009); 3: 19, 17 pages.
Chen et al., "DeviceEditor visual biological CAD canvas." Journal of Biological Engineering (2012); 6:1, pp. 1-12.
Choi, J.H. et al., "Enhanced production of insulin-like growth factor I fusion protein in *Escherichia coli* by coexpression of the downregulated genes identified by transcriptome profiling." Appl. Environ. Microbiol. (2003); 69(8): 4737-4742.
Christiansen, Solveig K., et al. "Biolistic transformation of the obligate plant pathogenic fungus, *Erysiphe graminisf.* sp. *hordei*." Current Genetics (1995); 29.1: 100-102.
Christie, Peter J., and Gordon, Jay E. "The Agrobacterium Ti plasmids." Microbiology Spectrum (2014); 2.6.
Costanzo, Michael, et al. "The genetic landscape of a cell." Science (2010); 327 (5964): 425-431.
Cramer, Paula, et al. "Functional association between promoter structure and transcript alternative splicing." Proceedings of the National Academy of Sciences (1997); 94.21: 11456-11460.
Crameri, Andreas, et al. "Improved green fluorescent protein by molecular evolution using." Nat. Biotechnol (1996); 14.3: 315-319.
Crameri, Andreas, et al. "Construction and evolution of antibody-phage libraries by DMA shuffling." Nature Medicine (1996); 2.1: 100-102.
Crameri, Andreas, et al. "DNA shuffling of a family of genes from diverse species accelerates directed evolution." Nature (1998); 391.6664: 288-291.
Crameri, Andreas, et al. "Molecular evolution of an arsenate detoxification pathway by DNA shuffling." Nature Biotechnology (1997); 15.5: 436-438.
Czar, Michael J., et al. "Gene synthesis demystified." Trends in Biotechnology (2009); 27.2: 63-72.
Dahl, et al., "Multi-task Neural Networks for QSAR Predictions" Dept. of Computer Science, Univ. of Toronto, Jun. 2014, 21 pages (arXiv:1406.1231 [stat.ML]).
Dalphin, Mark E., et al. "TransTerm: A database of translational signals." Nucleic Acids Research (1996); 24.1: 216-218.
Damha, Masad J., et al. "An improved procedure for derivatization of controlled-pore glass beads for solid-phase oligonucleotide synthesis." Nucleic Acids Research (1990); 18.13 : 3813-3821.
Database EMBL [Online], "DNA fragment having promoter function." XP002767746, retrieved from EBI accession No. EM PAT:DD324094, Sep. 20, 2006.
Database Geneseq [Online] "Corynebacterium glutamicum DNA gyrase subunit B DNA, SEQ ID: 123." XP002767747, retrieved from EBI accession No. GSN: AEM36105. Mar. 8, 2007.
Database Geneseq [Online] "Corynebacterium glutamicum DNA gyrase subunit B DNA, SEQ ID: 123." XP002770467, retrieved from EBI accession No. GSN:AEM36105, Mar. 8, 2007.
Dauner, M., et al., "Intracellular carbon fluxes in riboflavin-producing Bacillus subtilis during growth on two-carbon substrate mixtures." Appl. Environ. Microbiol. (2002); 68(4): 1760-1771.
Drmanac, Radoje, et al. "Human genome sequencing using unchained base reads on self-assembling DNA nanoarrays." Science (2010); 327.5961: 78-81.
Duarte, N.C., et al., "Reconstruction and validation of *Saccharomyces scerevisiae* iND750, a fully compartmentalized genome-scale metabolic model." Genome Res. (2004); 14: 1298-1309.
Dunigan, L.K. and Shivnan, E. "High frequency transformation of whole cells of amino acid producing coryneform bacteria using high voltage electroporation." Nature Biotechnology (1989); 7.10: 1067-1070.
Durand, Roger, et al. "Transient expression of the β-glucuronidase gene after biolistic transformation of the anaerobic fungus Neocallimastix frontalis." Current Genetics (1997); 31.2 : 158-161.
Edwards, J.S. and Palsson, B.O., "Systems properties of the Haemophilus influenzae Rd metabolic genotype." J. Biol. Chem. (1999); 274(25): 17410-17416.
Edwards, J.S. and Palsson, B.O., "The *Escherichia coli* MG1655 in silico metabolic genotype: its definition, characteristics, and capabilities." Proc. Natl. Acad. Sci. U. S. A. (2000); 97(10): 5528-5533.
Eid, John, et al. "Real-time DNA sequencing from single polymerase molecules." Science (2009); 323.5910: 133-138.
Eikmanns, Bernhard J. "Identification, sequence analysis, and expression of a Corynebacterium glutamicum gene cluster encoding the three glycolytic enzymes glyceraldehyde-3-phosphate dehydrogenase, 3-phosphoglycerate kinase, and triosephosphate isomerase." Journal of Bacteriology (1992); 174.19: 6076-6086.
Eikmanns, Bernhard J., et al. "A family of Corynebacterium glutamicum/ *Escherichia coli* shuttle vectors for cloning, controlled gene expression, and promoter probing." Gene (1991); 102.1: 93-98.
Engler, Carola, et al. "A one pot, one step, precision cloning method with high throughput capability." PLoS One (2008); 3.11: e3647.
Fischer, S., et al., "The art of CHO cell engineering: A comprehensive retrospect and future perspectives." Biotechnology Advances (2015); 33: 1878-1896.

(56) References Cited

OTHER PUBLICATIONS

Fitzpatrick, R., et al. "Construction and characterization of recA mutant strains of Corynebacterium glutamicum and Brevibacterium lactofermentum." Applied Microbiology and Biotechnology (1994); 42.4: 575-580.

Förster, J., et al., "Genome-scale reconstruction of the *Saccharomyces cerevisiae* metabolic network." Genome Res. (2003); 13: 244-253.

Fox, Richard J., et al. "Improving catalytic function by ProSAR-driven enzyme evolution." Nature Biotechnology (2007); 25.3: 338-344.

Frewen, B., et al., "A Detailed, flexible model for sharing DNA concepts." IWBDA 2015, 7th International Workshop on Bio-Design Automation, University of Washington, pp. 66-67, Aug. 19-21, 2015 (Presentation and Poster), 86 pages.

Gardner et al., "Production of Citric Acid by Mutants of Aspergillus niger." J. Gen. Microbial (1956); 14: 228-237.

GenBank Accession No. CP010451.1 (Jan. 20, 2015), Corynebacterium glutamicum strain B253 DNA, complete genome, downloaded Jan. 12, 2018, 10 pages, https://www.ncbi.nlm.nih.gov/nuccore/748809780?sat=21&satkey=31610401.

GenBank CP001663.1, "Mycobacterium smegmatis str. MC2 155, complete genome." Jan. 31, 2014 (Jan. 31, 2014) [retrieved on Oct. 30, 2017, https://www.ncbi.nlm.nih.gov/nuccore/CP001663.1] genomic sequence nucleotide 4269453-4267996, 2 pages.

Gibson, Daniel G., et al. "Enzymatic assembly of DNA molecules up to several hundred kilobases." Nature Methods (2009); 6.5: 343-345.

Goosen, Theo, et al. "Transformation of Aspergillus niger using the homologous orotidine-5'-phosphate-decarboxylase gene." Current Genetics (1987); 11.6: 499-503.

GPU-Based Deep Learning Inference: A Performance and Power Analysis, NVidia Whitepaper, Nov. 2015, 12 pages.

Greger, Ingo H., et al. "Balancing transcriptional interference and initiation on the GAL7 promoter of *Saccharomyces cerevisiae*." Proceedings of the National Academy of Sciences (2000); 97.15: 8415-8420.

Guerrero, Carmen, et al. "Directed mutagenesis of a regulatory palindromic sequence upstream from the Brevibacterium lactofermentum tryptophan operon." Gene (1994); 138.1: 35-41.

Han, M.J. et al., "Engineering *Escherichia coli* for increased production of serine-rich proteins based on proteome profiling." Appl. Environ. Microbiol. (2003); 69(10): 5772-5781.

Han, M.J. et al., "Proteome analysis of metabolically engineered *Escherichia coli* cells producing poly(3-hydroxybutyrate)." J. Bacteriol. (2001); 183(1): 301-308.

Haynes, Jill A., and Britz, Margaret L. "The effect of growth conditions of Corynebacterium glutamicum on the transformation frequency obtained by electroporation." Microbiology (1990); 136. 2: 255-263.

Hermann, Thomas, et al. "Proteome analysis of Corynebacterium glutamicum." Electrophoresis (2001); 22.9: 1712-1723.

Hillson, N.J., "j5 DNA Assembly Design Automation Software." ACS Synthetic Biology (2011); 1: 14-21.

Hirao, et al., "L-Lysine production in continuous culture of an L-lysine hyperproducing mutant of Corynebacterium glutamicum." Applied Microbiology and Biotechnology (1989); 32 (3): 269-273.

Hong, Jiong, et al. "Cloning and functional expression of thermostable β-glucosidase gene from Thermoascus aurantiacus." Applied Microbiology and Biotechnology (2007); 73.6: 1331-1339.

Hong, S.H., et al., "The genome sequence of the capnophilic rumen bacterium Mannheimia succiniciproducens." Nat. Biotechnol. (2004); 22: 1275-1281.

Hui, A., et al. "Mutagenesis of the three bases preceding the start codon of the beta-galactosidase mRNA and its effect on translation in *Escherichia coli*." The EMBO Journal (1984); 3.3: 623-629.

Ikeda et al., "A genome-based approach to create a minimally mutated Corynebacterium glutamicum strain for efficient L-lysine production." J. Ind. Microbial. Biotechnol. (2006); 33(7): 610-615.

International Application No. PCT/US2016/065464, International Preliminary Report on Patentability, dated Jun. 12, 2018, 7 pages.
International Application No. PCT/US2016/065464, International Search Report and Written Opinion, dated Jun. 26, 2017, 14 pages.
International Application No. PCT/US2014/064911, International Preliminary Report on Patentability, dated May 17, 2016, 7 pages.
International Application No. PCT/US2014/064911, International Search Report and Written Opinion, dated Mar. 25, 2015, 9 pages.
International Application No. PCT/US2016/034723, International Preliminary Report on Patentability, dated Dec. 5, 2017, 9 pages.
International Application No. PCT/US2016/034723, International Search Report and Written Opinion, dated Oct. 24, 2016, 13 pages.
International Application No. PCT/US2016/065465, International Search Report and Written Opinion, dated Apr. 21, 2017, 22 pages.
International Application No. PCT/US2016/065465, Invitation to Pay Additional Fees, dated Feb. 23, 2017, 5 pages.
International Application No. PCT/US2016/065465, International Preliminary Report on Patentability, dated Jun. 12, 2018, 11 pages.
International Application No. PCT/US2017/029725, International Preliminary Report on Patentability, dated Oct. 30, 2018, 7 pages.
International Application No. PCT/US2017/029725, International Search Report and Written Opinion, dated Sep. 8, 2017, 10 pages.
International Application No. PCT/US2017/039452, International Search Report and Written Opinion, dated Sep. 29, 2017, 24 pages.
International Application No. PCT/US2017/039772, International Search Report and Written Opinion, dated Jan. 8, 2018, 18 pages.
International Application No. PCT/US2017/039997, International Search Report and Written Opinion, dated Nov. 9, 2017, 13 pages.
International Application No. PCT/US2017/042245, International Search Report and Written Opinion, dated Oct. 2, 2017, 11 pages.
International Application No. PCT/US2017/069086, International Search Report and Written Opinion, dated May 14, 2018, 18 pages.

Isojärvi, J., et al., "Draft Genome Sequence of Calothrix Strain 336/3, a Novel H2-Producing Cyanobacterium Isolated from a Finnish Lake." Genome Announcements (2015); 3 (1): 1-2, e01474-14.

Ito, Hisao, et al. "Transformation of intact yeast cells treated with alkali cations." Journal of Bacteriology (1983); 153.1: 163-168.

J5 DeviceEditor manual excerpt from https://j5.jbei.org/index.php/Main_Page_downloadedcontent available Apr. 19, 2016, 45 pages.

Jäger, W., et al. "Expression of the Bacillus subtilis sacB gene leads to sucrose sensitivity in the gram-positive bacterium Corynebacterium glutamicum but not in Streptomyces lividans." Journal of Bacteriology (1992);174.16: 5462-5465.

Jensen, Peter Ruhdal and Hammer, Karin. "Artificial promoters for metabolic optimization." Biotechnology and Bioengineering (1998); 58.2-3: 191-195.

Jones, Jonathan DG, et al. "High level expression of introduced chimaeric genes in regenerated transformed plants." The EMBO Journal (1985); 4.10: 2411.

Jungwirth, Britta, et al. "Triple transcriptional control of the resuscitation promoting factor 2 (rpf2) gene of Corynebacterium glutamicum by the regulators of acetate metabolism RamA and RamB and the cAMP-dependent regulator GlxR." FEMS Microbiology Letters (2008); 281.2: 190-197.

Kabir, M.M. and Shimizu, K., "Fermentation characteristics and protein expression patterns in a recombinant *Escherichia coli* mutant lacking phosphoglucose isomerase for poly(3-hydroxybutyrate) production." Appl. Microbiol. Biotechnol. (2003); 62: 244-255.

Kadonaga, James T. "Regulation of RNA polymerase II transcription by sequence-specific DNA binding factors." Cell (2004); 116.2: 247-257.

Kashyap, Hirak, et al. "Big data analytics in bioinformatics: A machine learning perspective." Journal of Latex Class Files (2014); 13(9): 20 pages.

Khanna, N.C., et al. "Identification of the template binding polypeptide in the pea chloroplast transcriptional complex." Nucleic Acids Research (1992); 20.1: 69-74.

Khudyakov, Yu E., et al. "Effect of structure of the initiator codon on translation in *E. coli*." FEBS Letters (1998); 232.2: 369-371.

(56) References Cited

OTHER PUBLICATIONS

Kikuchi, Yoshimi, et al. "Functional analysis of the twin-arginine translocation pathway in Corynebacterium glutamicum ATCC 13869." Applied and environmental microbiology (2006); 72.11: 7183-7192.

Kim, Jae Bum, et al. "Polony multiplex analysis of gene expression (PMAGE) in mouse hypertrophic cardiomyopathy." Science (2007); 316.5830: 1481-1484.

Kimball, A., "The Data-Driven Future of Biotechnology." Zymergen, Machine learning, automation, and biotech, Strata + Hadoop World, Make Data Work conference, Presentation, London, UK, May 5, 2015, 49 pages http://cdn.oreillystatic.com/en/assets/1/event/132/The%20data-driven%20future%20of%20biotechnology%20Presentation.pdf.

Kirchner, Oliver and Tauch, Andreas. "Tools for genetic engineering in the amino acid-producing bacterium Corynebacteriumglutamicum." Journal of Biotechnology (2003); 104.1: 287-299.

Kotera, Ippei, et al. "A high-throughput and single-tube recombination of crude PCR products using a DNA polymerase inhibitor and type IIS restriction enzyme." Journal of Biotechnology (2008); 137.1: 1-7.

Kozlov, Igor A., et al. "Significant improvement of quality for long oligonucleotides by using controlled pore glass with large pores." Nucleosides, Nucleotides and Nucleic Acids (2005); 24.5-7: 1037-1041.

Krämer, O., et al., "Methods in mammalian cell line engineering: from random mutagenesis to sequence-specific approaches." Appl Microbiol Biotechnol (2010); 88: 425-436.

Krömer, J.O., et al., "In-depth profiling of lysine-producing Corynebacterium glutamicum by combined analysis of the transcriptome, metabolome, and fluxome." J. Bacteriol. (2004); 186(6): 1769-1784.

Kuo, Chih-Chung, et al., "The emerging role of systems biology for engineering protein production in CHO cells." Current Opinion in Biotechnology (2018); 51: 64-69.

Labarre, Jean, et al. "Gene replacement, integration, and amplification at the gdhA locus of Corynebacterium glutamicum." Journal of Bacteriology (1993); 175.4: 1001-1007.

Lee, et al., "A Highly Characterized Yeast Toolkit for Modular, Multipart Assembly." ACS Synthetic Biology (2015); 4(9): 975-986 (Published Apr. 14, 2015).

Lee, J.H., et al., "Global analyses of transcriptomes and proteomes of a parent strain and an L-threonine-overproducing mutant strain." J. Bacteriol. (2003); 185(18): 5442-5451.

Lee, Joo-Young, et al. "Adaptive evolution of Corynebacterium glutamicum resistant to oxidative stress and its global gene expression profiling." Biotechnology Letters (2013); 35.5: 709-717.

Lee, Sang Yup, et al., "Systems biotechnology for strain improvement." Trends in Biotechnology (2005); 23(7): 349-358.

Leng, Xiaoyan, et al. "Classification using functional data analysis for temporal gene expression data." Bioinformatics (2006); 22.1: 68-76.

Li, et al., "C-Brick: A New Standard for Assembly of Biological Parts Using Cpf1." ACS Synth. Biol. (2016); 5(12): 1383-1388.

Libbrecht, Maxwell W., et al. "Machine learning applications in genetics and genomics." Nature Reviews Genetics (2015); 16.6: 321-332.

Lindroth, Peter, and Mopper, Kenneth. "High performance liquid chromatographic determination of subpicomole amounts of amino acids by precolumn fluorescence derivatization withoff-phthaldialdehyde." Anal. Chem (1979); 51.11: 1667-1674.

Liu, et al., "Developing a high-throughput screening method for threonine overproduction based on an artificial promoter." Microbial Cell Factories (2015); 14:121, 11 pages.

Makrides, Savvas C. "Strategies for achieving high-level expression of genes in *Escherichia coli*." Microbiological Reviews (1996); 60.3: 512-538.

Malumbres, Marcos, et al. "Codon preference in corynebacteria." Gene (1993); 134.1: 15-24.

Margulies, Marcel, et al. "Genome sequencing in microfabricated high-density picolitre reactors." Nature (2005); 437.7057: 376-380.

Martin, J. F., et al. "Cloning Systems in Amino Acid-Producing Corynebacteria." Nature Biotechnology (1987); 5.2: 137-146.

Menkel, et al., "Influence of increased aspartate availability on lysine formation by a recombinant strain of Corynebacterium glutamicum and utilization of fumarate." Appl. Environ. Microbiol. (1989); 55(3): 684-688.

Mockel, Bettina, et al. "Functional and structural analyses of threonine dehydratase from Corynebacterium glutamicum." Journal of Bacteriology (1992); 174.24: 8065-8072.

Mockel, Bettina, et al. "Threonine dehydratases of Corynebacterium glutamicum with altered allosteric control: their generation and biochemical and structural analysis." Molecular Microbiology (1994); 13.5: 833-842.

Molenaar, et al., "Biochemical and genetic characterization of the membrane-associated malate dehydrogenase (acceptor) from Corynebacterium glutamicum." Eur J Biochem. (1998); 254(2): 395-403.

Moore, Jeffrey C., et al. "Strategies for the in vitro evolution of protein function: enzyme evolution by random recombination of improved sequences." Journal of Molecular Biology (1997); 272.3: 336-347.

Murray, Elizabeth E. et al. "Codon usage in plant genes." Nucleic Acids Research (1989); 17.2: 477-498.

Nakashima, Nobutaka, et al. "Bacterial cellular engineering by genome editing and gene silencing." International Journal of Molecular Sciences (2014); 15.2: 2773-2793.

Neumann, Susanne, and Quiñones, Ariel. "Discoordinate gene expression of gyrA and gyrB in response to DNA gyrase inhibition in *Escherichia coli*." Journal of Basic Microbiology (1997); 37.1: 53-69.

Ohnishi et al., "A novel methodology employing Corynebacterium glutamicum genome information to generate a new L-lysine-producing mutant." Appl. Microbial Biotechnol (2002); 58(2): 217-223. Published online: Dec. 8, 2001.

Ohnishi, J. et al., "Efficient 40 degrees C fermentation of L-lysine by a new Corynebacterium glutamicum mutant developed by genome breeding." Appl. Microbiol. Biotechnol. (2003); 62: 69-75.

Paek, Se-Hwan, et al. "Development of rapid one-step immunochromatographic assay." Methods (2000); 22.1: 53-60.

Parry, Neil J., et al. "Biochemical characterization and mechanism of action of a thermostable β-glucosidase purified from Thermoascus aurantiacus." Biochemical Journal (2001); 353.1: 117-127.

Pátek, Miroslav, et al. "Promoters from Corynebacterium glutamicum: cloning, molecular analysis and search for a consensus motif." Microbiology (1996); 142.5: 1297-1309.

Pedersen and Phillips, "Towards programming languages for genetic engineering of living cells." J.R. Soc. Interface (2009); 6 (Suppl 4): S437-S450. Published online Apr. 15, 2009.

Peters-Wendisch, Petra G., et al. "Pyruvate carboxylase from Corynebacterium glutamicum: characterization, expression and inactivation of the pyc gene." Microbiology (1998); 144.4: 915-927.

Pfeifer-Sancar, Katharina, et al. "Comprehensive analysis of the Corynebacterium glutamicum transcriptome using an improved RNAseq technique." BMC Genomics (2013):14.1: 888, 23 pages.

Price, N.D., et al., "Genome-scale models of microbial cells: evaluating the consequences of constraints." Nat. Rev. Microbiol. (2004); 2: 886-897.

Prompramote, Supawan, et al. "Machine learning in bioinformatics." Bioinformatics Technologies. Springer Berlin Heidelberg (2005); pp. 117-153.

Qiu, Zhihao, et al. "The *Escherichia coli* polB Locus is Identical to din A, the Structural Gene for DNA Polymerase II Characterization of Pol II Purified From A polB Mutant." Journal of Biological Chemistry (1997); 272.13: 8611-8617.

Rastegari, Hilda et al., "Improvement in the Production of L-Lysine by Over-expression of Aspartokinase (ASK) in C. glutamicum ATCC-21799", Tropical Journal of Pharmaceutical Research, Feb. 2013, pp. 51-56, vol. 12, No. 1.

Reddy, Prasad, et al. "Translational efficiency of the *Escherichia coli* adenylate cyclase gene: mutating the UUG initiation codon to

(56) References Cited

OTHER PUBLICATIONS

GUG or AUG results in increased gene expression." Proceedings of the National Academy of Sciences (1985); 82.17: 5656-5660.

Reed, J.L., et al., "An expanded genome-scale model of *Escherichia coli* K-12 (iJR904 GSM/GPR)." Genome Biol. (2003); 4, R54.

Reimer, et al., "High-Throughput Screening of a Corynebacterium glutamicum Mutant Library on Genomic and Metabolic Level." PLoS One (2014); 9(2): e86799, 12 pages.

Reinscheid, Dieter J., et al. "Stable expression of hom-1-thrB in Corynebacterium glutamicum and its effect on the carbon flux to threonine and related amino acids." Applied and Environmental Microbiology (1994); 60.1: 126-132.

Rey, Daniel Alexander, et al. "The putative transcriptional repressor McbR, member of the TetR-family, is involved in the regulation of the metabolic network directing the synthesis of sulfur containing amino acids in Corynebacterium glutamicum." Journal of Biotechnology (2003); 103.1: 51-65.

Reyrat, Jean-Marc, et al. "Counterselectable markers: untapped tools for bacterial genetics and pathogenesis." Infection and Immunity (1998); 66.9: 4011-4017.

Ricciardelli, Carmela, et al. "Development and characterization of primary cultures of smooth muscle cells from the fibromuscular stroma of the guinea pig prostate." In Vitro Cellular & Developmental Biology (1989); 25.11: 1016-1024.

Rückert, C., et al., "Genome-wide analysis of the L-methionine biosynthetic pathway in Corynebacterium glutamicum by targeted gene deletion and homologous complementation." J. Biotechnol. (2003); 104: 213-228.

Rytter, et al., "Synthetic promoter libraries for Corynebacterium glutamicum." Applied Microbiology and Biotechnology (2014); 98 (6): 2617-2623.

Sahm, Hermann, et al. "d-Pantothenate Synthesis in Corynebacterium glutamicum and Use of panBC and Genes Encoding I-Valine Synthesis ford-Pantothenate Overproduction." Applied and Environmental Microbiology (1999); 65.5: 1973-1979.

Sasaki, et al. "Simultaneous utilization of D-cellobiose, D-glucose, and D-xylose by recombinant Corynebacterium glutamicum under oxygen-deprived conditions." Applied Microbiology and Biotechnology (2008); 81.4: 691-699.

Schäfer, A., et al. "Increased fertility of Corynebacterium glutamicum recipients in intergeneric matings with *Escherichia coli* after stress exposure." Applied and Environmental Microbiology (1994); 60.2: 756-759.

Schäfer, Andreas, et al. "Small mobilizable multi-purpose cloning vectors derived from the *Escherichia coli* plasmids pK18 and pK19: selection of defined deletions in the chromosome of Corynebacterium glutamicum." Gene (1994); 145.1: 69-73.

Schilling, C.H., et al., "Genome-scale metabolic model of Helicobacter pylori 26695." J. Bacteriol. (2002); 184(16): 4582-4593.

Schrumpf, Barbel, et al. "A functionally split pathway for lysine synthesis in Corynebacterium glutamicium." Journal of Bacteriology (1991); 173.14: 4510-4516.

Schwarzer, Astrid, and Pühler, Alfred. "Manipulation of Corynebacterium glutamicum by Gene Disruption and Replacement." Nature Biotechnology (1991); 9.1: 84-87.

Serwold-Davis, Theresa M., et al. "Localization of an origin of replication in Corynebacterium diphtheriae broad host range plasmid pNG2 that also functions in *Escherichia coli*." FEMS Microbiology Letters (1990) 66.1-3: 119-123.

Shevade, Shirish Krishnaj, et al. "A simple and efficient algorithm for gene selection using sparse logistic regression." Bioinformatics (2003); 19.17: 2246-2253.

Shuman, Stewart. "Novel approach to molecular cloning and polynucleotide synthesis using vaccinia DNA topoisomerase." Journal of Biological Chemistry (1994); 269.51: 32678-32684.

Sierzchala, Agnieszka B., et al. "Solid-phase oligodeoxynucleotide synthesis: a two-step cycle using peroxy anion deprotection." Journal of the American Chemical Society (2003); 125.44: 13427-13441.

Simon, R., et al. "A broad host range mobilization system for in vivo genetic engineering: transposon mutagenesis in gram negative bacteria." Nature Biotechnology (1983); 1.9: 784-791.

Snitkin and Segre, "Epistatic Interaction Maps Relative to Multiple Metabolic Phenotypes." PLoS Genet (2011); 7(2): 61001294.

Sonnen, Hans, et al. "Characterization of pGA1, a new plasmid from Corynebacterium glutamicum LP-6." Gene (1991); 107.1: 69-74.

Spackman, Darrel H., et al. "Automatic recording apparatus for use in the chromatography of amino acids." Analytical Chemistry (1958); 30: 1190-1206.

Spratt, Brian G., et al. "Kanamycin-resistant vectors that are analogues of plasmids pUC8, pUC9, pEMBL8 and pEMBL9." Gene (1986); 41.2: 337-342.

Stansen, Corinna, et al. "Characterization of a Corynebacterium glutamicum lactate utilization operon induced during temperature-triggered glutamate production." Applied and environmental microbiology (2005); 71.10: 5920-5928.

Stemmer, Willem P. "DNA shuffling by random fragmentation and reassembly: In vitro recombination for molecular evolution." Proceedings of the National Academy of Sciences (1994); 91.22: 10747-10751.

Stemmer, Willem P.C. "Rapid evolution of a protein in vitro by DNA shuffling." Nature (1994); 370.6488: 389-391.

Stemmer, Willem P.C. "The evolution of molecular computation." Science (1995); 270.5241: 1510-1511.

Stemmer, Willem P.C., "Searching Sequence Space" Nature Biotechnology (1995); 13: 549-553.

Stemmer, Willem P.C., et al. "Single-step assembly of a gene and entire plasmid from large numbers of oligodeoxyribonucleotides." Gene (1995); 164.1: 49-53.

Stenström, C. Magnus, et al. "Cooperative effects by the initiation codon and its flanking regions on translation initiation." Gene (2001); 273.2: 259-265.

Stephanopoulos, G., "Exploiting biological complexity for strain improvement through systems biology." Nat. Biotechnol. (2004); 22: 1261-1267.

Student. "The probable error of a mean." Biometrika (1908); 6(1): 1-25.

Su, Shin-San, et al. "*Escherichia coli* mutS-encoded protein binds to mismatched DNA base pairs." Proceedings of the National Academy of Sciences (1986); 83.14: 5057-5061.

Suda, Masako, et al. "Transcriptional regulation of Corynebacterium glutamicum methionine biosynthesis genes in response to methionine supplementation under oxygen deprivation." Applied Microbiology and Biotechnology (2008); 81.3: 505-513.

Sugimoto, Masakazu, et al. "Sequence analysis of functional regions of homoserine dehydrogenase genes from L-lysine and L-threonine-producing mutants of Brevibacterium lactofermentum." Bioscience, Biotechnology, and Biochemistry (1997); 61.10: 1760-1762.

Tauch, Andreas, et al. "Corynebacterium glutamicum DNA is subjected to methylation-restriction in *Escherichia coli*." FEMS Microbiology Letters (1994); 123.3: 343-347.

Tauch, Andreas, et al. "Plasmids in Corynebacterium glutamicum and their molecular classification by comparative genomics." Journal of Biotechnology (2003); 104.1: 27-40.

Tear, Crystal Jing Ying, et al. "Excision of Unstable Artificial Gene-Specific Inverted Repeats Mediates Scar-Free Gene Deletions in *Escherichia coli*." Applied Biochemistry and Biotechnology (2014); 175.4: 1858-1867.

Thierbach, Georg, et al. "Transformation of spheroplasts and protoplasts of Corynebacterium glutamicum." Applied Microbiology and Biotechnology (1998); 29.4: 356-362.

Third Party Observation filed in connection with International Application No. PCT/US2016/065465, dated Apr. 6, 2018, 12 pages.

Third-Party Submission filed with the U.S. Patent and Trademark Office on Dec. 7, 2017, in connection with U.S. Appl. No. 15/396,230, 14 pages.

Third-Party Submission filed with the U.S. Patent and Trademark Office on May 1, 2018, in connection with U.S. Appl. No. 15/140,296, 63 pages.

(56) References Cited

OTHER PUBLICATIONS

Tian, Jingdong, et al. "Advancing high-throughput gene synthesis technology." Molecular BioSystems (2009); 5.7: 714-722.

Trikka et al., "Iterative carotenogenic screens identify combinations of yeast gene deletions that enhance sclareol production." Microbial Cell Factories (2015); 14:60 (Published on line Apr. 24, 2015), 1:19, 19 pages.

Tsuchiya, Makoto, and Morinaga, Yasushi. "Genetic control systems of Escherichia coli can confer inducible expression of cloned genes in coryneform bacteria." Nature Biotechnology (1998); 6.4: 428-430.

Tummala, S.B. et al., "Transcriptional analysis of product concentration driven changes in cellular programs of recombinant Clostridium acetobutylicum strains." Biotechnol. Bioeng. (2003); 84, 842-854.

Vašicová, Pavla, et al. "Analysis of the Corynebacterium glutamicum dapA promoter." Journal of Bacteriology (1999);181.19: 6188-6191.

Voskuil, Martin I., et al. "The—16 region of Bacillus subtilis and other gram-positive bacterial promoters." Nucleic Acids Research (1998); 26.15: 3584-3590.

Wagner, Robert, et al. "Mutation detection using immobilized mismatch binding protein (MutS)." Nucleic Acids Research (1995); 23.19: 3944-3948.

Wang et al., "Programming cells by multiplex genome engineering and accelerated evolution." Nature (2009); 460: 894-898.

Wang, Junping, et al. "An improved recombineering approach by adding RecA to λ red recombination." Molecular Biotechnology (2006); 32.1: 43-53.

Weber, Ernst, et al. "Assembly of designer TAL effectors by Golden Gate cloning." PLoS One (2011); 6.5: e19722.

West, Steven and Proudfoot, Nicholas J. "Transcriptional termination enhances protein expression in human cells." Molecular Cell (2009); 33.3: 354-364.

West, Steven, et al. "Molecular dissection of mammalian RNA polymerase II transcriptional termination." Molecular Cell (2008); 29.5: 600-610.

Wilson, Erin H., et al., "Genotype specification language." ACS Synthetic Biology (2016); 5 (6): 471-478.

WIPO Communication dated Apr. 10, 2018 to Applicant, Zymergen Inc. in connection with International Application No. PCT/US2016/065465, advising of third party observation filed Apr. 6, 2018, 1 page.

Wittmann, C. and Heinzle, E., "Modeling and experimental design for metabolic flux analysis of lysine-producing Corynebacteria by mass spectrometry." Metab. Eng. (2001); 3:173-191.

Yelton, M. Melanie, et al. "Transformation of Aspergillus nidulans by using a trpC plasmid." Proceedings of the National Academy of Sciences (1984); 81 (5): 1470-1474.

Yoon, S.H., et al., "Combined transcriptome and proteome analysis of Escherichia coli during high Cell density culture." Biotechnol. Bioeng. (2003); 81: 753-767.

Zetsche, et al., "Cpf1 is a Single RNA-Guided Endonuclease of a Class 2 CRISPR-Cas System." Cell (2015); 163 (2): 759-771.

Zhang, Ji-Hu, et al. "Directed evolution of a fucosidase from a galactosidase by DNA shuffling and screening." Proceedings of the National Academy of Sciences (1997); 94 (9): 4504-4509.

Peng, S., et al., "Co-expression of chaperones from P. furiosus enhanced the soluble expression of the recombinant hyperthermophilic α-amylase in E. coli". Cell Stress and Chaperones (Feb. 10, 2016); 21(3): 477-484. Epub Feb. 10, 2016.

GenBank: AX063925.1, "Sequence 207 from Patent WO0100843", Pompejus, M., et al., GenBank, Jan. 24, 2001, 1 page.

* cited by examiner

PROMOTERS FROM *CORYNEBACTERIUM GLUTAMICUM*

CROSS REFERENCE

This application is a national stage application, filed under 35 U.S.C. § 371, of International Patent Application No. PCT/US2016/065464, filed on Dec. 7, 2016, which claims the benefit of priority to U.S. Provisional Patent Application No. 62/264,232, filed Dec. 7, 2015, and U.S. Provisional Patent Application No. 62/431,409, filed Dec. 7, 2016, each of which applications are incorporated herein by reference in their entireties.

INCORPORATION BY REFERENCE OF SEQUENCE LISTING PROVIDED AS A TEXT FILE

A Sequence Listing is provided herewith as a text file, "AMG-001-PCT_SL.txt" created on Nov. 30, 2016 and having a size of 4,575 bytes. The contents of the text file are incorporated by reference herein in their entirety.

BACKGROUND

Field

The invention relates to native promoters comprising polynucleotides isolated from *Corynebacterium glutamicum*, and mutant promoters derived therefrom, host cells and recombinant vectors comprising the promoters, and methods of modifying the expression of target genes and producing biomolecules comprising culturing the host cells.

Description of the Related Art

Strains of coryneform bacteria, in particular *Corynebacterium glutamicum*, play a significant role in the production of biomolecules such as amino acids, organic acids, vitamins, nucleosides and nucleotides, and continuous efforts are being made to improve production processes. Said processes may be improved with respect to fermentation related measures such as, for example, stirring and oxygen supply, or the composition of nutrient media, such as, for example, sugar concentration during fermentation, or the work-up into the product form, for example by means of ion exchange chromatography, or the intrinsic performance characteristics of the microorganism itself.

Performance characteristics can include, for example, yield, titer, productivity, by-product elimination, tolerance to process excursions, optimal growth temperature and growth rate. One way to improve performance of a microbial strain is to increase the expression of genes that control the production of a metabolite. Increasing expression of a gene can increase the activity of an enzyme that is encoded by that gene. Increasing enzyme activity can increase the rate of synthesis of the metabolic products made by the pathway to which that enzyme belongs. In some instances, increasing the rate of production of a metabolite can unbalance other cellular processes and inhibit growth of a microbial culture. Sometimes, down regulating activity is important to improve performance of a strain. For example, re-directing flux away from by-products can improve yield. Accordingly, fine-tuning of expression levels of the various components simultaneously within a metabolic pathway is often necessary.

Promoters regulate the rate at which genes are transcribed and can influence transcription in a variety of ways. Constitutive promoters, for example, direct the transcription of their associated genes at a constant rate regardless of the internal or external cellular conditions, while regulatable promoters increase or decrease the rate at which a gene is transcribed depending on the internal and/or the external cellular conditions, e.g. growth rate, temperature, responses to specific environmental chemicals, and the like. Promoters can be isolated from their normal cellular contexts and engineered to regulate the expression of virtually any gene, enabling the effective modification of cellular growth, product yield and/or other phenotypes of interest.

There is clearly a need for a broader assortment of well-defined *Corynebacterium* species promoters than has been heretofore described. Such promoters would be useful in the coordinated expression of genes in coryneform cells. For example, a collection of *C. glutamicum* promoters would facilitate the industrial-scale production of biomolecules in *C. glutamicum* cells by enhancing the expression of genes that encode components of the biosynthetic pathways for the desired biomolecules. The promoters described herein help meet these and other needs.

BRIEF SUMMARY

In brief, the present disclosure is directed to native promoters comprising polynucleotides isolated from *Corynebacterium glutamicum*, and mutant promoters derived therefrom, which can each be encoded by short DNA sequences, ideally less than 100 base pairs, and which together represent a ladder of constitutive promoters having incrementally increasing expression levels. It is possible for various genes to be expressed advantageously under the control of said promoters.

One embodiment of the present invention relates to a first promoter polynucleotide comprising a sequence selected from: SEQ ID NO:1, SEQ ID NO:5, or SEQ ID NO:7. In some embodiments, the first promoter polynucleotide consists of a sequence selected from: SEQ ID NO:1, SEQ ID NO:5, or SEQ ID NO:7. One embodiment of the present invention relates to combinations of promoter polynucleotides comprising at least two first promoter polynucleotides described herein. One embodiment of the present invention relates to combinations of promoter polynucleotides comprising at least one first promoter polynucleotide described herein, and at least one second promoter polynucleotide comprising a sequence selected from the group consisting of: SEQ ID NO:2, SEQ ID NO:3, SEQ ID NO:4, SEQ ID NO:6, and SEQ ID NO:8. One embodiment of the present invention relates to combinations of promoter polynucleotides comprising at least one first promoter polynucleotide described herein, and at least one second promoter polynucleotide consisting of a sequence selected from the group consisting of: SEQ ID NO:2, SEQ ID NO:3, SEQ ID NO:4, SEQ ID NO:6, and SEQ ID NO:8.

One embodiment of the present invention relates to host cells comprising the first promoter polynucleotide described herein. One embodiment of the present invention relates to recombinant vectors comprising the first promoter polynucleotide described herein. In some embodiments, the first promoter polynucleotide is functionally linked to a first target gene. One embodiment of the present invention relates to host cells comprising the combinations of promoter polynucleotides described herein. One embodiment of the present invention relates to recombinant vectors comprising the combinations of promoter polynucleotides described herein. In some embodiments, each promoter polynucleotide is functionally linked to a different target gene. In some embodiments, the target genes are part of the same metabolic pathway. In some embodiments, the target genes are not part of the same metabolic pathway. One embodiment of the present invention relates to host cells transformed with the recombinant vectors described herein.

One embodiment of the present invention relates to host cells comprising at least one promoter polynucleotide functionally linked to a target gene; wherein the promoter polynucleotide comprises a sequence selected from: SEQ ID NO:1, SEQ ID NO:2, SEQ ID NO:3, SEQ ID NO:4, SEQ ID NO:5, SEQ ID NO:6, SEQ ID NO:7, and SEQ ID NO:8; wherein when the promoter polynucleotide comprises a sequence selected from: SEQ ID NO:2, SEQ ID NO:3, SEQ ID NO:4, SEQ ID NO:6, or SEQ ID NO:8, the target gene is other than the promoter polynucleotide's endogenous gene. In some embodiments, the host cell comprises at least two promoter polynucleotides, wherein each promoter polynucleotide is functionally linked to a different target gene. One embodiment of the present invention relates to recombinant vectors comprising at least one promoter polynucleotide functionally linked to a target gene; wherein the promoter polynucleotide comprises a sequence selected from: SEQ ID NO:1, SEQ ID NO:2, SEQ ID NO:3, SEQ ID NO:4, SEQ ID NO:5, SEQ ID NO:6, SEQ ID NO:7, and SEQ ID NO:8; wherein when the promoter polynucleotide comprises a sequence selected from: SEQ ID NO:2, SEQ ID NO:3, SEQ ID NO:4, SEQ ID NO:6, or SEQ ID NO:8, the target gene is other than the promoter polynucleotide's endogenous gene. In some embodiments, the recombinant vector comprises at least two promoter polynucleotides, wherein each promoter polynucleotide is functionally linked to a different target gene. In some embodiments, the target genes are part of the same metabolic pathway. In some embodiments, the target genes are not part of the same metabolic pathway. One embodiment of the present invention relates to host cells transformed with the recombinant vectors described herein.

One embodiment of the present invention relates to methods of modifying the expression of one or more target genes, comprising culturing a host cell described herein, wherein the modification of each target gene is independently selected from: up-regulating and down-regulating. The target gene preferably codes for one or more polypeptides or proteins of the biosynthetic pathway of biomolecules including, e.g., amino acids, organic acids, nucleic acids, proteins, and polymers.

Another embodiment of the present invention relates to methods of producing a biomolecule comprising culturing a host cell described herein, under conditions suitable for producing the biomolecule. In some embodiments the target gene is associated with a biosynthetic pathway producing a biomolecule selected from: amino acids, organic acids, flavors and fragrances, biofuels, proteins and enzymes, polymers/monomers and other biomaterials, lipids, nucleic acids, small molecule therapeutics, protein or peptide therapeutics, fine chemicals, and nutraceuticals. In preferred embodiments, the biomolecule is an L-amino acid. In specific embodiments, the L-amino acid is lysine.

In some embodiments, the host cell belongs to genus *Corynebacterium*. In some embodiments, the host cell is *Corynebacterium glutamicum*.

DETAILED DESCRIPTION

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

As used herein, the term "recombinant nucleic acid molecule" refers to a recombinant DNA molecule or a recombinant RNA molecule. A recombinant nucleic acid molecule is any nucleic acid molecule containing joined nucleic acid molecules from different original sources and not naturally attached together. Recombinant RNA molecules include RNA molecules transcribed from recombinant DNA molecules. In particular, a recombinant nucleic acid molecule includes a nucleic acid molecule comprising a promoter of SEQ ID NOs:1 to 8 functionally linked to a heterologous target gene.

As used herein, the term "heterologous target gene" refers to any gene or coding sequence that is not controlled in its natural state (e.g., within a non-genetically modified cell) by the promoter to which it is operably linked in a particular genome. As provided herein, all target genes functionally linked to non-naturally occurring promoters are considered "heterologous target genes". More specifically, as promoter polynucleotide sequences of SEQ ID NOs:1, 5, and 7 do not occur in nature, all functionally linked target gene sequences are "heterologous target gene" sequences. As used herein, a heterologous target gene can include one or more target genes that are part of an operon. That is, the endogenous promoter of an operon is replaced with a promoter polynucleotide sequence having a nucleic sequence of SEQ ID NOs:1 to 8. As used herein, the term "promoter polynucleotide sequence" refers to nucleic acids having a sequence as recited in the associated SEQ ID NO.

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Polynucleotides Having Promoter Activity

Figure 1:
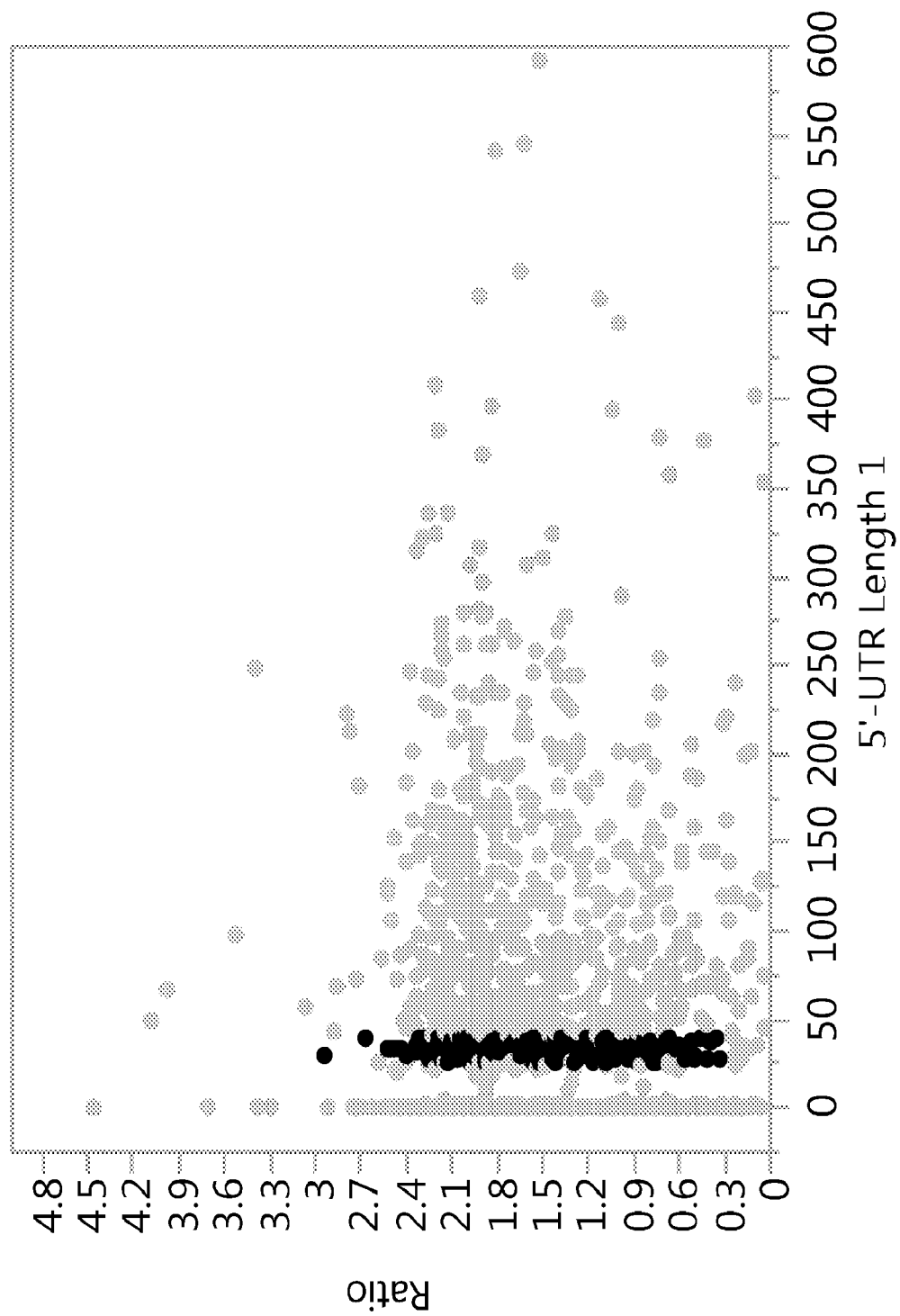
FIG. 1 shows a graph of 5' UTR length (x axis) versus expression ratio across two growth conditions (y axis) for each gene in the *C. glutamicum* ATCC 13032 genome. Genes having both an expression ratio across the two growth conditions of between 0.33 and 3, and a 5' UTR length of between 26 and 40 base pairs are represented by black circles. Genes that failed to match both criteria are represented by grey circles.

Native *C. glutamicum* promoters were identified that satisfy both of the following criteria: 1) represent a ladder of constitutive promoters, i.e., a plurality of promoters with incrementally increasing levels of promoter activity; and 2) encoded by short DNA sequences, ideally less than 100 base pairs. A published data set describing global gene expression levels in *C. glutamicum* ATCC 13032 (Lee et al., Biotechnol Lett (2013) 35:709-717) was examined to identify genes that were constitutively expressed across different growth conditions. Genes whose expression level remained constant (defined as a ratio of expression between 0.33 and 3) across two growth conditions, namely chemostat growth in minimal media with and without the addition of hydrogen peroxide satisfied the first criterion. A published data set describing the *C. glutamicum* ATCC 13032 transcriptome (Pfeifer-Sancar et al., BMC Genomics 2013, 14:888) was examined to find genes with compact promoters, i.e. those consisting of the 60 base pair core promoter region and a 5' untranslated region between 26 and 40 base pairs in length. The two data sets were cross-referenced to identify promoters that satisfied both criteria. See FIG. 1. The following five wild-type promoters were identified (Table 1).

TABLE 1

Promoters of *C. glutamicum* Having Increasing Levels of Expression and Constituent Expression Under Different Growth Conditions

| Strain | SEQ ID NO | Mean Activity |
|---|---|---|
| Pcg1860-eyfp | 2 | 89243 |
| Pcg0007-eyfp | 3 | 44527 |
| Pcg0755-eyfp | 4 | 43592 |
| Pcg3381-eyfp | 6 | 4723 |
| Pcg3121-eyfp | 8 | 98 |

The wild-type promoters cg1860, and cg3121 are not described in the literature. The wild-type promoter cg0007-gyrB is also not described in the literature, however, Neumann and Quiñones, (J Basic Microbiol. 1997; 37(1):53-69) describes regulation of gyrB gene expression in *E. coli*. The wild-type promoter cg0755 is a known part of the methionine biosynthesis pathway (Suda et al., Appl Microbiol Biotechnol (2008) 81:505-513; and Rey et al., Journal of Biotechnology 103 (2003) 51-65). The wild-type promoter cg3381 is a tatA homolog. The tatA pathway in *Corynebacterium* is described by Kikuchi et al., Applied and Environmental Microbiology, November 2006, p. 7183-7192. The strong constitutive promoter Pcg0007 was chosen for mutagenesis. Four out of six positions in the predicted—10 element (TAAGAT) of Pcg0007 were randomized to generate both stronger and attenuated promoter variants (SEQ ID NOs 1, 5, and 7).

Accordingly, one embodiment of the present invention relates to native promoters comprising polynucleotides isolated from *C. glutamicum*, and mutant promoters derived therefrom that together represent a ladder of constitutive promoters with incrementally increasing levels of promoter activity. In some embodiments a *C. glutamicum* promoter can be encoded by a short DNA sequence. In some embodiments a *C. glutamicum* promoter can be encoded by a DNA sequence of less than 100 base pairs.

One embodiment of the present invention relates to a promoter polynucleotide comprising a sequence selected from: SEQ ID NO:1 (Pcg0007_lib_39), SEQ ID NO:2 (Pcg1860), SEQ ID NO:3 (Pcg0007), SEQ ID NO:4 (Pcg0755), SEQ ID NO:5 (Pcg0007_lib_265), SEQ ID NO:6 (Pcg3381), SEQ ID NO:7 (Pcg0007_lib_119), or SEQ ID NO:8 (Pcg3121). In another embodiment, the present specification provides for, and includes, a promoter polynucleotide comprising of SEQ ID NO:1 functionally linked to at least one heterologous target gene. In an embodiment, the present specification provides for, and includes, a promoter polynucleotide of SEQ ID NO:2 functionally linked to at least one heterologous target gene. In another embodiment, the present specification provides for, and includes, a promoter polynucleotide of SEQ ID NO:3 functionally linked to at least one heterologous target gene. In another embodiment, the present specification provides for, and includes, a promoter polynucleotide of SEQ ID NO:4 functionally linked to at least one heterologous target gene. In another embodiment, the present specification provides for, and includes, a promoter polynucleotide of SEQ ID NO:5 functionally linked to at least one heterologous target gene. In another embodiment, the present specification provides for, and includes, a promoter polynucleotide comprising of SEQ ID NO:5 functionally linked to at least one heterologous target gene. In another embodiment, the present specification provides for, and includes, a promoter polynucleotide of SEQ ID NO:7 functionally linked to at least one heterologous target gene. In another embodiment, the present specification provides for, and includes, a promoter polynucleotide of SEQ ID NO:8 functionally linked to at least one heterologous target gene.

As used herein, a "promoter cassette" refers to the polynucleotide sequences comprising a promoter polynucleotide of SEQ ID NOs:1 to 8 functionally linked to at least one heterologous target gene. In certain embodiments of the present disclosure, a "promoter cassette" may further include one or more of a linker polynucleotide, a transcription terminator following the heterologous gene, a ribosome binding site upstream of the start codon of the heterologous gene, and combinations of each. One embodiment of the present invention relates to a promoter polynucleotide consisting of a sequence selected from: SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In an embodiment, the present specification provides for, and includes a promoter polynucleotide sequence of SEQ ID NO:1. In an embodiment, the present specification provides for, and includes a promoter polynucleotide sequence of SEQ ID NO:5. In an embodiment, the present specification provides for, and includes a promoter polynucleotide sequence of SEQ ID NO:7. As used herein a promoter cassette may described by reference the promoter name followed by the name of the heterologous target gene that is functionally linked to it. For example, the promoter of SEQ ID NO: 1, entitled Pcg1860, functionally lithe to the gene zwf encoding the glucose-6-phosphate 1-dehydrogenase gene is referenced as Pcg1860-zwf. Similarly, Pcg0007_39-lysA is the 0007_39 promoter of SEQ ID NO:1 functionally linked to target gene lysA encoding the polypeptide diaminopimelate decarboxylase.

One embodiment of the present invention relates to combinations of the promoter polynucleotides described herein. In this context the term "combinations of promoter polynucleotides" refers to two or more polynucleotides that may be present as separate isolated sequences, as components of separate polynucleotide molecules, or as components of the same polynucleotide molecule, and combinations thereof. Examples of polynucleotide molecules include chromosomes and plasmids.

The invention also relates to an isolated promoter polynucleotide, which essentially consists of a polynucleotide having the nucleotide sequence depicted in SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In an embodiment, the present specification provides for, and includes an isolated promoter polynucleotide of SEQ ID NO:1. In an embodiment, the present specification provides for, and includes an isolated promoter polynucleotide of SEQ ID NO:5. In an embodiment, the present specification provides for, and includes an isolated promoter polynucleotide of SEQ ID NO:7.

The term "essentially" in this context means that a polynucleotide of no more than 1,000, no more than 800, no more than 700, no more than 600, no more than 500 or no more than 400 nucleotides in length; and a polynucleotide of no more than 15,000, no more than 10,000, no more than 7,500, no more than 5,000, no more than 2,500, no more than 1,000, no more than 800, no more than 700, no more than 600, no more than 500, or no more than 400 nucleotides in length have been added to the 5' end and 3' end, respectively, of the polynucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Any useful combination of the features from the preceding two lists of polynucleotides added to the 5' end and 3' end, respectively, of the polynucleotides of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, is in accordance with the invention here. "Useful combination" means, for example, a combination of features which results in an efficient recombination being carried out. The use of additions of the same length flanking a DNA region to be replaced facilitates the transfer of the region by homologous recombination in the experimental procedure. Relatively long flanking homologous regions are advantageous for efficient recombination between circular DNA molecules but cloning of the replacement vector is made more difficult with increasing length of the flanks (Wang et al., Molecular Biotechnology, 432:43-53 (2006)). The specification provides for, and includes, homologous regions flanking a promoter polynucleotide sequence of SEQ ID NOs:1 to 8 functionally linked to at least on heterologous target gene (e.g., the "promoter cassette") to direct homologous recombination and replacement of a target gene sequence. In an embodiment, the homologus regions are direct repeat regions. In an embodiment, the homologous regions comprises between 500 base pairs (bp) and 5000 bp each of the target gene sequence flanking the promoter cassette. In an embodiment, the homologous regions comprises at least 500 bp each of the target gene sequence flanking the promoter cassette. In an embodiment, the homologous regions comprises at least 1000 bp (1 Kb) each of the target gene sequence flanking the promoter cassette. In an embodiment, the homologous regions comprises at least 2 Kb each of the target gene sequence flanking the promoter cassette. In an embodiment, the homologous regions comprises at least 5 Kb each of the target gene sequence flanking the promoter cassette.

The invention furthermore relates to an isolated promoter polynucleotide, which consists of the nucleotide sequence depicted in SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In an embodiment, the isolate promoter polynucleotide consists of the polynucleotide sequence of SEQ ID NO:1. In an embodiment, the isolate promoter polynucleotide consists of the polynucleotide sequence of SEQ ID NO:5. In an embodiment, the isolate promoter polynucleotide consists of the polynucleotide sequence of SEQ ID NO:7.

Details regarding the biochemistry and chemical structure of polynucleotides as present in living things such as microorganisms, for example, can be found inter alia in the text book "Biochemie" [Biochemistry] by Berg et al. (Spektrum Akademischer Verlag Heidelberg Berlin, Germany, 2003; ISBN 3-8274-1303-6).

Polynucleotides consisting of deoxyribonucleotide monomers containing the nucleobases or bases adenine (A), guanine (G), cytosine (C) and thymine (T) are referred to as deoxyribo-polynucleotides or deoxyribonucleic acid (DNA). Polynucleotides consisting of ribonucleotide monomers containing the nucleobases or bases adenine (A), guanine (G), cytosine (C) and uracil (U) are referred to as ribopolynucleotides or ribonucleic acid (RNA). The monomers in said polynucleotides are covalently linked to one another by a 3',5'-phosphodiester bond.

A "promoter polynucleotide" or a "promoter" or a "polynucleotide having promoter activity" means a polynucleotide, preferably deoxyribopolynucleotide, or a nucleic acid, preferably deoxyribonucleic acid (DNA), which when functionally linked to a polynucleotide to be transcribed determines the point and frequency of initiation of transcription of the coding polynucleotide, thereby enabling the strength of expression of the controlled polynucleotide to be influenced. The term "promoter ladder" as used herein refers to a plurality of promoters with incrementally increasing levels of promoter activity. The term "promoter activity" as used herein refers to the ability of the promoter to initiate transcription of an polynucleotide sequence into mRNA. Methods of assessing promoter activity are well known to those of skill in the art and include, for example the methods described in Example 2 below. The term "constitutive promoter" as used herein refers to a promoter that directs the transcription of tits associated genes at a constant rate regardless of the internal or external cellular conditions.

Owing to the double-stranded structure of DNA, the strand complementary to the strand in SEQ ID NO:1, SEQ ID NO:2, SEQ ID NO:3, SEQ ID NO:4, SEQ ID NO:5, SEQ ID NO:6, SEQ ID NO:7, or SEQ ID NO:8 of the sequence listing is likewise a subject of the invention.

Kits

One embodiment of the present invention relates to kits comprising a first promoter polynucleotide comprising a sequence selected from: SEQ ID NO:1, SEQ ID NO:5, and SEQ ID NO:7, and a suitable storage means for the polynucleotide. In some embodiments, the first promoter polynucleotide consists of a sequence selected from: SEQ ID NO:1, SEQ ID NO:5, and SEQ ID NO:7. In some embodiments, the kits comprise combinations of promoter polynucleotides comprising at least two first promoter polynucleotides described herein. In some embodiments, the kits comprise combinations of promoter polynucleotides comprising at least one first promoter polynucleotide described herein, and at least one second promoter polynucleotide comprising a sequence selected from: SEQ ID NO:2, SEQ ID NO:3, SEQ ID NO:4, SEQ ID NO:6, and SEQ ID NO:8. In some embodiments, the kits comprise combinations of promoter polynucleotides comprising at least one first promoter polynucleotide described herein, and at least one second promoter polynucleotide consisting of a sequence selected from: SEQ ID NO:2, SEQ ID NO:3, SEQ ID NO:4, SEQ ID NO:6, and SEQ ID NO:8.

Target Genes

One embodiment of the present invention relates to methods of expressing a target gene, comprising culturing a host cell transformed with a recombinant vector comprising a promoter polynucleotide as described herein. Target genes are polynucleotides the expression of which are controlled by the promoters described herein. The target genes may be coding polynucleotides which code for one or more polypeptide(s) or non-coding polynucleotides such as non-coding RNAs. A polynucleotide coding for a protein/polypeptide essentially consists of a start codon selected from the group consisting of ATG, GTG and TTG, preferably ATG or GTG, particularly preferably ATG, a protein-encoding sequence and one or more stop codon(s) selected from the group consisting of TAA, TAG and TGA.

"Transcription" means the process by which a complementary RNA molecule is produced starting from a DNA template. This process involves proteins such as RNA polymerase, "sigma factors" and transcriptional regulatory proteins. Where the target gene is a coding polynucleotide, the synthesized RNA (messenger RNA, mRNA) then serves as a template in the process of translation which subsequently yields the polypeptide or protein.

"Functionally linked" means in this context the sequential arrangement of the promoter polynucleotide according to the invention with a further oligo- or polynucleotide, resulting in transcription of said further polynucleotide to produce a sense RNA transcript.

If the further polynucleotide is a target gene which codes for a polypeptide/protein and consists of the coding region for a polypeptide, starting with a start codon, including the stop codon and, where appropriate, including a transcription termination sequence, "functionally linked" then means the sequential arrangement of the promoter polynucleotide according to the invention with the target gene, resulting in transcription of said target gene and translation of the synthesized RNA.

If the target gene codes for a plurality of proteins/polypeptides, each gene may be preceded by a ribosome-binding site. Where appropriate, a termination sequence is located downstream of the last gene.

The target gene preferably codes for one or more polypeptides or proteins of the biosynthetic pathway of biomolecules, preferably selected from the group of proteinogenic amino acids, non-proteinogenic amino acids, vitamins, nucleosides, nucleotides and organic acids. The target gene preferably consists of one or more of the polynucleotides listed in Table 1 of EP 1 108 790 A2 which is hereby incorporated by reference.

The present specification provides for, and includes, recombinant nucleic acid molecules comprising a promoter polynucleotide sequence selected from the group consisting of SEQ ID NOs:1 to 8 functionally linked to any one of the heterologous target genes identifiable in the Kyoto Encyclopedia of Genes and Genomes (KEGG) as genes involved in metabolic and biosynthetic pathways. The KEGG database is available on the internet at genome.jp/kegg. In an embodiment, the promoter polynucleotide sequences of SEQ ID NOs:1 to 8 are functionally linked to one or more target genes of the lysine biosynthesis pathway as represented in KEGG map number 00300. In an embodiment, the one or more target genes are selected from the Lysine succinyl-DAP biosynthesis pathway, M00016. In an embodiment, the one or more target genes are selected from the lysine acetyl-DAP biosynthesis pathway, M00525. In an embodiment, the one or more target genes are selected from the lysine DAP dehydrogenase biosynthesis pathway, M00526. In an embodiment, the one or more target genes are selected from the lysine DAP aminotransferase biosynthesis pathway, M00527. In an embodiment, the one or more target genes are selected from the AAA pathway biosynthesis pathway, M00030. In an embodiment, the one or more target genes are selected from the lysine biosynthesis pathway from 2-oxoglutarate, M00433 or the lysine biosynthesis pathway mediated by LysW, M00031.

The present disclosure provides for, and includes, the promoter polynucleotide sequences of SEQ ID NOs:1 to 8 are functionally linked to one or more target genes of the the serine biosynthesis pathway comprising genes of entry M00020. In an embodiment, the promoter polynucleotide sequences of SEQ ID NOs:1 to 8 are functionally linked to one or more target genes of the threonine biosynthesis pathway comprising genes of KEGG entry M00018. In an embodiment, the promoter polynucleotide sequences of SEQ ID NOs:1 to 8 are functionally linked to one or more target genes of the cysteine biosynthesis pathway comprising genes of KEGG entry M00021. In an embodiment, the promoter polynucleotide sequences of SEQ ID NOs:1 to 8 are functionally linked to one or more target genes of the cysteine biosynthesis pathway comprising genes of KEGG entry M00338. In an embodiment, the promoter polynucleotide sequences of SEQ ID NOs:1 to 8 are functionally linked to one or more target genes of the cysteine biosynthesis pathway comprising genes of KEGG entry M00609. In an embodiment, the promoter polynucleotide sequences of SEQ ID NOs:1 to 8 are functionally linked to one or more target genes of the methionine biosynthesis pathway comprising genes of KEGG entry M00017. In an embodiment, the promoter polynucleotide sequences of SEQ ID NOs:1 to 8 are functionally linked to one or more target genes of the valine/isoleucine biosynthesis pathway comprising genes of KEGG entry M00019. In an embodiment, the promoter polynucleotide sequences of SEQ ID NOs:1 to 8 are functionally linked to one or more target genes of the isoleucine biosynthesis pathway comprising genes of KEGG entry M00535. In an embodiment, the promoter polynucleotide sequences of SEQ ID NOs:1 to 8 are functionally linked to one or more target genes of the isoleucine biosynthesis pathway comprising genes of KEGG entry M00570. In an embodiment, the promoter polynucleotide sequences of SEQ ID NOs:1 to 8 are functionally linked to one or more target genes of the leucine biosynthesis pathway comprising genes of KEGG entry M00432. In an embodiment, the promoter polynucleotide sequences of SEQ ID NOs:1 to 8 are functionally linked to one or more target genes of the proline biosynthesis pathway comprising genes of KEGG entry M00015. In an embodiment, the promoter polynucleotide sequences of SEQ ID NOs:1 to 8 are functionally linked to one or more target genes of the ornithine biosynthesis pathway comprising genes of KEGG entry M00028. In an embodiment, the promoter polynucleotide sequences of SEQ ID NOs:1 to 8 are functionally linked to one or more target genes of the ornithine biosynthesis pathway comprising genes of KEGG entry M00763. In an embodiment, the promoter polynucleotide sequences of SEQ ID NOs:1 to 8 are functionally linked to one or more target genes of the histidine biosynthesis pathway comprising genes of KEGG entry M00026. In an embodiment, the promoter polynucleotide sequences of SEQ ID NOs:1 to 8 are functionally linked to one or more target genes of the shikimate biosynthesis pathway comprising genes of KEGG entry M00022. In an embodiment, the promoter polynucleotide sequences of SEQ ID NOs:1 to 8 are functionally linked to one or more target genes of the tryptophan biosynthesis pathway comprising genes of entry M00023. In an embodiment, the promoter polynucleotide sequences of SEQ ID NOs:1 to 8 are functionally linked to one or more target genes of the phenylalanine biosynthesis pathway comprising genes of KEGG entry M00024. In an embodiment, the promoter polynucleotide sequences of SEQ ID NOs:1 to 8 are functionally linked to one or more target genes of the tyrosine biosynthesis pathway comprising genes of KEGG entry M00025. In an embodiment, the promoter polynucleotide sequences of SEQ ID NOs:1 to 8 are functionally linked to one or more target genes of the tyrosine biosynthesis pathway comprising genes of KEGG entry M00040.

The present disclosure provides for, and includes, the promoter polynucleotide sequences of SEQ ID NOs:1, 5 or 7 are functionally linked to one or more target genes of the the serine biosynthesis pathway comprising genes of entry M00020. In an embodiment, the promoter polynucleotide sequences of SEQ ID NOs:1, 5 or 7 are functionally linked to one or more target genes of the threonine biosynthesis pathway comprising genes of KEGG entry M00018. In an embodiment, the promoter polynucleotide sequences of SEQ ID NOs:1, 5 or 7 are functionally linked to one or more target genes of the cysteine biosynthesis pathway comprising genes of KEGG entry M00021. In an embodiment, the promoter polynucleotide sequences of SEQ ID NOs:1, 5 or 7 are functionally linked to one or more target genes of the cysteine biosynthesis pathway comprising genes of KEGG entry M00338. In an embodiment, the promoter polynucleotide sequences of SEQ ID NOs:1, 5 or 7 are functionally linked to one or more target genes of the cysteine biosynthesis pathway comprising genes of KEGG entry M00609. In an embodiment, the promoter polynucleotide sequences of SEQ ID NOs:1, 5 or 7 are functionally linked to one or more target genes of the methionine biosynthesis pathway comprising genes of KEGG entry M00017. In an embodiment, the promoter polynucleotide sequences of SEQ ID NOs:1, 5 or 7 are functionally linked to one or more target genes of the valine/isoleucine biosynthesis pathway comprising genes of KEGG entry M00019. In an embodiment, the promoter polynucleotide sequences of SEQ ID NOs:1, 5 or 7 are functionally linked to one or more target genes of the isoleucine biosynthesis pathway comprising genes of KEGG entry M00535. In an embodiment, the promoter polynucleotide sequences of SEQ ID NOs:1, 5 or 7 are functionally linked to one or more target genes of the isoleucine biosynthesis pathway comprising genes of KEGG entry M00570. In an embodiment, the promoter polynucleotide sequences of SEQ ID NOs:1, 5 or 7 are functionally linked to one or more target genes of the leucine biosynthesis pathway comprising genes of KEGG entry M00432. In an embodiment, the promoter polynucleotide sequences of SEQ ID NOs:1, 5 or 7 are functionally linked to one or more target genes of the proline biosynthesis pathway comprising genes of KEGG entry M00015. In an embodiment, the promoter polynucleotide sequences of SEQ ID NOs:1, 5 or 7 are functionally linked to one or more target genes of the ornithine biosynthesis pathway comprising genes of KEGG entry M00028. In an embodiment, the promoter polynucleotide sequences of SEQ ID NOs:1, 5 or 7 are functionally linked to one or more target genes of the ornithine biosynthesis pathway comprising genes of KEGG entry M00763. In an embodiment, the promoter polynucleotide sequences of SEQ ID NOs:1, 5 or 7 are functionally linked to one or more target genes of the histidine biosynthesis pathway comprising genes of KEGG entry M00026. In an embodiment, the promoter polynucleotide sequences of SEQ ID NOs:1, 5 or 7 are functionally linked to one or more target genes of the shikimate biosynthesis pathway comprising genes of KEGG entry M00022. In an embodiment, the promoter polynucleotide sequences of SEQ ID NOs:1, 5 or 7 are functionally linked to one or more target genes of the tryptophan biosynthesis pathway comprising genes of entry M00023. In an embodiment, the promoter polynucleotide sequences of SEQ ID NOs:1, 5 or 7 are functionally linked to one or more target genes of the phenylalanine biosynthesis pathway comprising genes of KEGG entry M00024. In an embodiment, the promoter polynucleotide sequences of SEQ ID NOs:1, 5 or 7 are functionally linked to one or more target genes of the tyrosine biosynthesis pathway comprising genes of KEGG entry M00025. In an embodiment, the promoter polynucleotide sequences of SEQ ID NOs:1, 5 or 7 are functionally linked to one or more target genes of the tyrosine biosynthesis pathway comprising genes of KEGG entry M00040.

The present specification provides for, and includes, recombinant nucleic acid molecules comprising a promoter polynucleotide sequence selected from the group consisting of SEQ ID NOs:1 to 8 functionally linked to any one of the heterologous target genes from *Corynebacterium glutamicum* ATCC 13032 provided in Table 2 or any *Corynebacterium glutamicum* equivalent thereof. Sequence start and end positions correspond to genomic nucleotide accession NC_003450.3. It will be understood by those of ordinary skill in the art that corresponding genes exist in other strains of *C. glutamicum* and may be readily identified from Table 2. In an embodiment, the present specification provides for, and includes a recombinant nucleic acid molecule comprising a promoter polynucleotide sequence of SEQ ID NO:1 functionally linked to a heterologous target gene recited in Table 2. In an embodiment, the present specification provides for, and includes a recombinant nucleic acid molecule comprising a promoter polynucleotide sequence of SEQ ID NO:2 functionally linked to a heterologous target gene recited in Table 2. In an embodiment, the present specification provides for, and includes a recombinant nucleic acid molecule comprising a promoter polynucleotide sequence of SEQ ID NO:3 functionally linked to a heterologous target gene recited in Table 2. In an embodiment, the present specification provides for, and includes a recombinant nucleic acid molecule comprising a promoter polynucleotide sequence of SEQ ID NO:4 functionally linked to a heterologous target gene recited in Table 2. In an embodiment, the present specification provides for, and includes a recombinant nucleic acid molecule comprising a promoter polynucleotide sequence of SEQ ID NO:5 functionally linked to a heterologous target gene recited in Table 2. In an embodiment, the present specification provides for, and includes a recombinant nucleic acid molecule comprising a promoter polynucleotide sequence of SEQ ID NO:6 functionally linked to a heterologous target gene recited in Table 2. In an embodiment, the present specification provides for, and includes a recombinant nucleic acid molecule comprising a promoter polynucleotide sequence of SEQ ID NO:7 functionally linked to a heterologous target gene recited in Table 2. In an embodiment, the present specification provides for, and includes a recombinant nucleic acid molecule comprising a promoter polynucleotide sequence of SEQ ID NO:8 functionally linked to a heterologous target gene recited in Table 2.

TABLE 2

Target genes from *Corynebacterium glutamicum* according to the present specification

| Gene ID | Symbol | Aliases | description | start | end | orientation |
|---|---|---|---|---|---|---|
| 1021315 | NCgl0248 | NCgl0248, Cgl0252 | aspartate-semialdehyde dehydrogenase | 270660 | 271694 | plus |
| 1021300 | NCgl0223 | NCgl0223, Cgl0226 | prephenate dehydrogenase | 241880 | 242902 | minus |
| 1021294 | NCgl0247 | NCgl0247, Cgl0251 | aspartate kinase | 269371 | 270636 | plus |
| 1021282 | NCgl0215 | NCgl0215, Cgl0218 | aminotransferase | 232257 | 233282 | minus |
| 1021250 | NCgl0181 | NCgl0181, Cgl0184 | glutamine 2-oxoglutarate aminotransferase large subunit | 195240 | 199772 | plus |
| 1021247 | gltD | NCgl0182, Cgl0185 | glutamate synthase | 199772 | 201292 | plus |
| 1021203 | aroE | NCgl0409, Cgl0424 | quinate/shikimate dehydrogenase | 446538 | 447389 | plus |
| 1021149 | NCgl0245 | NCgl0245, Cgl0248 | 2-isopropylmalate synthase | 266151 | 267896 | minus |
| 1021136 | gpmA | NCgl0390, Cgl0402 | 2,3-bisphosphoglycerate-dependent phosphoglycerate mutase | 425177 | 425923 | plus |
| 1021131 | NCgl0408 | NCgl0408, Cgl0423 | 3-dehydroquinate dehydratase | 446087 | 446524 | plus |
| 1021078 | NCgl0398 | NCgl0398, Cgl0410 | pyrroline-5-carboxylate reductase | 434877 | 435698 | plus |
| 1020978 | trpA | NCgl2932, Cgl3035 | tryptophan synthase subunit alpha | 3239333 | 3240175 | plus |
| 1020976 | NCgl2931 | NCgl2931, Cgl3034 | tryptophan synthase subunit beta | 3238083 | 3239336 | plus |
| 1020975 | NCgl2930 | NCgl2930, trpC, trpF | bifunctional indole-3-glycerol phosphate synthase/phosphoribosyl-anthranilate isomerase | 3236642 | 3238066 | plus |
| 1020974 | trpD | NCgl2929, Cgl3032 | anthranilate phosphoribosyltransferase | 3235603 | 3236649 | plus |
| 1020973 | NCgl2928 | NCgl2928, Cgl3031 | anthranilate synthase II | 3234957 | 3235583 | plus |
| 1020972 | NCgl2927 | NCgl2927, Cgl3029 | anthranilate synthase I | 3233404 | 3234960 | plus |
| 1020852 | NCgl2809 | NCgl2809, Cgl2910 | pyruvate kinase | 3110462 | 3112321 | minus |
| 1020842 | NCgl2799 | NCgl2799, Cgl2899 | prephenate dehydratase | 3098576 | 3099523 | minus |
| 1020841 | NCgl2798 | NCgl2798, Cgl2898 | phosphoglycerate mutase | 3097902 | 3098573 | minus |
| 1020788 | NCgl2747 | NCgl2747, Cgl2844 | aminotransferase | 3030670 | 3031983 | plus |
| 1020745 | NCgl2704 | NCgl2704, Cgl2802 | nucleosidase | 2988212 | 2988772 | minus |
| 1020729 | NCgl2688 | NCgl2688, Cgl2786 | cystathionine gamma-synthase | 2972058 | 2973206 | minus |
| 1020714 | NCgl2673 | NCgl2673, Cgl2770 | fructose-bisphosphate aldolase | 2954239 | 2955273 | minus |
| 1020594 | NCgl2557 | NCgl2557, Cgl2646 | dihydrodipicolinate synthase | 2815459 | 2816397 | plus |
| 1020564 | NCgl2528 | NCgl2528, Cgl2617 | D-2-hydroxyisocaproate dehydrogenase | 2786754 | 2787716 | minus |
| 1020509 | NCgl2474 | NCgl2474, Cgl2563 | serine acetyltransferase | 2723065 | 2723613 | plus |
| 1020508 | NCgl2473 | NCgl2473, Cgl2562 | cysteine synthase | 2721905 | 2722861 | plus |
| 1020471 | NCgl2436 | NCgl2436, Cgl2522 | phosphoserine phosphatase | 2669555 | 2670856 | minus |
| 1020393 | NCgl2360 | NCgl2360, Cgl2446 | cystathionine gamma-synthase | 2590310 | 2591470 | minus |
| 1020370 | NCgl2337 | NCgl2337, Cgl2423 | ribose-5-phosphate isomerase B | 2563930 | 2564403 | minus |
| 1020307 | NCgl2274 | NCgl2274, Cgl2356 | gamma-glutamyl kinase | 2496668 | 2497777 | minus |

TABLE 2-continued

Target genes from *Corynebacterium glutamicum* according to the present specification

| Gene ID | Symbol | Aliases | description | start | end | orientation |
|---|---|---|---|---|---|---|
| 1020305 | proA | NCgl2272, Cgl2354 | gamma-glutamyl phosphate reductase | 2494337 | 2495635 | minus |
| 1020301 | NCgl2268 | NCgl2268, Cgl2350 | fructose-2,6-bisphosphatase | 2491149 | 2491859 | minus |
| 1020260 | NCgl2227 | NCgl2227, Cgl2309 | PLP-dependent aminotransferase | 2444607 | 2445713 | plus |
| 1020188 | NCgl2155 | NCgl2155, Cgl2236 | bifunctional RNase H/acid phosphatase | 2371410 | 2372558 | minus |
| 1020181 | NCgl2148 | NCgl2148, Cgl2229 | glutamine synthase | 2362816 | 2364156 | minus |
| 1020172 | NCgl2139 | NCgl2139, Cgl2220 | threonine synthase | 2353598 | 2355043 | minus |
| 1020166 | NCgl2133 | NCgl2133, Cgl2214 | glutamine synthase | 2348830 | 2350263 | plus |
| 1020155 | NCgl2123 | NCgl2123, Cgl2204 | branched-chain amino acid aminotransferase | 2335913 | 2337016 | minus |
| 1020130 | NCgl2098 | NCgl2098, Cgl2178 | 3-deoxy-7-phosphoheptulonate synthase | 2307695 | 2309095 | minus |
| 1020087 | NCgl2055 | NCgl2055, Cgl2136 | cysteine synthase | 2258360 | 2259313 | minus |
| 1020086 | NCgl2054 | NCgl2054, Cgl2135 | diaminopimelate decarboxylase | 2255736 | 2257025 | minus |
| 1020080 | NCgl2048 | NCgl2048, Cgl2129 | methionine synthase II | 2247004 | 2248209 | minus |
| 1020078 | NCgl2046 | NCgl2046, Cgl2127 | threonine dehydratase | 2244862 | 2246172 | minus |
| 1020053 | hisD | NCgl2021, Cgl2102 | histidinol dehydrogenase | 2217597 | 2218925 | minus |
| 1020052 | NCgl2020 | NCgl2020, Cgl2101 | histidinol-phosphate aminotransferase | 2216491 | 2217591 | minus |
| 1020051 | hisB | NCgl2019, Cgl2100 | imidazoleglycerol-phosphate dehydratase | 2215866 | 2216474 | minus |
| 1020048 | hisH | NCgl2016, Cgl2097 | imidazole glycerol phosphate synthase subunit HisH | 2212638 | 2213273 | minus |
| 1020047 | NCgl2015 | NCgl2015, Cgl2096 | phosphoribosyl isomerase A | 2211879 | 2212619 | minus |
| 1020045 | hisF | NCgl2013, Cgl2094 | imidazole glycerol phosphate synthase subunit HisF | 2210270 | 2211046 | minus |
| 1020044 | hisI | NCgl2012, Cgl2093 | phosphoribosyl-AMP cyclohydrolase | 2209917 | 2210273 | minus |
| 1020042 | NCgl2010 | NCgl2010, Cgl2091 | indole-3-glycerol phosphate synthase | 2208364 | 2209149 | minus |
| 1020040 | NCgl2008 | NCgl2008, Cgl2089 | pyruvate kinase | 2205665 | 2207092 | minus |
| 1019930 | NCgl1898 | NCgl1898, Cgl1973 | 4-hydroxy-tetrahydrodipicolinate reductase | 2081188 | 2081934 | minus |
| 1019928 | dapA | NCgl1896, Cgl1971 | 4-hydroxy-tetrahydrodipicolinate synthase | 2079278 | 2080183 | minus |
| 1019900 | dapF | NCgl1868, Cgl1943 | diaminopimelate epimerase | 2051842 | 2052675 | minus |
| 1019614 | NCgl1583 | NCgl1583, Cgl1645 | L-serine deaminase | 1744884 | 1746233 | plus |
| 1019598 | aroE | NCgl1567, Cgl1629 | shikimate 5-dehydrogenase | 1724609 | 1725439 | minus |
| 1019592 | NCgl1561 | NCgl1561, Cgl1623 | chorismate synthase | 1719666 | 1720898 | minus |
| 1019591 | aroK | NCgl1560, Cgl1622 | shikimate kinase | 1719104 | 1719676 | minus |
| 1019590 | aroB | NCgl1559, Cgl1621 | 3-dehydroquinate synthase | 1717935 | 1719032 | minus |
| 1019571 | NCgl1541 | NCgl1541, Cgl1603 | methionine adenosyltransferase | 1699174 | 1700397 | minus |
| 1019566 | NCgl1536 | NCgl1536, Cgl1598 | ribulose-phosphate 3-epimerase | 1693259 | 1693918 | minus |
| 1019556 | NCgl1526 | NCgl1526, Cgl1588 | glyceraldehyde-3-phosphate dehydrogenase | 1682621 | 1683625 | minus |
| 1019555 | Pgk | NCgl1525, Cgl1587 | phosphoglycerate kinase | 1681187 | 1682404 | minus |
| 1019554 | tpiA | NCgl1524, Cgl1586 | triosephosphate isomerase | 1680329 | 1681108 | minus |

TABLE 2-continued

Target genes from *Corynebacterium glutamicum* according to the present specification

| Gene ID | Symbol | Aliases | description | start | end | orientation |
|---|---|---|---|---|---|---|
| 1019550 | NCgl1520 | NCgl1520, Cgl1582 | ornithine cyclodeaminase | 1674120 | 1675268 | minus |
| 1019543 | NCgl1513 | NCgl1513, Cgl1575 | transaldolase | 1666673 | 1667755 | plus |
| 1019542 | NCgl1512 | NCgl1512, Cgl1574 | transketolase | 1664403 | 1666505 | plus |
| 1019512 | NCgl1482 | NCgl1482, Cgl1540 | aconitate hydratase | 1626279 | 1629110 | plus |
| 1019480 | NCgl1450 | NCgl1450, Cgl1507 | methionine synthase I cobalamin-binding subunit | 1587570 | 1591235 | minus |
| 1019478 | hisE | NCgl1448, Cgl1505 | phosphoribosyl-ATP pyrophosphatase | 1586462 | 1586725 | minus |
| 1019477 | hisG | NCgl1447, Cgl1504 | ATP phosphoribosyltransferase | 1585600 | 1586445 | minus |
| 1019377 | NCgl1347 | NCgl1347, Cgl1401 | argininosuccinate lyase | 1471477 | 1472910 | plus |
| 1019376 | NCgl1346 | NCgl1346, Cgl1400 | argininosuccinate synthase | 1470211 | 1471416 | plus |
| 1019374 | NCgl1344 | NCgl1344, Cgl1398 | ornithine carbamoyltransferase | 1468565 | 1469524 | plus |
| 1019373 | argD | NCgl1343, Cgl1397 | acetylornithine aminotransferase | 1467376 | 1468551 | plus |
| 1019372 | NCgl1342 | NCgl1342, Cgl1396 | acetylglutamate kinase | 1466422 | 1467375 | plus |
| 1019371 | argJ | NCgl1341, Cgl1395 | bifunctional ornithine acetyltransferase/N-acetylglutamate synthase | 1465210 | 1466376 | plus |
| 1019370 | argC | NCgl1340, Cgl1394 | N-acetyl-gamma-glutamyl-phosphate reductase | 1464053 | 1465126 | plus |
| 1019293 | leuD | NCgl1263, Cgl1316 | 3-isopropylmalate dehydratase small subunit | 1381902 | 1382495 | plus |
| 1019292 | NCgl1262 | NCgl1262, Cgl1315 | 3-isopropylmalate dehydratase large subunit | 1380440 | 1381885 | plus |
| 1019267 | NCgl1237 | NCgl1237, Cgl1286 | 3-isopropylmalate dehydrogenase | 1353489 | 1354511 | plus |
| 1019265 | NCgl1235 | NCgl1235, Cgl1284 | D-3-phosphoglycerate dehydrogenase | 1350855 | 1352447 | plus |
| 1019254 | NCgl1224 | NCgl1224, Cgl1273 | ketol-acid reductoisomerase | 1340724 | 1341740 | plus |
| 1019253 | ilvH | NCgl1223, Cgl1272 | acetolactate synthase small subunit | 1340025 | 1340543 | plus |
| 1019252 | NCgl1222 | NCgl1222, Cgl1271 | acetolactate synthase large subunit | 1338131 | 1340011 | plus |
| 1019249 | NCgl1219 | NCgl1219, Cgl1268 | dihydroxy-acid dehydratase | 1333439 | 1335280 | minus |
| 1019232 | NCgl1202 | NCgl1202, Cgl1250 | 6-phosphofructokinase | 1315046 | 1316086 | plus |
| 1019167 | NCgl1137 | NCgl1137, Cgl1184 | homoserine kinase | 1243855 | 1244784 | plus |
| 1019166 | NCgl1136 | NCgl1136, Cgl1183 | homoserine dehydrogenase | 1242507 | 1243844 | plus |
| 1019163 | NCgl1133 | NCgl1133, Cgl1180 | diaminopimelate decarboxylase | 1239929 | 1241266 | plus |
| 1019124 | NCgl1094 | NCgl1094, Cgl1139 | 5-methyltetrahydropteroyl-triglutamate--homocysteine S-methyltransferase | 1188385 | 1190622 | minus |
| 1019117 | aroE | NCgl1087, Cgl1132 | shikimate 5-dehydrogenase | 1180869 | 1181675 | minus |
| 1019094 | NCgl1064 | NCgl1064, Cgl1109 | succinyl-diaminopimelate desuccinylase | 1155731 | 1156840 | plus |
| 1019093 | NCgl1063 | NCgl1063, Cgl1108 | tetrahydrodipicolinate N-succinyltransferase | 1154726 | 1155676 | minus |
| 1019091 | NCgl1061 | NCgl1061, Cgl1106 | 2,3,4,5-tetrahydropyridine-2,6-dicarboxylate N-succinyltransferase | 1152370 | 1153263 | minus |
| 1019042 | NCgl1013 | NCgl1013, Cgl1058 | phosphoglycerate mutase | 1107503 | 1108204 | plus |
| 1018983 | glyA | NCgl0954, Cgl0996 | serine hydroxymethyltransferase | 1050624 | 1051928 | plus |
| 1018979 | NCgl0950 | NCgl0950, Cgl0990 | phospho-2-dehydro-3-deoxyheptonate aldolase | 1046610 | 1047710 | plus |
| 1018968 | NCgl0939 | NCgl0939, Cgl0978 | threonine dehydratase | 1038718 | 1039650 | minus |

TABLE 2-continued

Target genes from *Corynebacterium glutamicum* according to the present specification

| Gene ID | Symbol | Aliases | description | start | end | orientation |
|---|---|---|---|---|---|---|
| 1018964 | eno | NCgl0935, Cgl0974 | phosphopyruvate hydratase | 1034949 | 1036226 | plus |
| 1018934 | NCgl0905 | NCgl0905, Cgl0942 | ribose-phosphate pyrophosphokinase | 997463 | 998440 | minus |
| 1018929 | NCgl0900 | NCgl0900, Cgl0937 | glyceraldehyde-3-phosphate dehydrogenase | 993174 | 994616 | plus |
| 1018848 | NCgl0819 | NCgl0819, Cgl0853 | hypothetical protein | 910852 | 911157 | minus |
| 1018824 | gltA | NCgl0795, Cgl0829 | type II citrate synthase | 877838 | 879151 | plus |
| 1018823 | NCgl0794 | NCgl0794, Cgl0828 | phosphoserine aminotransferase | 875982 | 877112 | minus |
| 1018809 | NCgl0780 | NCgl0780, Cgl0814 | aminotransferase | 861592 | 862755 | plus |
| 1018794 | NCgl0765 | NCgl0765, Cgl0799 | fructose-1,6-bisphosphatase | 841514 | 842296 | minus |
| 1018759 | NCgl0730 | NCgl0730, Cgl0764 | 3-phosphoshikimate 1-carboxyvinyltransferase | 801187 | 802479 | minus |
| 1018688 | NCgl0659 | NCgl0659, Cgl0689 | pyruvate carboxylase | 705211 | 708633 | plus |
| 1018663 | NCgl0634 | NCgl0634, Cgl0664 | monomeric isocitrate dehydrogenase (NADP+) | 677828 | 680044 | minus |

In an embodiment, the present specification provides for, and includes a recombinant vector comprising a promoter polynucleotide sequence of SEQ ID NO:1 functionally linked to a heterologous target gene recited in Table 2. In an embodiment, the present specification provides for, and includes a recombinant vector comprising a promoter polynucleotide sequence of SEQ ID NO:2 functionally linked to a heterologous target gene recited in Table 2. In an embodiment, the present specification provides for, and includes a recombinant vector comprising a promoter polynucleotide sequence of SEQ ID NO:3 functionally linked to a heterologous target gene recited in Table 2. In an embodiment, the present specification provides for, and includes a recombinant vector comprising a promoter polynucleotide sequence of SEQ ID NO:4 functionally linked to a heterologous target gene recited in Table 2. In an embodiment, the present specification provides for, and includes a recombinant vector comprising a promoter polynucleotide sequence of SEQ ID NO:5 functionally linked to a heterologous target gene recited in Table 2. In an embodiment, the present specification provides for, and includes a recombinant vector comprising a promoter polynucleotide sequence of SEQ ID NO:6 functionally linked to a heterologous target gene recited in Table 2. In an embodiment, the present specification provides for, and includes a recombinant vector comprising a promoter polynucleotide sequence of SEQ ID NO:7 functionally linked to a heterologous target gene recited in Table 2. In an embodiment, the present specification provides for, and includes a recombinant vector comprising a promoter polynucleotide sequence of SEQ ID NO:8 functionally linked to a heterologous target gene recited in Table 2.

In an embodiment, the present specification provides for, and includes, a host cell transformed with a recombinant vector comprising a promoter polynucleotide sequence of SEQ ID NO:1 functionally linked to a heterologous target gene recited in Table 2. In an embodiment, the present specification provides for, and includes, a host cell transformed with a recombinant vector comprising a promoter polynucleotide sequence of SEQ ID NO:2 functionally linked to a heterologous target gene recited in Table 2. In an embodiment, the present specification provides for, and includes, a host cell transformed with a recombinant vector comprising a promoter polynucleotide sequence of SEQ ID NO:3 functionally linked to a heterologous target gene recited in Table 2. In an embodiment, the present specification provides for, and includes, a host cell transformed with a recombinant vector comprising a promoter polynucleotide sequence of SEQ ID NO:4 functionally linked to a heterologous target gene recited in Table 2. In an embodiment, the present specification provides for, and includes, a host cell transformed with a recombinant vector comprising a promoter polynucleotide sequence of SEQ ID NO:5 functionally linked to a heterologous target gene recited in Table 2. In an embodiment, the present specification provides for, and includes, a host cell transformed with a recombinant vector comprising a promoter polynucleotide sequence of SEQ ID NO:6 functionally linked to a heterologous target gene recited in Table 2. In an embodiment, the present specification provides for, and includes, a host cell transformed with a recombinant vector comprising a promoter polynucleotide sequence of SEQ ID NO:7 functionally linked to a heterologous target gene recited in Table 2. In an embodiment, the present specification provides for, and includes, a host cell transformed with a recombinant vector comprising a promoter polynucleotide sequence of SEQ ID NO:8 functionally linked to a heterologous target gene recited in Table 2. As used herein, a host cell refers to an organisms described below in the section entitled 'Expression' that have been transformed with one or more of the promoter cassettes. As will be apparent to one of ordinary skill in the art, a host cell may comprise one or more promoter cassettes as described herein.

In an embodiment, the present specification provides for, and includes, a host cell transformed with a recombinant vector comprising a promoter polynucleotide sequence of SEQ ID NO:1 functionally linked to a heterologous target gene recited in Table 3. In an embodiment, the present specification provides for, and includes, a host cell transformed with a recombinant vector comprising a promoter polynucleotide sequence of SEQ ID NO:2 functionally linked to a heterologous target gene recited in Table 3. In an embodiment, the present specification provides for, and includes, a host cell transformed with a recombinant vector comprising a promoter polynucleotide sequence of SEQ ID NO:3 functionally linked to a heterologous target gene recited in Table 3. In an embodiment, the present specification provides for, and includes, a host cell transformed with a recombinant vector comprising a promoter polynucleotide sequence of SEQ ID NO:4 functionally linked to a heterologous target gene recited in Table 3. In an embodiment, the present specification provides for, and includes, a host cell transformed with a recombinant vector comprising a promoter polynucleotide sequence of SEQ ID NO:5 functionally linked to a heterologous target gene recited in Table 3. In an embodiment, the present specification provides for, and includes, a host cell transformed with a recombinant vector comprising a promoter polynucleotide sequence of SEQ ID NO:6 functionally linked to a heterologous target gene recited in Table 3. In an embodiment, the present specification provides for, and includes, a host cell transformed with a recombinant vector comprising a promoter polynucleotide sequence of SEQ ID NO:7 functionally linked to a heterologous target gene recited in Table 3. In an embodiment, the present specification provides for, and includes, a host cell transformed with a recombinant vector comprising a promoter polynucleotide sequence of SEQ ID NO:8 functionally linked to a heterologous target gene recited in Table 3. As used herein, a host cell refers to an organisms described below in the section entitled 'Expression' that have been transformed with one or more of the promoter cassettes. As will be apparent to one of ordinary skill in the art, a host cell may comprise one or more promoter cassettes as described herein.

TABLE 3

*C. glutamican* L-lysine Biosynthetic Pathway

| Symbol | Gene Name (EC #) | *C. Glutamicum* Gene | Position | Expression |
|---|---|---|---|---|
| asd | aspartate-semialdehyde dehydrogenase (EC: 1.2.1.11) | asd | 270660 . . . 271694 | + |
| dapA | 4-hydroxy-tetrahydrodipicolinate synthase (EC: 4.3.3.7) | dapA | Complement (2079278 . . . 2080183) | + |
| dapB | dihydrodipicolinate reductase (EC: 1.17.1.8) | Cgl1973 | complement (2081188 . . . 2081934) | + |
| dapD | 2,3,4,5-tetrahydropyridine-2-carboxylate N-succinyltransferase (EC: 2.3.1.117) | dapD | complement (1153838 . . . 1154731) | + |
| dapD | 2,3,4,5-tetrahydropyridine-2-carboxylate N-succinyltransferase (EC: 2.3.1.117) | dapD2 | complement (1156194 . . . 1157144) | |
| cg0931 | N-succinyldiaminopimelate aminotransferase (EC: 2.6.1.17) | cg0931 | 863063 . . . 864226 | + |
| dapE | succinyl-diaminopimelate desuccinylase (EC: 3.5.1.18) | dapE | 1157199 . . . 1158308 | + |
| dapF | diaminopimelate epimerase (EG: 5.1.1.7) | dapF | complement (2021891 . . . 2022724) | + |
| lysA | diaminopimelate decarboxylase (EC: 4.1.1.20) | lysA | 1241397 . . . 1242734 | + |
| ddh | diaminopimelate dehydrogenase (EC: 1.4.1.16) | ddh | complement (2760062 . . . 2761024) | + |
| ask (lysC) | Aspartokinase Lysc Alpha And Beta Subunits (EC: 2.7.2.4) | lysC | 269371 . . . 270636 | + |
| aspB | Aspartate Aminotransferase (EC: 2.6.1.1) | aspB | 256618 . . . 257898 | + |
| PTS | Phosphotransferase System (PTS); Glucose-Specific Enzyme II BC Component Of PTS (EC: 2.7.1.69) | ptsG | 1424684 . . . 1426735 | + |
| zwf | glucose-6-phosphate 1-dehydrogenase (EC: 1.1.1.49 1.1.1.363) | zwf | 1669327 . . . 1670871 | + |
| pgi | glucose-6-phosphate isomerase (EC: 5.3.1.9) | pgi | complement (909227 . . . 910849) | + |
| tkt | transketolase (EC: 2.2.1.1) | tkt | 1665870 . . . 1667972 | + |
| fbp | 6-phosphofructokinase 1 (EC: 2.7.1.11) | Cgl1250 | 1315046 . . . 1316086 | + |
| ppc | phosphoenolpyruvate carboxylase (EC: 4.1.1.31) | ppc | complement (1678851 . . . 1681610) | + |
| pyc | pyruvate carboxylase (EC: 6.4.1.1) | pyc | 706684 . . . 710106 | + |
| icd | isocitrate dehydrogenase (EC: 1.1.1.42) | icd | complement (679301 . . . 681517) | − |
| pck | phosphoenolpyruvate carboxykinase (GTP) (EC: 4.1.1.32) | pck | complement (3025365 . . . 3027197) | − |
| odx | Oxaloacetate decarboxylase (EC 4.1.1.3) | odx | AP017369.1: 1508967 . . . 1509782 (from *C. glutamicum* N24) | − |

TABLE 3-continued

C. glutamican L-lysine Biosynthetic Pathway

| Symbol | Gene Name (EC #) | C. Glutamicum Gene | Position | Expression |
| --- | --- | --- | --- | --- |
| hom | homoserine kinase (EC: 2.7.1.39) | Cgl1184 | 1243855 . . . 1244784 | – |
| | homoserine dehydrogenase (EC: 1.1.1.3); | Cgl1183 | 1242507 . . . 1243844 | – |
| | threonine synthase (EC: 4.2.3.1) | Cgl2220 | complement (2353598 . . . 2355043) | – |

In an embodiment, the present specification provides for, and includes a recombinant vector comprising a promoter polynucleotide sequence of SEQ ID NO:1 functionally linked to a heterologous target gene recited in Table 3. In an embodiment, the present specification provides for, and includes a recombinant vector comprising a promoter polynucleotide sequence of SEQ ID NO:2 functionally linked to a heterologous target gene recited in Table 3. In an embodiment, the present specification provides for, and includes a recombinant vector comprising a promoter polynucleotide sequence of SEQ ID NO:3 functionally linked to a heterologous target gene recited in Table 3. In an embodiment, the present specification provides for, and includes a recombinant vector comprising a promoter polynucleotide sequence of SEQ ID NO:4 functionally linked to a heterologous target gene recited in Table 3. In an embodiment, the present specification provides for, and includes a recombinant vector comprising a promoter polynucleotide sequence of SEQ ID NO:5 functionally linked to a heterologous target gene recited in Table 3. In an embodiment, the present specification provides for, and includes a recombinant vector comprising a promoter polynucleotide sequence of SEQ ID NO:6 functionally linked to a heterologous target gene recited in Table 3. In an embodiment, the present specification provides for, and includes a recombinant vector comprising a promoter polynucleotide sequence of SEQ ID NO:7 functionally linked to a heterologous target gene recited in Table 3. In an embodiment, the present specification provides for, and includes a recombinant vector comprising a promoter polynucleotide sequence of SEQ ID NO:8 functionally linked to a heterologous target gene recited in Table 3.

In an embodiment, the present specification provides for, and includes, a host cell transformed with a recombinant vector comprising a promoter polynucleotide sequence of SEQ ID NO:1 functionally linked to a heterologous target gene recited in Table 3. In an embodiment, the present specification provides for, and includes, a host cell transformed with a recombinant vector comprising a promoter polynucleotide sequence of SEQ ID NO:2 functionally linked to a heterologous target gene recited in Table 3. In an embodiment, the present specification provides for, and includes, a host cell transformed with a recombinant vector comprising a promoter polynucleotide sequence of SEQ ID NO:3 functionally linked to a heterologous target gene recited in Table 3. In an embodiment, the present specification provides for, and includes, a host cell transformed with a recombinant vector comprising a promoter polynucleotide sequence of SEQ ID NO:4 functionally linked to a heterologous target gene recited in Table 3. In an embodiment, the present specification provides for, and includes, a host cell transformed with a recombinant vector comprising a promoter polynucleotide sequence of SEQ ID NO:5 functionally linked to a heterologous target gene recited in Table 3. In an embodiment, the present specification provides for, and includes, a host cell transformed with a recombinant vector comprising a promoter polynucleotide sequence of SEQ ID NO:6 functionally linked to a heterologous target gene recited in Table 3. In an embodiment, the present specification provides for, and includes, a host cell transformed with a recombinant vector comprising a promoter polynucleotide sequence of SEQ ID NO:7 functionally linked to a heterologous target gene recited in Table 3. In an embodiment, the present specification provides for, and includes, a host cell transformed with a recombinant vector comprising a promoter polynucleotide sequence of SEQ ID NO:8 functionally linked to a heterologous target gene recited in Table 3. As used herein, a host cell refers to an organisms described below in the section entitled 'Expression' that have been transformed with one or more of the promoter cassettes. As will be apparent to one of ordinary skill in the art, a host cell may comprise one or more promoter cassettes as described herein.

The present specification provides for a host cell transformed with a recombinant vector comprising a promoter polynucleotide sequence selected from the group consisting of SEQ ID NOs:1 to 8 functionally linked to any one of the heterologous target genes from Corynebacterium glutamicum ATCC 13032 provided in Table 4 or their Corynebacterium glutamicum equivalent thereof. Sequence start and end positions correspond to genomic nucleotide accession NC_003450.3. It will be understood by those of ordinary skill in the art that corresponding genes exist in other strains of C. glutamicum and may be readily identified from Table 4. In an embodiment, the present specification provides for, and includes, a host cell transformed with a recombinant vector comprising a promoter polynucleotide sequence of SEQ ID NO:1 functionally linked to a heterologous target gene recited in Table 4. In an embodiment, the present specification provides for, and includes, a host cell transformed with a recombinant vector comprising a promoter polynucleotide sequence of SEQ ID NO:2 functionally linked to a heterologous target gene recited in Table 4. In an embodiment, the present specification provides for, and includes, a host cell transformed with a recombinant vector comprising a promoter polynucleotide sequence of SEQ ID NO:3 functionally linked to a heterologous target gene recited in Table 4. In an embodiment, the present specification provides for, and includes, a host cell transformed with a recombinant vector comprising a promoter polynucleotide sequence of SEQ ID NO:4 functionally linked to a heterologous target gene recited in Table 4. In an embodiment, the present specification provides for, and includes, a host cell transformed with a recombinant vector comprising a promoter polynucleotide sequence of SEQ ID NO:5 functionally linked to a heterologous target gene recited in Table 4. In an embodiment, the present specification provides for, and includes, a host cell transformed with a recombinant vector comprising a promoter polynucleotide sequence of SEQ ID NO:6 functionally linked to a heterologous target gene recited in Table 4. In an embodiment, the present specification provides for, and includes, a host cell transformed with a recombinant vector comprising a promoter polynucleotide sequence of SEQ ID NO:7 functionally linked to a heterologous target gene recited in Table 4. In an embodiment, the present specification provides for, and includes, a host cell transformed with a recombinant vector comprising a promoter polynucleotide sequence of SEQ ID NO:8 functionally linked to a heterologous target gene recited in Table 4. As used herein, a host cell refers to an organisms described below in the section entitled 'Expression' that have been transformed with one or more of the promoter cassettes. As will be apparent to one of ordinary skill in the art, a host cell may comprise one or more promoter cassettes as described herein.

gene recited in Table 4. In an embodiment, the present specification provides for, and includes a recombinant vector comprising a promoter polynucleotide sequence of SEQ ID NO:7 functionally linked to a heterologous target gene recited in Table 4. In an embodiment, the present specification provides for, and includes a recombinant vector comprising a promoter polynucleotide sequence of SEQ ID NO:8 functionally linked to a heterologous target gene recited in Table 4.

In an embodiment, the present specification provides for, and includes, a host cell transformed with a recombinant vector comprising a promoter polynucleotide sequence of SEQ ID NO:1 functionally linked to a heterologous target gene recited in Table 4. In an embodiment, the present specification provides for, and includes, a host cell transformed with a recombinant vector comprising a promoter polynucleotide sequence of SEQ ID NO:2 functionally

TABLE 4

*C. glutamican* L-methionine Biosynthetic Pathway

| Symbol | Gene Name (EC #) | *C. Glutamicum* Gene | Position |
|---|---|---|---|
| lysC | aspartate kinase [EC: 2.7.2.4] | Cgl0251 | 269371 . . . 270636 |
|  | aspartate-semialdehyde dehydrogenase [EC: 1.2.1.11] | Cgl0252 | 270660 . . . 271694 |
| dapA | 4-hydroxy-tetrahydrodipicolinate synthase [EC: 4.3.3.7] | dapA | complement (2079278 . . . 2080183) |
| dapA | 4-hydroxy-tetrahydrodipicolinate synthase [EC: 4.3.3.7] | Cgl2646 | 2815459 . . . 2816397 |
| dapB | 4-hydroxy-tetrahydrodipicolinate reductase [EC: 1.17.1.8] | Cgl1973 | complement (2081188 . . . 2081934) |
| dapD | 2,3,4,5-tetrahydropyridine-2-carboxylate N-succinyltransferase [EC: 2.3.1.117] | Cgl1106 | complement (1152370 . . . 1153263) |
| dapC | N-succinyldiaminopimelate aminotransferase [EC: 2.6.1.17] | Cgl0814 | 861592 . . . 862755 |
| dapE | succinyl-diaminopimelate desuccinylase [EC: 3.5.1.18] | Cgl1109 | 1155731 . . . 1156840 |
| dapF | diaminopimelate epimerase [EC: 5.1.1.7] | dapF | complement (2051842 . . . 2052675) |
| lysA | diaminopimelate decarboxylase [EC: 4.1.1.20] | Cgl1180 | 1239929 . . . 1241266 |

In an embodiment, the present specification provides for, and includes a recombinant vector comprising a promoter polynucleotide sequence of SEQ ID NO:3 functionally linked to a heterologous target gene recited in Table 4. In an embodiment, the present specification provides for, and includes a recombinant vector comprising a promoter polynucleotide sequence of SEQ ID NO:4 functionally linked to a heterologous target gene recited in Table 4. In an embodiment, the present specification provides for, and includes a recombinant vector comprising a promoter polynucleotide sequence of SEQ ID NO:5 functionally linked to a heterologous target gene recited in Table 4. In an embodiment, the present specification provides for, and includes a recombinant vector comprising a promoter polynucleotide sequence of SEQ ID NO:6 functionally linked to a heterologous target linked to a heterologous target gene recited in Table 4. In an embodiment, the present specification provides for, and includes, a host cell transformed with a recombinant vector comprising a promoter polynucleotide sequence of SEQ ID NO:3 functionally linked to a heterologous target gene recited in Table 4. In an embodiment, the present specification provides for, and includes, a host cell transformed with a recombinant vector comprising a promoter polynucleotide sequence of SEQ ID NO:4 functionally linked to a heterologous target gene recited in Table 4. In an embodiment, the present specification provides for, and includes, a host cell transformed with a recombinant vector comprising a promoter polynucleotide sequence of SEQ ID NO:5 functionally linked to a heterologous target gene recited in Table 4. In an embodiment, the present specification provides for, and includes, a host cell transformed with a recombinant vector comprising a promoter polynucleotide sequence of SEQ ID NO:6 functionally linked to a heterologous target gene recited in Table 4. In an embodiment, the present specification provides for, and includes, a host cell transformed with a recombinant vector comprising a promoter polynucleotide sequence of SEQ ID NO:7 functionally linked to a heterologous target gene recited in Table 4. In an embodiment, the present specification provides for, and includes, a host cell transformed with a recombinant vector comprising a promoter polynucleotide sequence of SEQ ID NO:8 functionally linked to a heterologous target gene recited in Table 4.

In some embodiments the target gene is associated with a biosynthetic pathway producing a biomolecule selected from: amino acids, organic acids, flavors and fragrances, biofuels, proteins and enzymes, polymers/monomers and other biomaterials, lipids, nucleic acids, small molecule therapeutics, protein therapeutics, fine chemicals, and nutraceuticals.

In some embodiments the target gene is associated with a biosynthetic pathway producing a secondary metabolite selected from: antibiotics, alkaloids, terpenoids, and polyketides. In some embodiments the target gene is associated with a metabolic pathway producing a primary metabolite selected from: alcohols, amino acids, nucleotides, antioxidants, organic acids, polyols, vitamins, and lipids/fatty acids. In some embodiments the target gene is associated with a biosynthetic pathway producing a macromolecule selected from: proteins, nucleic acids, and polymers In addition it may be advantageous for the production of L-amino acids to enhance, in particular to overexpress one or more enzymes of the respective biosynthesis pathway, glycolysis, anaplerosis, citric acid cycle, pentose phosphate cycle, amino acid export and optionally regulatory proteins.

Thus for example, for the production of L-amino acids, it may be advantageous for one or more genes selected from the following group to be enhanced, in particular overexpressed: the gene dapA coding for dihydrodipicolinate synthase (EP-B 0 197 335); the gene eno coding for enolase (DE: 19947791.4); the gene gap coding for glyceraldehyde-3-phosphate dehydrogenase (Eikmanns (1992), Journal of Bacteriology 174:6076-6086); the gene tpi coding for triosephosphate isomerase (Eikmanns (1992), Journal of Bacteriology 174:6076-6086); the gene pgk coding for 3-phosphoglycerate kinase (Eikmanns (1992), Journal of Bacteriology 174:6076-6086); the gene zwf coding for glucose-6-phosphate dehydrogenase (JP-A-09224661); the gene pyc coding for pyruvate carboxylase (DE-A-198 31 609; Eikmanns (1992), Journal of Bacteriology 174:6076-6086); the gene mqo coding for malate-quinone-oxidoreductase (Molenaar et al., European Journal of Biochemistry 254, 395-403 (1998)); the gene lysC coding for a feedback-resistant aspartate kinase (Accession No. P26512); the gene lysE coding for lysine export (DE-A-195 48 222); the gene hom coding for homoserine dehydrogenase (EP-A 0131171); the gene ilvA coding for threonine dehydratase (Möckel et al., Journal of Bacteriology (1992) 8065-8072)) or the allele ilvA (Fbr) coding for a feedback-resistant threonine dehydratase (Möckel et al., (1994) Molecular Microbiology 13: 833-842); the gene ilvBN coding for acetohydroxy acid synthase (EP-B 0356739); the gene ilvD coding for dihydroxy acid dehydratase (Sahm and Eggeling (1999) Applied and Environmental Microbiology 65: 1973-1979); and the gene zwa1 coding for the Zwa1 protein (DE: 19959328.0, DSM 13115).

Furthermore it may be advantageous for the production of L-amino acids also to attenuate, in particular to reduce, the expression of one or more genes selected from the group: the gene pck coding for phosphoenol pyruvate carboxykinase (DE 199 50 409.1; DSM 13047); the gene pgi coding for glucose-6-phosphate isomerase (U.S. Pat. No. 6,586,214; DSM 12969); the gene poxB coding for pyruvate oxidase (DE: 1995 1975.7; DSM 13114); and the gene zwa2 coding for the Zwa2 protein (DE: 19959327.2, DSM 13113).

In addition, it may furthermore be advantageous, for the production of amino acids, in particular L-lysine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, U K, 1982).

The promoter according to the invention can thus be used in each case for overexpressing or underexpressing the target gene in *C. glutamicum*.

Linkers

The target gene is positioned downstream of the promoter polynucleotide according to the invention, i.e. at the 3' end, such that both polynucleotides are functionally linked to one another either directly or by means of a linker oligonucleotide or linker polynucleotide. Preference is given to the promoter and the target gene being functionally linked to one another by means of a linker oligonucleotide or linker polynucleotide. Said linker oligonucleotide or linker polynucleotide consists of deoxyribonucleotides.

In this context, the expression "functionally linked to one another directly" means that the nucleotide at the 3' end of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 is linked directly to the first nucleotide of the start codon of a target gene. This results in "leaderless" mRNAs which start immediately with the 5'-terminal AUG start codon and therefore do not have any other translation initiation signals.

In this context, the expression "functionally linked to one another by means of a linker oligonucleotide" means that the nucleotide at the 3' end of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 is linked by an oligonucleotide of 1, 2, 3, 4 or 5 nucleotides in length to the first nucleotide of the start codon of a target gene.

In this context, the expression "functionally linked to one another by means of a linker polynucleotide" means that the nucleotide at the 3' end of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 is linked by a polynucleotide of from 6 to no more than 600 nucleotides in length to the first nucleotide of the start codon of a target gene.

In this context, the expression "functionally linked to one another" means that the target gene is bound to the promoter polynucleotide according to the invention in such a way that transcription of the target gene and translation of the synthesized RNA are ensured.

Depending on the technical requirement, the linker polynucleotide is:

6-600, 6-500, 6-400, 6-300, 6-200, 6-180, 6-160, 6-140, 6-120, 6-100, 6-80, 6-60, 6-50, 6-40, 6-30, 6-28, 6-27, 6-26, 6-25; or 8-600, 8-500, 8-400, 8-300, 8-200, 8-180, 8-160, 8-140, 8-120, 8-100, 8-80, 8-60, 8-50, 8-40, 8-30, 8-28, 8-27, 8-26, 8-25; or 10-600, 10-500, 10-400, 10-300, 10-200, 10-180, 10-160, 10-140, 10-120, 10-100, 10-80, 10-60, 10-50, 10-40, 10-30, 10-28, 10-27, 10-26, 10-25; or 12-600, 12-500, 12-400, 12-300, 12-200, 12-180, 12-160, 12-140, 12-120, 12-100, 12-80, 12-60, 12-50, 12-40, 12-30, 12-28, 12-27, 12-26, 12-25; or 14-600, 14-500, 14-400, 14-300, 14-200, 14-180, 14-160, 14-140, 14-120, 14-100, 14-80, 14-60, 14-50, 14-40, 14-30, 14-28, 14-27, 14-26, 14-20; or 16-600, 16-500, 16-400, 16-300, 16-200, 16-180, 16-160, 16-140, 16-120, 16-100, 16-80, 16-60, 16-50, 16-40, 16-30, 16-28, 16-27, 16-26, 16-25; or 18-600, 18-500, 18-400, 18-300, 18-200, 18-180, 18-160, 18-140, 18-120, 18-100, 18-80, 18-60, 18-50, 18-40, 18-30, 18-28, 18-27, 18-26, 18-25; or 20-600, 20-500, 20-400, 20-300, 20-200, 20-180, 20-160, 20-140, 20-120, 20-100, 20-80, 20-60, 20-50, 20-40, 20-30, 20-28, 20-27, 20-26, 20-25 nucleotides in length.

In particularly preferred embodiments, the linker polynucleotide is 20, 21, 22, 23, 24, or 25 nucleotides in length because this produces preferably functional constructs.

The invention further relates accordingly to an isolated promoter polynucleotide, essentially consisting of a polynucleotide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, which, via the nucleotide at its 3' end, is functionally linked, directly or by means of a linker polynucleotide which ensures translation of RNA, to a target gene which contains at its 5' end an ATG or GTG start codon and codes for one or more polypeptide(s). Preference is given to the promoter and target gene being functionally linked to one another by means of a linker polynucleotide.

The invention furthermore also relates to an isolated polynucleotide, essentially consisting of a polynucleotide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, which, via the nucleotide at its 3' end, is functionally linked to a linker oligonucleotide.

In addition, the invention furthermore relates to an isolated polynucleotide, essentially consisting of a polynucleotide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, which, via the nucleotide at its 3' end, is functionally linked to a linker polynucleotide which ensures translation of RNA.

In this context, the term "essentially" means that a polynucleotide of no more than 1,000, no more than 800, no more than 700, no more than 600, no more than 500, or no more than 400 nucleotides in length has been added to the 5' end of the polynucleotide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 and a polynucleotide of no more than 1,000, no more than 800, no more than 700, no more than 600, no more than 500, or no more than 400 nucleotides in length has been added to the 3' of the target gene, or a polynucleotide of no more than 15,000, no more than 10,000, no more than 7,500, no more than 5,000, no more than 2,500, no more than 1,000, no more than 800, no more than 700, no more than 600, no more than 500, or no more than 400 nucleotides in length has been added to the 3' end of the linker oligo- or polynucleotide.

Any useful combination of the features from the preceding three lists of polynucleotides is in accordance with the invention here. "Useful combination" means, for example, a combination of features which results in an efficient recombination being carried out. The use of additions of the same length flanking a DNA region to be replaced facilitates the transfer of the region by homologous recombination in the experimental procedure. Relatively long flanking homologous regions are advantageous for efficient recombination between circular DNA molecules but cloning of the replacement vector is made more difficult with increasing length of the flanks (Wang et al., Molecular Biotechnology 32:43-53 (2006)).

In addition, the flank at the 3' end of the linker oligo- or polynucleotide increases in length to no more than 15,000 nucleotides when the 3' end is functionally linked to a target gene which contains at its 5' end an ATG or GTG start codon and codes for one or more polypeptide(s).

These particularly preferred embodiments of the linker polynucleotide ensure translation of RNA in an advantageous manner.

To facilitate chemical linking between the polynucleotide according to the invention having the nucleotide sequence of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, the linker polynucleotide which ensures translation of RNA, and the target gene coding for one or more polypeptide(s), which has an ATG or GTG start codon at its 5' end, functional nucleotide sequences required for cloning may be incorporated into said polynucleotides at their 5' and 3' ends and are at least partially retained even after said cloning.

The term "functional nucleotide sequence required for cloning" here represents any REII (type II restriction endonuclease) cleavage site present, whose sequence normally consists of from 4 to 8 nucleotides.

In addition, it should be mentioned here that site-specific mutagenesis by means of mutagenesis primers or a de novo gene synthesis (e.g. by GENEART AG (Regensburg, Germany)) of the nucleotide sequences to remove cleavage sites for restriction endonucleases may introduce silent mutations into the sequence in order to enable said cleavage sites to be used advantageously for subsequent cloning steps.

The polynucleotide resulting from the promoter according to the invention being functionally linked to the linker polynucleotide which ensures translation of RNA is also referred to as expression unit herein below.

Expression

The invention furthermore relates to the use of the promoter according to the invention or of the expression unit according to the invention for expressing target genes or polynucleotides in microorganisms. The promoter according to the invention or the expression unit according to the invention ensures transcription and translation of the synthesized RNA, preferably mRNA, into a polypeptide. As used herein, the term "host cell" refers to a transformed cell of a microorganism.

The present disclosure, provides for, and includes, transformed host cells comprising the recombinant nucleic acids and recombinant vectors described in detail above. The present disclosure further provides for, and includes, host cells transformed with two recombinant nucleic acids. In an embodiment, the host cells are transformed with three recombinant nucleic acids. As provided above, the nucleic acids may be selected from biosynthetic pathways based on the overall effect on the yield of the desired product. There is no practical limit the the number of recombinant nucleic acids that may be incorporated into the host cells of the present specification. Expression is preferably carried out in microorganisms of the genus *Corynebacterium*. Preference is given to strains within the genus *Corynebacterium* which are based on the following species: *C. efficiens*, with the deposited type strain being DSM44549; *C. glutamicum*, with the deposited type strain being ATCC13032; and *C. ammoniagenes*, with the deposited type strain being ATCC6871. Very particular preference is given to the species *C. glutamicum*. In this way it is possible to express polynucleotides that code for polypeptides having a property, preferably enzyme activity, which are not present or detectable in the corresponding host. Thus, for example, Yukawa et al. describe expression of *Escherichia coli* genes for utilizing D-xylose in *C. glutamicum* R under the control of the constitutive Ptrc promoter (Applied Microbiology and Biotechnology 81, 691-699 (2008)).

The present specification provides for, and includes *C. glutamicum* having two or more genes of a biosynthetic pathway under the control of the promoter polynucleotide sequences described above. In various embodiments, one or more target genes are placed under the control of a promoter polynucleotide sequence having as sequence of SEQ ID NOs:1 to 8 as described above. In other embodiments, one or more target genes are placed under the control of a promoter polynucleotide sequence having as sequence of SEQ ID NOs:1, 5 or 7 as described above.

In certain embodiments according to the present specification, *C. glutamicum* host cells have two target genes under the control of the promoters having sequences of SEQ ID NOs:1 to 8. In certain other embodiments according to the present specification, *C. glutamicum* host cells have two target genes under the control of the promoters having sequences of SEQ ID NOs:1, 5 or 7. Using homologous recombination, the promoters of the present disclosure replace the endogenous promoter and endogenous sequence to prepare a promoter functionally linked to a heterologous gene. One of ordinary skill in the art would recognize that the recombination results in a replacement of the endogenous promoter while retaining the gene in its native locus. Specific non-limiting examples are illustrated below in Table 8. Multiple promoter-heterologous target pairs (e.g., promoter cassettes) can be readily incorporated into the genome of a host cell. In an embodiment, the promoter cassettes can be incorporated into host cells sequentially. In certain embodiments, the recombinant vectors of the present disclosure provide for two or more different promoter cassettes in a single construct. The present specification provides no practical limit to the number of promoter replacements that can be developed using the described methods.

In an embodiment the host cell is a transgenic *C. glutamicum* host cell comprising the promoter cassettes Pcg0007-lysA and Pcg3121-pgi. In an embodiment the host cell is a transgenic *C. glutamicum* host cell comprising the promoter cassettes Pcg1860-pyc and Pcg0007-zwf. In an embodiment the host cell is a transgenic *C. glutamicum* host cell comprising the promoter cassettes Pcg0007-lysA and Pcg0007-zwf. In an embodiment the host cell is a transgenic *C. glutamicum* host cell comprising the promoter cassettes Pcg3121-pck and Pcg0007-zwf. In an embodiment the host cell is a transgenic *C. glutamicum* host cell comprising the promoter cassettes Pcg0007_39-ppc and Pcg0007-zwf. In an embodiment the host cell is a transgenic *C. glutamicum* host cell comprising the promoter cassettes Pcg3121-pck and Pcg3121-pgi. In an embodiment the host cell is a transgenic *C. glutamicum* host cell comprising the promoter cassettes Pcg3381-ddh and Pcg0007-zwf. In an embodiment the host cell is a transgenic *C. glutamicum* host cell comprising the promoter cassettes Pcg0007_265-dapB and Pcg0007-zwf. In an embodiment the host cell is a transgenic *C. glutamicum* host cell comprising the promoter cassettes Pcg0007-zwf and Pcg3121-pgi. In an embodiment the host cell is a transgenic *C. glutamicum* host cell comprising the promoter cassettes Pcg3381-ddh and Pcg3121-pgi. In an embodiment the host cell is a transgenic *C. glutamicum* host cell comprising the promoter cassettes Pcg3121-pgi and Pcg1860-pyc. In an embodiment the host cell is a transgenic *C. glutamicum* host cell comprising the promoter cassettes Pcg1860-pyc and Pcg0007_265-dapB. In an embodiment the host cell is a transgenic *C. glutamicum* host cell comprising the promoter cassettes Pcg1860-pyc and Pcg0007-lysA. In an embodiment the host cell is a transgenic *C. glutamicum* host cell comprising the promoter cassettes Pcg1860-asd and Pcg0007-zwf. In an embodiment the host cell is a transgenic *C. glutamicum* host cell comprising the promoter cassettes Pcg0007_265-dapB and Pcg3121-pgi. In an embodiment the host cell is a transgenic *C. glutamicum* host cell comprising the promoter cassettes Pcg1860-pyc and Pcg1860-asd. In an embodiment the host cell is a transgenic *C. glutamicum* host cell comprising the promoter cassettes Pcg3381-aspB and Pcg1860-pyc. In an embodiment the host cell is a transgenic *C. glutamicum* host cell comprising the promoter cassettes Pcg3381-fbp and Pcg1860-pyc. In an embodiment the host cell is a transgenic *C. glutamicum* host cell comprising the promoter cassettes Pcg3381-ddh and Pcg3381-fbp. In an embodiment the host cell is a transgenic *C. glutamicum* host cell comprising the promoter cassettes Pcg0755-ptsG and Pcg3121-pgi. In an embodiment the host cell is a transgenic *C. glutamicum* host cell comprising the promoter cassettes Pcg1860-pyc and Pcg3121-pck. In an embodiment the host cell is a transgenic *C. glutamicum* host cell comprising the promoter cassettes Pcg1860-asd and Pcg3121-pgi. In an embodiment the host cell is a transgenic *C. glutamicum* host cell comprising the promoter cassettes Pcg1860-asd and Pcg3381-fbp. In an embodiment the host cell is a transgenic *C. glutamicum* host cell comprising the promoter cassettes Pcg0007_39-lysE and Pcg3381-fbp. In an embodiment the host cell is a transgenic *C. glutamicum* host cell comprising the promoter cassettes Pcg3381-fbp and Pcg0007-lysA. In an embodiment the host cell is a transgenic *C. glutamicum* host cell comprising the promoter cassettes Pcg0007_39-lysE and Pcg1860-pyc. In an embodiment the host cell is a transgenic *C. glutamicum* host cell comprising the promoter cassettes Pcg3121-pgi and Pcg3381-fbp. In an embodiment the host cell is a transgenic *C. glutamicum* host cell comprising the promoter cassettes Pcg3121-pck and Pcg0007-lysA. In an embodiment the host cell is a transgenic *C. glutamicum* host cell comprising the promoter cassettes Pcg0007-lysA and Pcg0007_265-dapB. In an embodiment the host cell is a transgenic *C. glutamicum* host cell comprising the promoter cassettes Pcg0007_265-dapB and Pcg1860-asd. In an embodiment the host cell is a transgenic *C. glutamicum* host cell comprising the promoter cassettes Pcg3121-pgi and Pcg0007_265-dapD. In an embodiment the host cell is a transgenic *C. glutamicum* host cell comprising the promoter cassettes Pcg0007-lysA and Pcg3381-ddh. In an embodiment the host cell is a transgenic *C. glutamicum* host cell comprising the promoter cassettes Pcg3121-pck and Pcg1860-asd. In an embodiment the host cell is a transgenic *C. glutamicum* host cell comprising the promoter cassettes Pcg0007-lysA and Pcg1860-asd. In an embodiment the host cell is a transgenic *C. glutamicum* host cell comprising the promoter cassettes Pcg3121-pck and Pcg0007_265-dapB. In an embodiment the host cell is a transgenic *C. glutamicum* host cell comprising the promoter cassettes Pcg3381-ddh and Pcg1860-asd. In an embodiment the host cell is a transgenic *C. glutamicum* host cell comprising the promoter cassettes Pcg0007_39-ppc and Pcg1860-asd. In an embodiment the host cell is a transgenic *C. glutamicum* host cell comprising the promoter cassettes Pcg0007_39-ppc and Pcg0007-lysA. In an embodiment the host cell is a transgenic *C. glutamicum* host cell comprising the promoter cassettes Pcg3381-ddh and Pcg0007_265-dapB. In an embodiment the host cell is a transgenic *C. glutamicum* host cell comprising the promoter cassettes Pcg0007_265-dapB and Pcg3381-fbp. In an embodiment the host cell is a transgenic *C. glutamicum* host cell comprising the promoter cassettes Pcg0007_39-ppc and Pcg0007_265-dapB. In an embodiment the host cell is a transgenic *C. glutamicum* host cell comprising the promoter cassettes Pcg3381-aspB and Pcg3121-pck. In an embodiment the host cell is a transgenic *C. glutamicum* host cell comprising the promoter cassettes Pcg0007_265-dapB and Pcg0007_265-dapD. In an embodiment the host cell is a transgenic *C. glutamicum* host cell comprising the promoter cassettes Pcg0007_39-lysE and Pcg3381-aspB. In an embodiment the host cell is a transgenic *C. glutamicum* host cell comprising the promoter cassettes Pcg0007_39-lysE and Pcg0007_265-dapD. In an embodiment the host cell is a transgenic *C. glutamicum* host cell comprising the promoter cassettes Pcg3381-aspB and Pcg0007_265-dapB. In an embodiment the host cell is a transgenic *C. glutamicum* host cell comprising the promoter cassettes Pcg1860-asd and Pcg0007_265-dapD. In an embodiment the host cell is a transgenic *C. glutamicum* host cell comprising the promoter cassettes Pcg3381-aspB and Pcg0007-lysA. In an embodiment the host cell is a transgenic *C. glutamicum* host cell comprising the promoter cassettes Pcg3381-aspB and Pcg3381-ddh. In an embodiment the host cell is a transgenic *C. glutamicum* host cell comprising the promoter cassettes Pcg0755-ptsG and Pcg1860-pyc. In an embodiment the host cell is a transgenic *C. glutamicum* host cell comprising the promoter cassettes Pcg0755-ptsG and Pcg3381-fbp. In an embodiment the host cell is a transgenic *C. glutamicum* host cell comprising the promoter cassettes Pcg0007-zwf and Pcg3381-fbp. In an embodiment the host cell is a transgenic *C. glutamicum* host cell comprising the promoter cassettes Pcg0755-ptsG and Pcg0007_265-dapD.

The present disclosure provides for, and includes, host cells having three or more promoter cassettes as described above. In an embodiment, the host cell includes the Pcg0007_39-zwf, Pcg0007_39-lysA and Pcg1860-pyc promoter cassettes. In an embodiment, the host cell is a *C. glutamicum* host cell.

The promoter according to the invention or the expression unit according to the invention is furthermore used for improving the performance characteristics of microorganisms, which can include, for example, yield, titer, productivity, by-product elimination, tolerance to process excursions, optimal growth temperature and growth rate. In some embodiments, the promoter according to the invention or the expression unit according to the invention is used for up-regulating a target gene in a microorganism (overexpression). Overexpression generally means an increase in the intracellular concentration or activity of a ribonucleic acid, a protein (polypeptide) or an enzyme in comparison with the starting strain (parent strain) or wild-type strain, if the latter is the starting strain. In some embodiments, the promoter according to the invention or the expression unit according to the invention is used for down-regulating a target gene in a microorganism (underexpression). Underexpression generally means an decrease in the intracellular concentration or activity of a ribonucleic acid, a protein (polypeptide) or an enzyme in comparison with the starting strain (parent strain) or wild-type strain, if the latter is the starting strain. In some embodiments, a combination of promoters and/or expression units according to the invention are used for regulating expression of more than one target gene in a microorganism, wherein each target gene is either up-regulated or down-regulated. In some embodiments the target genes up- or down-regulated by the combination of promoters and/or expression units are part of the same metabolic pathway. In some embodiments the target genes up- or down-regulated by the combination of promoters and/or expression units are not part of the same metabolic pathway.

The promoters described herein can be used in combination with other methods very well-known in the art for attenuating (reducing or eliminating) the intracellular activity of one or more enzymes (proteins) in a microorganism which are coded by the corresponding DNA, for example by using a weak promoter or using a gene, or allele, which codes for a corresponding enzyme with a low activity, or inactivates the corresponding gene or enzyme (protein), and optionally combining these measures.

The reduction in gene expression can take place by suitable culturing or by genetic modification (mutation) of the signal structures of gene expression. Signal structures of gene expression are, for example, repressor genes, activator genes, operators, promoters, attenuators, ribosome binding sites, the start codon and terminators. The expert can find information on this e.g. in the patent application WO 96/15246, in Boyd and Murphy (Journal of Bacteriology 170: 5949 (1988)), in Voskuil and Chambliss (Nucleic Acids Research 26: 3548 (1998), in Jensen and Hammer (Biotechnology and Bioengineering 58: 191 (1998)), in Patek et al. (Microbiology 142: 1297 (1996)), Vašicová et al. (Journal of Bacteriology 181: 6188 (1999)) and in known textbooks of genetics and molecular biology, such as e.g. the textbook by Knippers ("Molekulare Genetik [Molecular Genetics]", 6th edition, Georg Thieme Verlag, Stuttgart, Germany, 1995) or that by Winnacker ("Gene und Klone [Genes and Clones]", VCH Verlagsgesellschaft, Weinheim, Germany, 1990).

Mutations which lead to a change or reduction in the catalytic properties of enzyme proteins are known from the prior art; examples which may be mentioned are the works by Qiu and Goodman (Journal of Biological Chemistry 272: 8611-8617 (1997)), Sugimoto et al. (Bioscience Biotechnology and Biochemistry 61: 1760-1762 (1997)) and Möckel ("Die Threonindehydratase aus *Corynebacterium glutamicum*: Aufhebung der allosterischen Regulation und Struktur des Enzyms [Threonine dehydratase from *Corynebacterium glutamicum*: Cancelling the allosteric regulation and structure of the enzyme]", Reports from the Jülich Research Centre, Jüt-2906, ISSN09442952, Jülich, Germany, 1994). Comprehensive descriptions can be found in known textbooks of genetics and molecular biology, such as e.g. that by Hagemann ("Allgemeine Genetik [General Genetics]", Gustav Fischer Verlag, Stuttgart, 1986).

Possible mutations are transitions, transversions, insertions and deletions. Depending on the effect of the amino acid exchange on the enzyme activity, missense mutations or nonsense mutations are referred to. Insertions or deletions of at least one base pair in a gene lead to frame shift mutations, as a consequence of which incorrect amino acids are incorporated or translation is interrupted prematurely. Deletions of several codons typically lead to a complete loss of the enzyme activity. Instructions on generation of such mutations are prior art and can be found in known textbooks of genetics and molecular biology, such as e.g. the textbook by Knippers ("Molekulare Genetik [Molecular Genetics]", 6th edition, Georg Thieme Verlag, Stuttgart, Germany, 1995), that by Winnacker ("Gene and Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986). A common method of mutating genes of *C. glutamicum* is the method of gene disruption and gene replacement described by Schwarzer and Paler (Bio/Technology 9, 84-87 (1991)).

In the method of gene disruption a central part of the coding region of the gene of interest is cloned in a plasmid vector which can replicate in a host (typically *E. coli*), but not in *C. glutamicum*. Possible vectors are, for example, pSUP301 (Simon et al., Bio/Technology 1, 784-791 (1983)), pK18mob or pK19mob (Schafer et al., Gene 145, 69-73 (1994)), pK18mobsacB or pK19mobsacB (Jäger et al., Journal of Bacteriology 174: 5462-65 (1992)), pGEM-T (Promega corporation, Madison, Wis., USA), pCR2.1-TOPO (Shuman (1994). Journal of Biological Chemistry 269: 32678-84; U.S. Pat. No. 5,487,993), pCR®Blunt (Invitrogen, Groningen, Holland; Bernard et al., Journal of Molecular Biology, 234: 534-541 (1993)) or pEM1 (Schrumpf et al, 1991, Journal of Bacteriology 173:4510-4516). The plasmid vector which contains the central part of the coding region of the gene is then transferred into the desired strain of *C. glutamicum* by conjugation or transformation. The method of conjugation is described, for example, by Schafer et al. (Applied and Environmental Microbiology 60, 756-759 (1994)). Methods for transformation are described, for example, by Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)). After homologous recombination by means of a "cross-over" event, the coding region of the gene in question is interrupted by the vector sequence and two incomplete alleles are obtained, one lacking the 3' end and one lacking the 5' end. This method has been used, for example, by Fitzpatrick et al. (Applied Microbiology and Biotechnology 42, 575-580 (1994)) to eliminate the recA gene of *C. glutamicum*.

In the method of gene replacement, a mutation, such as e.g. a deletion, insertion or base exchange, is established in vitro in the gene of interest. The allele prepared is in turn cloned in a vector which is not replicative for *C. glutamicum* and this is then transferred into the desired host of *C. glutamicum* by transformation or conjugation. After homologous recombination by means of a first "cross-over" event which effects integration and a suitable second "cross-over" event which effects excision in the target gene or in the target sequence, the incorporation of the mutation or of the allele is achieved. This method was used, for example, by Peters-Wendisch (Microbiology 144, 915-927 (1998)) to eliminate the pyc gene of *C. glutamicum* by a deletion.

The promoters described herein can be used in combination with other methods very well-known in the art for raising (enhancing) the intracellular activity of one or more enzymes in a microorganism that are coded by the corresponding DNA, by for example increasing the number of copies of the gene or genes, using a strong promoter, or using a gene that codes for a corresponding enzyme having a high activity, and optionally combining these measures.

In order to achieve an overexpression the number of copies of the corresponding genes can be increased, or alternatively the promoter and regulation region or the ribosome binding site located upstream of the structure gene can be mutated. Expression cassettes that are incorporated upstream of the structure gene act in the same way. By means of inducible promoters it is in addition possible to increase the expression in the course of the enzymatic amino acid production. The expression is similarly improved by measures aimed at prolonging the lifetime of the m-RNA. Furthermore, the enzyme activity is also enhanced by preventing the degradation of the enzyme protein. The genes or gene constructs may either be present in plasmids having different numbers of copies, or may be integrated and amplified in the chromosome. Alternatively, an overexpression of the relevant genes may furthermore be achieved by altering the composition of the media and the culture conditions.

The person skilled in the art can find details on the above in, inter alia, Martin et al. (Bio/Technology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in European Patent Specification 0 472 869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in Patent Application WO 96/15246, in Malumbres et al. (Gene 134, 15-24 (1993)), in Japanese laid open Specification JP-A-10-229891, in Jensen and Hammer (Biotechnology and Bioengineering 58, 191-195 (1998)), in Makrides (Microbiological Reviews 60:512-538 (1996)) and in known textbooks on genetics and molecular biology.

Genes may be overexpressed for example by means of episomal plasmids. Suitable plasmids are those that are replicated in coryneform bacteria. Numerous known plasmid vectors, such as for example pZ1 (Menkel et al., Applied and Environmental Microbiology (1989) 64: 549-554), pEKEx1 (Eikmanns et al., Gene 102:93-98 (1991)) or pHS2-1 (Sonnen et al., Gene 107:69-74 (1991)) are based on the cryptic plasmids pHM1519, pBL1 or pGA1. Other plasmid vectors, such as for example those based on pCG4 (U.S. Pat. No. 4,489,160), or pNG2 (Serwold-Davis et al., FEMS Microbiology Letters 66, 119-124 (1990)), or pAG1 (U.S. Pat. No. 5,158,891) may be used in a similar way.

Furthermore, also suitable are those plasmid vectors with the aid of which the process of gene amplification by integration in the chromosome can be employed, such as has been described for example by Reinscheid et al. (Applied and Environmental Microbiology 60, 126-132 (1994)) for the duplication and amplification of the hom-thrB operon. In this method the complete gene is cloned into a plasmid vector that can replicate in a host (typically *E. coli*) but not in *C. glutamicum*. Suitable vectors are for example pSUP301 (Simon et al., Bio/Technology 1, 784-791 (1983)), pK18mob or pK19 mob (Schafer et al., Gene 145, 69-73 (1994)), pGEM-T (Promega Corporation, Madison, Wis., USA), pCR2.1-TOPO (Shuman (1994). Journal of Biological Chemistry 269:32678-84; U.S. Pat. No. 5,487,993), pCR®Blunt (Invitrogen, Groningen, Netherlands; Bernard et al., Journal of Molecular Biology, 234: 534-541 (1993)), pEM1 (Schrumpf et al, 1991, Journal of Bacteriology 173: 4510-4516) or pBGS8 (Sprat et al., 1986, Gene 41: 337-342). The plasmid vector that contains the gene to be amplified is then transferred by conjugation or transformation into the desired strain of *C. glutamicum*. The method of conjugation is described for example in Schafer et al. (Applied and Environmental Microbiology 60, 756-759 (1994)). Transformation methods are described for example in Thierbach et al. (Applied Microbiology and Biotechnology 29, 356-362 (1988)), Dunican and Shivnan (Bio/Technology 7, 1067-1070 (1989)) and Tauch et al. (FEMS Microbiological Letters 123, 343-347 (1994)). After homologous recombination by means of a crossover event, the resulting strain contains at least two copies of the relevant gene.

Methods of regulating, i.e., either increasing or decreasing, gene expression include recombinant methods in which a microorganism is produced using a DNA molecule provided in vitro. Such DNA molecules comprise, for example, promoters, expression cassettes, genes, alleles, coding regions, etc. They are introduced into the desired microorganisms by methods of transformation, conjugation, transduction or similar methods.

In the case of the present invention, the promoters are preferably a polynucleotide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8, and the expression cassettes are preferably a polynucleotide of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 which, via the nucleotide at its 3' end, are functionally linked to a linker polynucleotide which ensures translation of RNA.

The measures of overexpression using the promoter according to the invention or the expression unit according to the invention increase the activity or concentration of the corresponding polypeptide usually by at least 10%, 25%, 50%, 75%, 100%, 150%, 200%, 300%, 400% or 500%, preferably by no more than 1,000%, 2,000%, 4,000%, 10,000% or 20,000%, based on the activity or concentration of said polypeptide in the strain prior to the measure resulting in overexpression.

The extent of expression or overexpression may be established by measuring the amount of mRNA transcribed from the gene, by determining the amount of polypeptide and by determining enzyme activity.

The amount of mRNA may be determined inter alia by using the methods of "Northern Blotting" and of quantitative RT-PCR. Quantitative RT-PCR involves reverse transcription which precedes the polymerase chain reaction. For this, the LightCycler™ System from Roche Diagnostics (Boehringer Mannheim GmbH, Roche Molecular Biochemicals, Mannheim, Germany) may be used, as described in Jungwirth et al. (FEMS Microbiology Letters 281, 190-197 (2008)), for example. The concentration of the protein may be determined via 1- and 2-dimensional protein gel fractionation and subsequent optical identification of the protein concentration using appropriate evaluation software in the gel. A customary method of preparing protein gels for coryneform bacteria and of identifying said proteins is the procedure described by Hermann et al. (Electrophoresis, 22:1712-23 (2001)). The protein concentration may likewise be determined by Western-Blot hybridization using an antibody specific for the protein to be detected (Sambrook et al., Molecular cloning: a laboratory manual. 2nd Ed. Cold Spring Harbor Laboratory Press, Cold Spring Harbor, N.Y., 1989) and subsequent optical evaluation using appropriate software for concentration determination (Lohaus and Meyer (1998) Biospektrum 5:32-39; Lottspeich, Angewandte Chemie 321: 2630-2647 (1999)). The statistical significance of the data collected is determined by means of a T test (Gosset, Biometrika 6(1): 1-25 (1908)).

The measure of overexpressing target genes using the promoter according to the invention may be combined in a suitable manner with further overexpression measures. Overexpression is achieved by a multiplicity of methods available in the prior art. These include increasing the copy number in addition to modifying the nucleotide sequences which direct or control expression of the gene. The copy number may be increased by means of plasmids which replicate in the cytoplasm of the microorganism. To this end, an abundance of plasmids are described in the prior art for very different groups of microorganisms, which plasmids can be used for setting the desired increase in the copy number of the gene. Plasmids suitable for the genus Corynebacterium are described, for example, in Tauch et al. (Journal of Biotechnology 104 (1-3), 27-40, (2003)), and in Stamen et al. (Applied and Environmental Microbiology 71, 5920-5928 (2005)).

The copy number may furthermore be increased by at least one (1) copy by introducing further copies into the chromosome of the microorganism. Methods suitable for the genus Corynebacterium are described, for example, in the patents WO 03/014330, WO 03/040373 and WO 04/069996.

Gene expression may furthermore be increased by positioning a plurality of promoters upstream of the target gene or functionally linking them to the gene to be expressed and achieving increased expression in this way. Examples of this are described in the patent WO 2006/069711.

Transcription of a gene is controlled, where appropriate, by proteins which suppress (repressor proteins) or promote (activator proteins) transcription. Accordingly, overexpression can likewise be achieved by increasing the expression of activator proteins or reducing or switching off the expression of repressor proteins or else eliminating the binding sites of the repressor proteins. The rate of elongation is influenced by the codon usage, it being possible to enhance translation by utilizing codons for transfer RNAs (tRNAs) which are frequent in the starting strain. Moreover, replacing a start codon with the ATG codon most frequent in many microorganisms (77% in $E.\ coli$) may considerably improve translation, since, at the RNA level, the AUG codon is two to three times more effective than the codons GUG and UUG, for example (Khudyakov et al., FEBS Letters 232(2): 369-71(1988); Reddy et al., Proceedings of the National Academy of Sciences of the USA 82(17):5656-60 (1985)). It is also possible to optimize the sequences surrounding the start codon because synergistic effects between the start codon and the flanking regions have been described (Stenström et al., Gene 273(2):259-65 (2001); Hui et al., EMBO Journal 3(3):623-9 (1984)).

Instructions for handling DNA, digestion and ligation of DNA, transformation and selection of transformants can be found inter alia in the known manual by Sambrook et al. "Molecular Cloning: A Laboratory Manual, Second Edition (Cold Spring Harbor Laboratory Press, 1989).

The invention also relates to vectors comprising the polynucleotides according to the invention.

Kirchner and Tauch (Journal of Biotechnology 104:287-299 (2003)) describe a selection of vectors to be used in *C. glutamicum*.

Homologous recombination using the vectors according to the invention allows DNA segments on the chromosome to be replaced with polynucleotides according to the invention which are transported into the cell by the vector. For efficient recombination between the circular DNA molecule of the vector and the target DNA on the chromosome, the DNA region to be replaced with the polynucleotide according to the invention is provided at the ends with nucleotide sequences homologous to the target site which determine the site of integration of the vector and of replacement of the DNA.

Thus the promoter polynucleotide according to the invention may: 1) be replaced with the native promoter at the native gene locus of the target gene in the chromosome; or 2) be integrated with the target gene at the native gene locus of the latter or at another gene locus.

"Replacement of the native promoter at the native gene locus of the target gene" means the fact that the naturally occurring promoter of the gene which usually is naturally present by way of a single copy at its gene locus in the corresponding wild type or corresponding starting organism in the form of its nucleotide sequence is replaced.

"Another gene locus" means a gene locus whose nucleotide sequence is different from the sequence of the target gene. Said other gene locus or the nucleotide sequence at said other gene locus is preferably located within the chromosome and normally is not essential for growth and for production of the desired chemical compounds. It is furthermore possible to use intergenic regions within the chromosome, i.e. nucleotide sequences without coding function.

Expression or overexpression is preferably carried out in microorganisms of the genus *Corynebacterium*. Within the genus *Corynebacterium*, preference is given to strains based on the following species: *C. efficiens*, with the deposited type strain being DSM44549, *C. glutamicum*, with the deposited type strain being ATCC13032, and *C. ammoniagenes*, with the deposited type strain being ATCC6871. Very particular preference is given to the species *C. glutamicum*.

Suitable strains of the genus *Corynebacterium*, in particular of the species *Corynebacterium glutamicum*, are in particular the known wild-type strains: *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermentum* ATCC13869, and *Brevibacterium divaricatum* ATCC14020; and L-amino acid-producing mutants, or strains, prepared therefrom, such as, for example, the L-lysine-producing strains: *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, *Corynebacterium glutamicum* DM58-1, *Corynebacterium glutamicum* DG52-5, *Corynebacterium glutamicum* DSM5714, and *Corynebacterium glutamicum* DSM12866.

The term "*Micrococcus glutamicus*" has also been in use for *C. glutamicum*. Some representatives of the species *C. efficiens* have also been referred to as *C. thermoaminogenes* in the prior art, such as the strain FERM BP-1539, for example.

The microorganisms or strains (starting strains) employed for the expression or overexpression measures according to the invention preferably already possess the ability to secrete a desired fine chemical into the surrounding nutrient medium and accumulate there. The expression "to produce" is also used for this herein below. More specifically, the strains employed for the overexpression measures possess the ability to accumulate the desired fine chemical in concentrations of at least 0.10 g/L, at least 0.25 g/L, at least 0.5 g/L, at least 1.0 g/L, at least 1.5 g/L, at least 2.0 g/L, at least 4.0 g/L, or at least 10.0 g/L in no more than 120 hours, no more than 96 hours, no more than 48 hours, no more than 36 hours, no more than 24 hours, or no more than 12 hours in the cell or in the nutrient medium. The starting strains are preferably strains prepared by mutagenesis and selection, by recombinant DNA technologies or by a combination of both methods.

A person skilled in the art understands that a microorganism suitable for the measures of the invention may also be obtained by firstly employing the promoter according to the invention of SEQ ID NO:1, SEQ ID NO:2, SEQ ID NO:3, SEQ ID NO:4, SEQ ID NO:5, SEQ ID NO:6, SEQ ID NO:7, or SEQ ID NO:8 for overexpression of the target genes in a wild strain such as, for example, the *C. glutamicum* type strain ATCC 13032 or the strain ATCC 14067, and then, by means of further genetic measures described in the prior art, causing the microorganism to produce the desired fine chemical(s).

The term "biomolecules" means with regard to the measures of the invention amino acids, organic acids, vitamins, nucleosides and nucleotides. Particular preference is given to proteinogenic amino acids, non-proteinogenic amino acids, macromolecules, and organic acids.

"Proteinogenic amino acids" mean the amino acids which occur in natural proteins, i.e. in proteins of microorganisms, plants, animals and humans They serve as structural units for proteins in which they are linked to one another via peptide bonds.

Where L-amino acids or amino acids are mentioned hereinbelow, they are to be understood as meaning one or more amino acids, including their salts, selected from the group L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-lysine is especially preferred. L-Amino acids, in particular lysine, are used in human medicine and in the pharmaceuticals industry, in the foodstuffs industry and very particularly in animal nutrition. There is therefore a general interest in providing new improved processes for the preparation of amino acids, in particular L-lysine.

The terms protein and polypeptide are interchangeable.

The present invention provides a microorganism which produces a fine chemical, said microorganism having increased expression of one or more genes in comparison to the particular starting strain by using the promoter according to the invention of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Fermentative Preparation

The present invention furthermore provides a process for fermentative preparation of a fine chemical, comprising the steps of:

a) culturing the above-described microorganism according to the present invention in a suitable medium, resulting in a fermentation broth; and b) concentrating the fine chemical in the fermentation broth of a) and/or in the cells of the microorganism.

Preference is given here to obtaining from the fine chemical-containing fermentation broth the fine chemical or a liquid or solid fine chemical-containing product. The microorganisms produced may be cultured continuously—as described, for example, in WO 05/021772—or discontinuously in a batch process (batch cultivation) or in a fed-batch or repeated fed-batch process for the purpose of producing the desired organic-chemical compound. A summary of a general nature about known cultivation methods is available in the textbook by Chmiel (Bioprozeßtechnik. 1: Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium or fermentation medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981). The terms culture medium and fermentation medium are interchangeable.

It is possible to use, as carbon source, sugars and carbohydrates such as, for example, glucose, sucrose, lactose, fructose, maltose, molasses, sucrose-containing solutions from sugar beet or sugar cane processing, starch, starch hydrolysate, and cellulose; oils and fats such as, for example, soybean oil, sunflower oil, groundnut oil and coconut fat; fatty acids such as, for example, palmitic acid, stearic acid, and linoleic acid; alcohols such as, for example, glycerol, methanol, and ethanol; and organic acids such as, for example, acetic acid or lactic acid.

It is possible to use, as nitrogen source, organic nitrogen-containing compounds such as peptones, yeast extract, meat extract, malt extract, corn steep liquor, soybean flour, and urea; or inorganic compounds such as ammonium sulfate, ammonium chloride, ammonium phosphate, ammonium carbonate, and ammonium nitrate. The nitrogen sources can be used individually or as a mixture.

It is possible to use, as phosphorus source, phosphoric acid, potassium dihydrogen phosphate or dipotassium hydrogen phosphate or the corresponding sodium-containing salts.

The culture medium may additionally comprise salts, for example in the form of chlorides or sulfates of metals such as, for example, sodium, potassium, magnesium, calcium and iron, such as, for example, magnesium sulfate or iron sulfate, which are necessary for growth. Finally, essential growth factors such as amino acids, for example homoserine and vitamins, for example thiamine, biotin or pantothenic acid, may be employed in addition to the abovementioned substances.

Said starting materials may be added to the culture in the form of a single batch or be fed in during the cultivation in a suitable manner.

The pH of the culture can be controlled by employing basic compounds such as sodium hydroxide, potassium hydroxide, ammonia, or aqueous ammonia; or acidic compounds such as phosphoric acid or sulfuric acid in a suitable manner. The pH is generally adjusted to a value of from 6.0 to 8.5, preferably 6.5 to 8. To control foaming, it is possible to employ antifoams such as, for example, fatty acid polyglycol esters. To maintain the stability of plasmids, it is possible to add to the medium suitable selective substances such as, for example, antibiotics. The fermentation is preferably carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch or fed-batch processes, the cultivation is preferably continued until an amount of the desired organic-chemical compound sufficient for being recovered has formed. This aim is normally achieved within 10 hours to 160 hours. In continuous processes, longer cultivation times are possible. The activity of the microorganisms results in a concentration (accumulation) of the organic-chemical compound in the fermentation medium and/or in the cells of said microorganisms.

Examples of suitable fermentation media can be found inter alia in the U.S. Pat. Nos. 5,770,409, 5,990,350, 5,275,940, WO 2007/012078, U.S. Pat. No. 5,827,698, WO 2009/043803, U.S. Pat. Nos. 5,756,345 and 7,138,266.

Analysis of L-amino acids to determine the concentration at one or more time(s) during the fermentation can take place by separating the L-amino acids by means of ion exchange chromatography, preferably cation exchange chromatography, with subsequent post-column derivatization using ninhydrin, as described in Spackman et al. (Analytical Chemistry 30:1190-1206 (1958)). It is also possible to employ ortho-phthaldialdehyde rather than ninhydrin for post-column derivatization. An overview article on ion exchange chromatography can be found in Pickering (LC-GC Magazine of Chromatographic Science) 7(6), 484-487 (1989)).

It is likewise possible to carry out a pre-column derivatization, for example using ortho-phthaldialdehyde or phenyl isothiocyanate, and to fractionate the resulting amino acid derivates by reversed-phase (RP) chromatography, preferably in the form of high-performance liquid chromatography (HPLC). A method of this type is described, for example, in Lindroth et al. (Analytical Chemistry 51:1167-1174 (1979)).

Detection is carried out photometrically (absorption, fluorescence).

A review regarding amino acid analysis can be found inter alia in the textbook "Bioanalytik" from Lottspeich and Zorbas (Spektrum Akademischer Verlag, Heidelberg, Germany 1998).

Determination of the concentration of α-ketoacids at one or more time point(s) in the course of the fermentation may be carried out by separating the ketoacids and other secreted products by means of ion exchange chromatography, preferably cation exchange chromatography, on a sulfonated styrene-divinylbenzene polymer in the H+ form, for example by means of 0.025 M sulfuric acid with subsequent UV detection at 215 nm (alternatively also at 230 or 275 nm). Preferably, a REZEK RFQ—Fast Fruit H+ column (Phenomenex) may be employed, but other suppliers for the separating phase (e g. Aminex from BioRad) are feasible. Similar separations are described in application examples by the suppliers.

The performance of the processes or fermentation processes containing the promoter variants according to the invention, in terms of one or more of the parameters selected from the group of concentration (compound formed per unit volume), yield (compound formed per unit carbon source consumed), formation (compound formed per unit volume and time) and specific formation (compound formed per unit dry cell matter or dry biomass and time or compound formed per unit cellular protein and time) or else other process parameters and combinations thereof, is increased by at least 0.5%, at least 1%, at least 1.5%, at least 2%, at least 3%, at least 4%, at least 5%, at least 10%, at least 20%, at least 30%, at least 40%, at least 50%, at least 60%, at least 70%, at least 80%, at least 90%, or at least 100% based on processes or fermentation processes using microorganisms not containing the promoter variants according to the invention. This is considered to be very worthwhile in terms of a large-scale industrial process.

The fermentation measures result in a fermentation broth which contains the desired fine chemical, preferably amino acids, organic acids, vitamins, nucleosides or nucleotides.

A product containing the fine chemical is then provided or produced or recovered in liquid or solid form.

A fermentation broth means a fermentation medium or nutrient medium in which a microorganism has been cultivated for a certain time and at a certain temperature. The fermentation medium or the media employed during fermentation comprise(s) all the substances or components which ensure production of the desired compound and typically propagation and viability.

When the fermentation is complete, the resulting fermentation broth accordingly comprises:

a) the biomass (cell mass) of the microorganism, said biomass having been produced due to propagation of the cells of said microorganism;

b) the desired fine chemical formed during the fermentation;

c) the organic byproducts possibly formed during the fermentation; and d) the constituents of the fermentation medium employed or of the starting materials, such as, for example, vitamins such as biotin or salts such as magnesium sulfate, which have not been consumed in the fermentation.

The organic byproducts include substances which are produced by the microorganisms employed in the fermentation in addition to the particular desired compound and are optionally secreted.

The fermentation broth is removed from the culture vessel or fermentation tank, collected where appropriate, and used for providing a product containing the fine chemical in liquid or solid form. The expression "recovering the fine chemical-containing product" is also used for this. In the simplest case, the fine chemical-containing fermentation broth itself, which has been removed from the fermentation tank, constitutes the recovered product.

One or more of the measures selected from the group consisting of a) partial (>0% to <80%) to complete (100%) or virtually complete (≥80%, ≥90%, ≥95%, ≥96%, ≥97%, ≥98%, or ≥99%) removal of the water;

b) partial (>0% to <80%) to complete (100%) or virtually complete (≥80%, ≥90%, ≥95%, ≥96%, ≥97%, ≥98%, or ≥99%) removal of the biomass, the latter being optionally inactivated before removal;

c) partial (>0% to <80%) to complete (100%) or virtually complete (≥80%, ≥90%, ≥95%, ≥96%, ≥97%, ≥98%, ≥99%, ≥99.3%, or ≥99.7%) removal of the organic byproducts formed during fermentation; and d) partial (>0%) to complete (100%) or virtually complete (≥80%, ≥90%, ≥95%, ≥96%, ≥97%, ≥98%, ≥99%, ≥99.3%, or ≥99.7%) removal of the constituents of the fermentation medium employed or of the starting materials, which have not been consumed in the fermentation, from the fermentation broth achieves concentration or purification of the desired organic-chemical compound. Products having a desired content of said compound are isolated in this way.

The partial (>0% to <80%) to complete (100%) or virtually complete (≥80% to <100%) removal of the water (measure a)) is also referred to as drying.

In one variant of the process, complete or virtually complete removal of the water, of the biomass, of the organic byproducts and of the unconsumed constituents of the fermentation medium employed results in pure (≥80% by weight, ≥90% by weight) or high-purity (≥95% by weight, ≥97% by weight, or ≥99% by weight) product forms of the desired organic-chemical compound. An abundance of technical instructions for measures a), b), c) and d) are available in the prior art.

Depending on requirements, the biomass can be removed wholly or partly from the fermentation broth by separation methods such as, for example, centrifugation, filtration, decantation or a combination thereof, or be left completely therein. Where appropriate, the biomass or the biomass-containing fermentation broth is inactivated during a suitable process step, for example by thermal treatment (heating) or by addition of acid.

In one procedure, the biomass is completely or virtually completely removed so that no (0%) or at most 30%, at most 20%, at most 10%, at most 5%, at most 1% or at most 0.1% biomass remains in the prepared product. In a further procedure, the biomass is not removed, or is removed only in small proportions, so that all (100%) or more than 70%, 80%, 90%, 95%, 99% or 99.9% biomass remains in the product prepared. In one process according to the invention, accordingly, the biomass is removed in proportions of from ≥0% to ≤100%.

Finally, the fermentation broth obtained after the fermentation can be adjusted, before or after the complete or partial removal of the biomass, to an acidic pH with an inorganic acid such as, for example, hydrochloric acid, sulfuric acid, or phosphoric acid; or organic acid such as, for example, propionic acid, so as to improve the handling properties of the final product (GB 1,439,728 or EP 1 331220). It is likewise possible to acidify the fermentation broth with the complete content of biomass. Finally, the broth can also be stabilized by adding sodium bisulfite ($NaHCO_3$, GB 1,439, 728) or another salt, for example ammonium, alkali metal, or alkaline earth metal salt of sulfurous acid.

During the removal of the biomass, any organic or inorganic solids present in the fermentation broth are partially or completely removed. The organic byproducts dissolved in the fermentation broth, and the dissolved unconsumed constituents of the fermentation medium (starting materials), remain at least partly (>0%), preferably to an extent of at least 25%, particularly preferably to an extent of at least 50% and very particularly preferably to an extent of at least 75% in the product. Where appropriate, they also remain completely (100%) or virtually completely, meaning >95% or >98% or >99%, in the product. If a product in this sense comprises at least part of the constituents of the fermentation broth, this is also described by the term "product based on fermentation broth".

Subsequently, water is removed from the broth, or said broth is thickened or concentrated, by known methods such as, for example, using a rotary evaporator, thin-film evaporator, falling-film evaporator, by reverse osmosis or by nanofiltration. This concentrated fermentation broth can then be worked up to free-flowing products, in particular to a fine powder or preferably coarse granules, by methods of freeze drying, spray drying, spray granulation or by other processes such as in the circulating fluidized bed, as described for example according to PCT/EP2004/006655. A desired product is isolated where appropriate from the resulting granules by screening or dust removal. It is likewise possible to dry the fermentation broth directly, i.e. without previous concentration by spray drying or spray granulation.

"Free-flowing" means powders which, from a series of glass orifice vessels with orifices of different sizes, flow unimpeded at least out of the vessel with a 5 mm orifice (Klein: Seifen, Öle, Fette, Wachse 94, 12 (1968)).

"Fine" means a powder predominantly (>50%) having a particle size of diameter from 20 to 200 µm.

"Coarse" means a product predominantly (>50%) of a particle size of diameter from 200 to 2000 µm.

The particle size determination can be carried out by methods of laser diffraction spectrometry. Corresponding methods are described in the textbook "Teilchengrößenmessung in der Laborpraxis" by R. H. Müller and R. Schuhmann, Wissenschaftliche Verlagsgesellschaft Stuttgart (1996) or in the text book "Introduction to Particle Technology" by M. Rhodes, published by Wiley & Sons (1998).

The free-flowing, fine powder can in turn be converted by suitable compaction or granulation processes into a coarse, very free-flowing, storable and substantially dust-free product.

The term "dust-free" means that the product comprises only small proportions (<5%) of particle sizes below 100 μm in diameter.

"Storable" in the sense of this invention means a product which can be stored for at least one (1) year or longer, preferably at least 1.5 years or longer, particularly preferably two (2) years or longer, in a dry and cool environment without any substantial loss of the respective organic-chemical compound occurring. "Substantial loss" means a loss of >5%.

It is advantageous to employ during the granulation or compaction the usual organic or inorganic auxiliaries or carriers such as starch, gelatin, cellulose derivatives or similar substances, as normally used in the processing of food products or feeds as binders, gelling agents or thickeners, or further substances such as, for example, silicas, silicates (EP0743016A) and stearates.

It is further advantageous to treat the surface of the resulting granules with oils or fats as described in WO04/054381. Oils which can be used are mineral oils, vegetable oils or mixtures of vegetable oils. Examples of such oils are soybean oil, olive oil, soybean oil/lecithin mixtures. In the same way, silicone oils, polyethylene glycols or hydroxyethylcellulose are also suitable. Treatment of the surfaces of the granules with said oils achieves an increased abrasion resistance of the product and a reduction in the dust content. The oil content in the product is 0.02 to 2.0% by weight, preferably 0.02 to 1.0% by weight, and very particularly preferably 0.2 to 1.0% by weight, based on the total amount of the feed additive.

Preferred products have a proportion of ≥97% by weight with a particle size of from 100 to 1800 or a proportion of ≥95% by weight with a particle size of diameter 300 to 1800 μm. The proportion of dust, i.e. particles with a particle size <100 μm, is preferably >0 to 1% by weight, particularly preferably not exceeding 0.5% by weight.

However, alternatively, the product may also be absorbed on an organic or inorganic carrier known and customary in the processing of feeds, such as, for example, silicas, silicates, meals, brans, flours, starches, sugars or others, and/or be mixed and stabilized with customary thickeners or binders. Examples of use and processes therefor are described in the literature (Die Mühle+ Mischfuttertechnik 132 (1995) 49, page 817).

EMBODIMENTS

1. A recombinant nucleic acid molecule comprising a promoter polynucleotide sequence selected from the group consisting of SEQ ID NOs:1 to 8 functionally linked to at least one heterologous target gene.
2. The recombinant nucleic acid molecule according to claim 1, wherein said promoter polynucleotide sequence is selected from the group consisting of SEQ ID NOs:1, 5 and 7.
3. The recombinant nucleic acid molecule according to embodiments 1 or 2, further comprising a linker oligonucleotide or linker polynucleotide.
4. The recombinant nucleic acid molecule according to embodiment 1, wherein said at least one heterologous target gene is a gene that is a component of a biosynthetic pathway producing a biomolecule selected from the group consisting of amino acids, organic acids, proteins and polymers.
5. The recombinant nucleic acid molecule according to embodiment 4, wherein said at least one heterologous target gene is a gene that is a component of an amino acid biosynthetic pathway selected from the group consisting of:
   the serine biosynthesis pathway comprising genes of entry M00020;
   the threonine biosynthesis pathway comprising genes of KEGG entry M00018;
   the cysteine biosynthesis pathway comprising genes of KEGG entry M00021;
   the cysteine biosynthesis pathway comprising genes of KEGG entry M00338;
   the cysteine biosynthesis pathway comprising genes of KEGG entry M00609;
   the methionine biosynthesis pathway comprising genes of KEGG entry M00017;
   the valine/isoleucine biosynthesis pathway comprising genes of KEGG entry M00019;
   the isoleucine biosynthesis pathway comprising genes of KEGG entry M00535;
   the isoleucine biosynthesis pathway comprising genes of KEGG entry M00570;
   the leucine biosynthesis pathway comprising genes of KEGG entry M00432;
   the lysine biosynthesis pathway comprising genes of KEGG entry M00016;
   the lysine biosynthesis pathway comprising genes of KEGG entry M00525;
   the lysine biosynthesis pathway comprising genes of KEGG entry M00526;
   the lysine biosynthesis pathway comprising genes of KEGG entry M00527;
   the lysine biosynthesis pathway comprising genes of KEGG entry M0030;
   the lysine biosynthesis pathway comprising genes of KEGG entry M00433;
   the lysine biosynthesis pathway comprising genes of KEGG entry M0031;
   the proline biosynthesis pathway comprising genes of KEGG entry M00015;
   the ornithine biosynthesis pathway comprising genes of KEGG entry M00028;
   the ornithine biosynthesis pathway comprising genes of KEGG entry M00763;
   the histidine biosynthesis pathway comprising genes of KEGG entry M00026;
   the shikimate biosynthesis pathway comprising genes of KEGG entry M00022;
   the tryptophan biosynthesis pathway comprising genes of entry M00023;
   the phenylalanine biosynthesis pathway comprising genes of KEGG entry M00024;
   the tyrosine biosynthesis pathway comprising genes of KEGG entry M00025;
   the tyrosine biosynthesis pathway comprising genes of KEGG entry M00040;
   and combinations of the genes of any of the biosynthesis pathways thereof
6. The recombinant nucleic acid molecule according to embodiment 1, further comprising a one or more additional promoter polynucleotide sequences selected from the group consisting of SEQ ID NOs:1 to 8, each promoter functionally linked to at least one additional heterologous gene.
7. The recombinant nucleic acid molecule according to embodiment 1, wherein said recombinant nucleic acid molecule is isolated.
8. A recombinant vector comprising a promoter polynucleotide sequence selected from the group consisting of SEQ ID NOs:1 to 8, and combinations thereof, each promoter functionally linked to at least one heterologous target gene.
9. The recombinant vector according to embodiment 8, wherein said promoter polynucleotide sequence is selected from the group consisting of SEQ ID NOs:1, 5 and 7.
10. The recombinant vector according to embodiments 8 or 9, comprising a combination of two or more recombinant nucleic acid molecules comprising a promoter polynucleotide sequence selected from the group consisting of SEQ ID NOs:1 to 8, and combinations thereof, each promoter functionally linked to at least one heterologous target gene.
11. The recombinant vector according to embodiment 10, wherein each of said promoter polynucleotide sequences is functionally linked to a different heterologous target gene.
12. The recombinant vector according to embodiment 11, wherein said target genes are part of the same metabolic pathway.
13. The recombinant vector according to embodiment 11, wherein the target genes are not part of the same metabolic pathway.
14. A host cell comprising a recombinant nucleic acid molecule according to any one of embodiments 1 to 6, or a combination thereof according to embodiment 10, or the recombinant vector according to any one of embodiments 8 to 13.
15. The host cell according to embodiment 14, comprising a combination of promoter polynucleotide sequences, wherein each of said promoter polynucleotide sequences is functionally linked to a different heterologous target gene.
16. The host cell according to embodiment 15, wherein each of said different heterologous target genes are part of the same metabolic pathway.
17. The host cell according to embodiment 15, wherein each of said different heterologous target genes are not part of the same metabolic pathway.
18. The host cell according to any one of embodiments 14 to 17, which belongs to genus *Corynebacterium*.
19. The host cell according to embodiment 18, which is *Corynebacterium glutamicum*.
20. A method of modifying the expression of one or more target genes, comprising culturing a host cell according to any one of embodiments 12 to 19, wherein each of said one or more target genes are different heterologous target genes functionally linked to a polynucleotide sequence selected from the group consisting of SEQ ID NOs:1 to 8 and wherein the modification of expression of each heterologous target gene is independently selected from: up-regulating or down-regulating.
21. A method of modifying the expression of one or more target genes, comprising culturing a host cell according to any one of embodiments 12 to 19, wherein each of said one or more target genes are different heterologous target genes functionally linked to a polynucleotide sequence selected from the group consisting of SEQ ID NOs:1 to 8 and wherein the modification of expression of each heterologous target gene is independently selected from: up-regulating or down-regulating.
22. A method of producing a biomolecule comprising culturing a host cell according to any one of embodiments 12 to 19, under conditions suitable for producing the biomolecule.
23. The method according to embodiment 20, wherein said biomolecule is an L-amino acid.
24. The method according to embodiment 22, wherein said L-amino acid is L-lysine.
25. The method according to embodiment 20, wherein said at least one heterologous target gene is a gene encoding a protein selected from the group consisting of aspartate-semialdehyde dehydrogenase (EC:1.2.1.11); 4-hydroxy-tetrahydrodipicolinate synthase (EC:4.3.3.7); dihydrodipicolinate reductase (EC:1.17.1.8); 2,3,4,5-tetrahydropyridine-2-carboxylate N-succinyltransferase (EC:2.3.1.117); 2,3,4,5-tetrahydropyridine-2-carboxylate N-succinyltransferase (EC:2.3.1.117); N-succinyl-diaminopimelate aminotransferase (EC:2.6.1.17); succinyl-diaminopimelate desuccinylase (EC:3.5.1.18); diaminopimelate epimerase (EC:5.1.1.7); diaminopimelate decarboxylase (EC:4.1.1.20); diaminopimelate dehydrogenase (EC:1.4.1.16); Aspartokinase Lysc Alpha And Beta Subunits (EC:2.7.2.4); Aspartate Aminotransferase (EC:2.6.1.1); Phosphotransferase System (PTS); Glucose-Specific Enzyme II BC Component Of PTS (EC:2.7.1.69); glucose-6-phosphate 1-dehydrogenase (EC:1.1.1.49 1.1.1.363); glucose-6-phosphate isomerase (EC:5.3.1.9); transketolase (EC:2.2.1.1); 6-phosphofructokinase 1 (EC:2.7.1.11); phosphoenolpyruvate carboxylase (EC:4.1.1.31); pyruvate carboxylase (EC:6.4.1.1); isocitrate dehydrogenase (EC:1.1.1.42); phosphoenolpyruvate carboxykinase (GTP) (EC:4.1.1.32); Oxaloacetate decarboxylase (EC 4.1.1.3); homoserine kinase (EC:2.7.1.39); homoserine dehydrogenase (EC:1.1.1.3); threonine synthase (EC:4.2.3.1), and combinations thereof.
26. A host cell comprising at least one promoter polynucleotide functionally linked to a heterologous target gene; wherein the promoter polynucleotide comprises a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, and SEQ ID NO:8.
27. The host cell according to embodiment 25, comprising a combination of two or more promoter polynucleotide sequences functionally linked to a heterologous target gene wherein each promoter polynucleotide is functionally linked to a different heterologous target gene.
28. The host cell according to embodiment 26, wherein said combination comprises two heterologous target genes selected from the group consisting of aspartate-semialdehyde dehydrogenase (EC:1.2.1.11); 4-hydroxy-tetrahydrodipicolinate synthase (EC:4.3.3.7); dihydrodipicolinate reductase (EC:1.17.1.8); 2,3,4,5-tetrahydropyridine-2-carboxylate N-succinyltransferase (EC:2.3.1.117); 2,3,4,5-tetrahydropyridine-2-carboxylate N-succinyltransferase (EC:2.3.1.117); N-succinyl-diaminopimelate aminotransferase (EC:2.6.1.17); succinyl-diaminopimelate desuccinylase (EC:3.5.1.18); diaminopimelate epimerase (EC:5.1.1.7); diaminopimelate decarboxylase (EC:4.1.1.20); diaminopimelate dehydrogenase (EC:1.4.1.16); Aspartokinase Lysc Alpha And Beta Subunits (EC:2.7.2.4); Aspartate Aminotransferase (EC:2.6.1.1); Phosphotransferase System (PTS); Glucose-Specific Enzyme II BC Component Of PTS (EC: 2.7.1.69); glucose-6-phosphate 1-dehydrogenase (EC: 1.1.1.49 1.1.1.363); glucose-6-phosphate isomerase (EC: 5.3.1.9); transketolase (EC:2.2.1.1); 6-phosphofructokinase 1 (EC:2.7.1.11); phosphoenolpyruvate carboxylase (EC:4.1.1.31); pyruvate carboxylase (EC:6.4.1.1); isocitrate dehydrogenase (EC: 1.1.1.42); phosphoenolpyruvate carboxykinase (GTP) (EC:4.1.1.32); Oxaloacetate decarboxylase (EC 4.1.1.3); homoserine kinase (EC:2.7.1.39); homoserine dehydrogenase (EC:1.1.1.3); and threonine synthase (EC:4.2.3.1), each functionally linked to a promoter selected from the group consisting of SEQ ID NOs:1 to 8.

29. The host cell according to embodiment 27, wherein said combination comprises a promoter selected from the group consisting of SEQ ID NOs: 1, 5 and 7 functionally linked to said heterologous target genes.

30. The host cell according to embodiment 26, wherein said combination comprises three heterologous target genes selected from the group consisting of aspartate-semialdehyde dehydrogenase (EC:1.2.1.11); 4-hydroxy-tetrahydrodipicolinate synthase (EC:4.3.3.7); dihydrodipicolinate reductase (EC:1.17.1.8); 2,3,4,5-tetrahydropyridine-2-carboxylate N-succinyltransferase (EC:2.3.1.117); 2,3,4,5-tetrahydropyridine-2-carboxylate N-succinyltransferase (EC:2.3.1.117); N-succinyldiaminopimelate aminotransferase (EC:2.6.1.17); succinyl-diaminopimelate desuccinylase (EC:3.5.1.18); diaminopimelate epimerase (EC:5.1.1.7); diaminopimelate decarboxylase (EC:4.1.1.20); diaminopimelate dehydrogenase (EC:1.4.1.16); Aspartokinase Lysc Alpha And Beta Subunits (EC:2.7.2.4); Aspartate Aminotransferase (EC:2.6.1.1); Phosphotransferase System (PTS); Glucose-Specific Enzyme II BC Component Of PTS (EC: 2.7.1.69); glucose-6-phosphate 1-dehydrogenase (EC: 1.1.1.49 1.1.1.363); glucose-6-phosphate isomerase (EC: 5.3.1.9); transketolase (EC:2.2.1.1); 6-phosphofructokinase 1 (EC:2.7.1.11); phosphoenolpyruvate carboxylase (EC:4.1.1.31); pyruvate carboxylase (EC:6.4.1.1); isocitrate dehydrogenase (EC: 1.1.1.42); phosphoenolpyruvate carboxykinase (GTP) (EC:4.1.1.32); Oxaloacetate decarboxylase (EC 4.1.1.3); homoserine kinase (EC:2.7.1.39); homoserine dehydrogenase (EC:1.1.1.3); and threonine synthase (EC:4.2.3.1), each functionally linked to a promoter selected from the group consisting of SEQ ID NOs:1 to 8.

31. The host cell according to embodiment 29, wherein said combination comprises a promoter selected from the group consisting of SEQ ID NOs: 1, 5 and 7 functionally linked to said heterologous target genes.

32. The host cell according to embodiment 26, wherein said heterologous target genes are part of the same metabolic pathway.

33. The host cell according to embodiment 26, wherein said heterologous target genes are not part of the same metabolic pathway.

34. The host cell according to any one of embodiments 25 to 32, which belongs to genus *Corynebacterium*.

35. The host cell according to any one of embodiments 25 to 33, which is *Corynebacterium glutamicum*.

36. A method of modifying the expression of one or more target genes, comprising culturing a host cell according to any one of embodiments 25 to 34, wherein the modification of each heterologous target gene is independently selected from: up-regulating or down-regulating, wherein said up-regulating or down-regulating is relative to the level of expression of said target gene under the control of the endogenous promoter.

37. A method of producing a biomolecule comprising culturing a host cell according to any one of embodiments 25 to 35, under conditions suitable for producing the biomolecule.

38. The method according to embodiment 36, wherein said biomolecule is an L-amino acid.

39. The method according to embodiment 37, wherein said L-amino acid is L-lysine.

40. The method according to embodiment 38, wherein said at least one heterologous target gene is selected from the group consisting of aspartate-semialdehyde dehydrogenase (EC:1.2.1.11); 4-hydroxy-tetrahydrodipicolinate synthase (EC:4.3.3.7); dihydrodipicolinate reductase (EC: 1.17.1.8); 2,3,4,5-tetrahydropyridine-2-carboxylate N-succinyltransferase (EC:2.3.1.117); 2,3,4,5-tetrahydropyridine-2-carboxylate N-succinyltransferase (EC: 2.3.1.117); N-succinyldiaminopimelate aminotransferase (EC:2.6.1.17); succinyl-diaminopimelate desuccinylase (EC:3.5.1.18); diaminopimelate epimerase (EC:5.1.1.7); diaminopimelate decarboxylase (EC:4.1.1.20); diaminopimelate dehydrogenase (EC:1.4.1.16); Aspartokinase Lysc Alpha And Beta Subunits (EC:2.7.2.4); Aspartate Aminotransferase (EC:2.6.1.1); Phosphotransferase System (PTS); Glucose-Specific Enzyme II BC Component Of PTS (EC:2.7.1.69); glucose-6-phosphate 1-dehydrogenase (EC:1.1.1.49 1.1.1.363); glucose-6-phosphate isomerase (EC:5.3.1.9); transketolase (EC: 2.2.1.1); 6-phosphofructokinase 1 (EC:2.7.1.11); phosphoenolpyruvate carboxylase (EC:4.1.1.31); pyruvate carboxylase (EC:6.4.1.1); isocitrate dehydrogenase (EC: 1.1.1.42); phosphoenolpyruvate carboxykinase (GTP) (EC:4.1.1.32); Oxaloacetate decarboxylase (EC 4.1.1.3); homoserine kinase (EC:2.7.1.39); homoserine dehydrogenase (EC:1.1.1.3); threonine synthase (EC:4.2.3.1), and combinations thereof.

41. A recombinant vector comprising at least one promoter polynucleotide functionally linked to a heterologous target gene; wherein the promoter polynucleotide comprises a sequence selected from: SEQ ID NO:1, SEQ ID NO:2, SEQ ID NO:3, SEQ ID NO:4, SEQ ID NO:5, SEQ ID NO:6, SEQ ID NO:7, and SEQ ID NO:8; wherein when the promoter polynucleotide comprises a sequence selected from: SEQ ID NO:2, SEQ ID NO:3, SEQ ID NO:4, SEQ ID NO:6, or SEQ ID NO:8, the target gene is other than the promoter polynucleotide's endogenous gene.

42. The recombinant vector according to embodiment 40, comprising at least two promoter polynucleotides, wherein each promoter polynucleotide is functionally linked to a different target gene.

43. The recombinant vector according to embodiment 41, wherein the target genes are part of the same metabolic pathway.

44. The recombinant vector according to embodiment 42, wherein the target genes are not part of the same metabolic pathway.

45. A host cell transformed with the recombinant vector according to any one of embodiments 40 to 43.

46. The host cell according to embodiment 44, which belongs to genus *Corynebacterium*.

47. The host cell according to embodiment 46, which is *Corynebacterium glutamicum*.

48. A method of modifying the expression of one or more target genes, comprising culturing a host cell according to any one of embodiments 44 to 46, wherein the modification of each target gene is independently selected from: up-regulating and down-regulating.

49. A method of producing a biomolecule comprising culturing a host cell according to any one of embodiments 44 to 47, under conditions suitable for producing the biomolecule.

50. The method according to embodiment 48, wherein said biomolecule is an L-amino acid.

The following examples are provided for purposes of illustration, not limitation.

EXAMPLES

Example 1: Identification of Candidate Promoters

The following procedure was used to identify native *C. glutamicum* promoters that satisfied both of the following criteria: 1) represented a ladder of constitutive promoters; and 2) could be encoded by short DNA sequences, ideally less than 100 base pairs. A published data set describing global gene expression levels in *C. glutamicum* ATCC 13032 (Lee et al., Biotechnology Letters, 2013) was examined to identify genes that were constitutively expressed across different growth conditions. Genes whose expression level remained constant (defined as a ratio of expression between 0.33 and 3) across two growth conditions, namely chemostat growth in minimal media with and without the addition of hydrogen peroxide satisfied the first criterion. A published data set describing the *C. glutamicum* ATCC 13032 transcriptome (Pfeifer-Sancar et al., BMC Genomics 2013, 14:888) was examined to find genes with compact promoters, i.e. those consisting of a 60 base pair core promoter region and a 5 prime untranslated region between 26 and 40 base pairs in length. The two data sets were cross-referenced to identify promoters that satisfied both criteria. See FIG. 1. Five candidate promoters (SEQ ID NOs: 2, 3, 4, 6, and 8) were selected for further evaluation.

Example 2: Evaluation of Candidate Promoter Activity

To evaluate candidate promoter activity, a set of plasmid based fluorescence reporter constructs was designed. Briefly, each promoter was cloned in front of eyfp, a gene encoding yellow fluorescent protein in the shuttle vector pK18rep. These plasmids were transformed into *C. glutamicum* NRRL B-11474 and promoter activity was assessed by measuring the accumulation of YFP protein by spectrometry.

The shuttle vector pK18rep was constructed by replacing the sacB gene in pK18mobSacB (ATCC 87087) with the pBL1 origin of replication (GenBank: AF092037.1) resulting in a vector able to propagate in both *E. coli* and *C. glutamicum*. Briefly, we PCR amplified a portion of pK18mobSacB containing the *E. coli* origin of replication and the Kanamycin resistance gene nptII using the primers pK18F (TCATGACCAAAATCCCTTAACGTG (SEQ ID NO:9)) and pK18R (GCGTACTCTTCGATGGTGAAAACATCTC (SEQ ID NO:10)) and PCR amplified synthetic DNA encoding the pBL1 origin of replication with the primers pBL1F (GACCTAAAATGTGTAAAGGGCAAAGTGTATACaacaacaagacccatcatagtttgc (SEQ ID NO:11)) and pBL1R (CACGTTAAGGGATTTTGGTCATGAcacatgcagtcatgtcgtgc (SEQ ID NO:12)). The PCR products were treated with DpnI (New England Biolabs) when appropriate, purified with DNA Clean & Concentrate-5 (Zymo Research), and assembled using the Gibson Assembly method with Gibson Assembly Master Mix (NEB) according to manufactures instructions. The Gibson Assembly reaction was transformed into NEB Turbo competent cells (New England Biolabs) according to the manufactures instructions. Transformants were selected on LB agar plus 25 μg/mL Kanamycin and verified by Sanger sequencing.

The reporter construct pK18rep-Psod-eyfp was constructed by restriction digestion and ligation of pK18rep and a synthetic DNA construct consisting of 191 base pair DNA sequence that encodes the superoxide disumutase (GenBank: BA000036.3) promoter from *C. glutamicum* ATCC 13032 upstream of eyfp gene followed by a 77 base pair DNA sequence encoding the sod terminator from *C. glutamicum* ATCC 13032 flanked by EcoRI and SalI restriction sites. The parent vector and synthetic DNA insert were digested with EcoRI-HF and SalI-HF (New England Biolabs) and the resulting products were run on an agarose gel. The DNA was extracted from the gel and purified using the Zymoclean Gel DNA Recovery Kit (Zymo Research) and ligated with T4 DNA ligase (New England Biolabs) according to the manufactures instructions. The ligation reaction was transformed into NEB Turbo competent cells (New England Biolabs) according to the manufactures instructions. Transformants were selected on LB agar plus 25 μg/mL Kanamycin and verified by Sanger sequencing.

Additional promoter reporter constructs were constructed by replacing the sod promoter in pK18rep-Psod-eyfp. We PCR amplified pK18rep-Psod-eyfp excluding the sod promoter with primers pK18repR (gcttgcatgcctgcaggtcga (SEQ ID NO:13)) and yfpF (ATGGTGAGCAAGGGCGAGGAGC (SEQ ID NO:14)). The PCR product was treated with DpnI (New England Biolabs) and purified with DNA Clean & Concentrate-5 (Zymo Research) and assembled with synthetic DNA constructs encoding the promoter of interest plus 25 base pair homology sequence to the destination vector using the Gibson Assembly method with Gibson Assembly Master Mix (NEB) according to manufactures instructions. The Gibson Assembly reaction was transformed into NEB Turbo competent cells (New England Biolabs) according to the manufacturer's instructions. Transformants were selected on LB agar plus 25 μg/mL Kanamycin and verified by Sanger sequencing.

Additionally, the strong constitutive promoter Pcg0007 (SEQ ID NO:2) was chosen for mutagenesis. In *C. glutamicum*, the −10 element is thought to play a key role in determining promoter activity (Pfeifer-Sancar et al., BMC Genomics 2013, 14:888) therefore four out of six positions in predicted −10 element (TAAGAT) of Pc0007 were randomized in order to generate both stronger and attenuated promoter variants (SEQ ID NOs 1, 5, and 7). This library was generated by PCR amplifying pK18rep-Pc0007-eyfp with Pcg0007Fwd (GGAAACGTCTGTATCGGATAAGTAG (SEQ ID NO:15)) and Pc0007Rev (CTACTTATCCGATACAGACGTTTCCANNNNACACGCTTAGGTCCCCACGTAGTACCA (SEQ ID NO:16)), treated with DpnI (New England Biolabs) and assembled using the Gibson Assembly method with Gibson Assembly Master Mix (NEB) according to manufactures instructions. The Gibson Assembly reaction was transformed into NEB Turbo competent cells (New England Biolabs) according to the manufacturer's instructions. Transformants were selected on LB agar plus 25 μg/mL Kanamycin and individual colonies were characterized by Sanger sequencing. Colonies were pooled by scraping the agar and purified plasmid DNA was isolated using the Zyppy minipred kit (Zymo Research).

Figure 2:
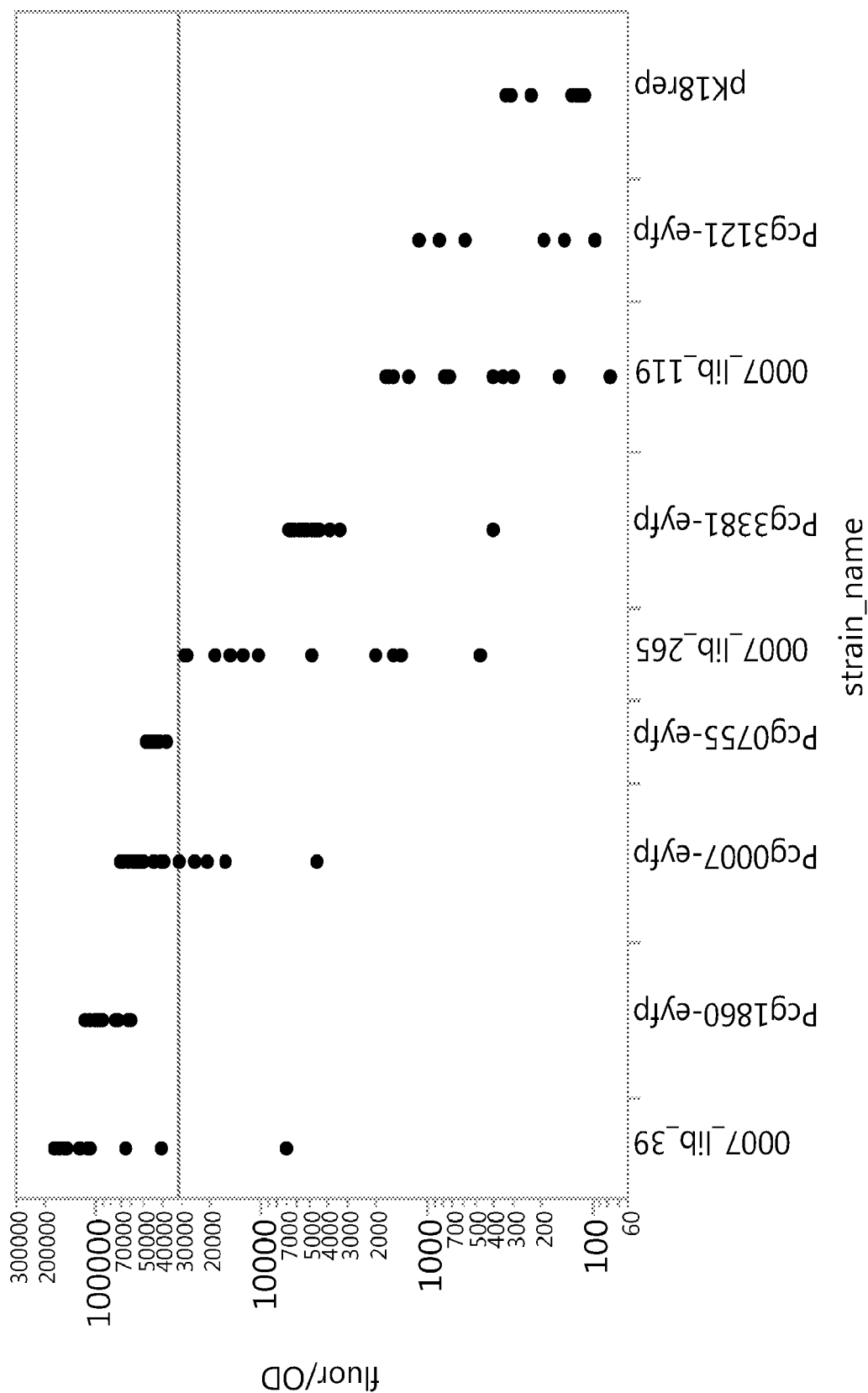
FIG. 2 shows a graph of normalized activity (x axis) of eight candidate promoters (y axis) in a yellow fluorescent protein-based assay. Each biological replicate of each candidate promoter is represented by a black circle. The parent plasmid pK18rep acted as a negative control.

Purified reporter construct plasmids were transformed into *C. glutamicum* NRRL B-11474 by electroporation (Haynes et al., Journal of General Microbiology, 1990). Transformants were selected on BHI agar plus 25 µg/mL Kanamycin. For each transformation, multiple single colonies were picked and inoculated into individual wells of a 96 mid-well block containing 300 µL of BHI media plus 25 µg/mL Kanamycin. The cells were grown to saturation by incubation for 48 h at 30° C. shaking at 1,000 rpm. After incubation, cultures were centrifuged for 5 min at 3,500 rpm and the media was removed by aspiration. Cells were washed once by resuspension in 300 µL of PBS and centrifugation for 5 min at 3,500 rpm followed by aspiration of the supernatant and a final resuspension in 300 µL of PBS. A 20 µL aliquot of this mixture was transferred to a 96-well full area black clear bottom assay plate containing 180 µL of PBS. The optical density of the cells at 600 nm was measured with the SpectraMax M5 microplate reader and the fluorescence was measured with the TECAN M1000 microplate leader by exciting at 514 nm and measuring emission at 527 nm. For each well a normalized fluorescence activity was calculated by dividing fluorescence by optical density. The parent plasmid pK18rep acted as a negative control. Normalized fluorescence activity was compared between reporter constructs and between biological replicates (FIG. 2). A numerical summary of promoter activity is presented in Table 5 below.

locus. Upon recombination, the endogenous promoter is replaced by the promoter of SEQ ID NOs: 1 to 8 functionally linked to the respective target gene in the endogenous *C. glutamican* locus. A variety of targeting vectors comprising the promoter and functionally linked target gene included a range of homology direct repeat arm lengths ranging from 0.5 Kb, 1 Kb, 2 Kb, and 5 Kb. Each DNA insert was produced by PCR amplification of homologous regions using commercially sourced oligos and the host strain genomic DNA described above as template. The promoter to be introduced into the genome was encoded in the oligo tails. PCR fragments were assembled into the vector backbone using homologous recombination in yeast.

Vectors are initially transformed into *E. coli* using standard heat shock transformation techniques and correctly assembled clones are identified and validated. Transformed *E. coli* bacteria are tested for assembly success. Four colonies from each *E. coli* transformation plate are cultured and tested for correct assembly via PCR. Vectors are amplified in the *E. coli* hosts to provide vector DNA for *Corynebacterium* transformation.

Validated clones are transformed into *Corynebacterium glutamicum* host cells via electroporation. For each transformation, the number of Colony Forming Units (CFUs) per µg of DNA is determined as a function of the insert size. Coryne genome integration is analyzed as a function of homology arm length. Shorter arms had a lower efficiency.

TABLE 5

Recombinant *C. glutamicum* Expressing Yellow Fluorescent Protein Under the Control of Promoters

| Strain | SEQ ID NO | No. of Replicates | Mean Activity | Standard Deviation | Standard Error of Mean | 95% Confidence Interval | Relative Expression |
|---|---|---|---|---|---|---|---|
| 0007_lib_39 | 1 | 12 | 114402 | 52987.9 | 15296 | 80735-148069 | 1167 |
| Pcg1860-eyfp | 2 | 19 | 89243 | 16162.2 | 3708 | 81453-97033 | 911 |
| Pcg0007-eyfp | 3 | 19 | 44527 | 18110.3 | 4155 | 35798-53256 | 454 |
| Pcg0755-eyfp | 4 | 10 | 43592 | 3643 | 1152 | 40986-46198 | 445 |
| 0007_lib_265 | 5 | 11 | 11286 | 10459.4 | 3154 | 4260-18313 | 115 |
| Pcg3381-eyfp | 6 | 19 | 4723 | 1854.3 | 425 | 3829-5617 | 48 |
| 0007_lib_119 | 7 | 18 | 661 | 731.9 | 173 | 297-1025 | 7 |
| Pcg3121-eyfp | 8 | 14 | 98 | 537.5 | 144 | −212-409 | 1 |
| pK18rep | — | 20 | −45 | 214.9 | 48 | −145-56 | |

Figure 3:
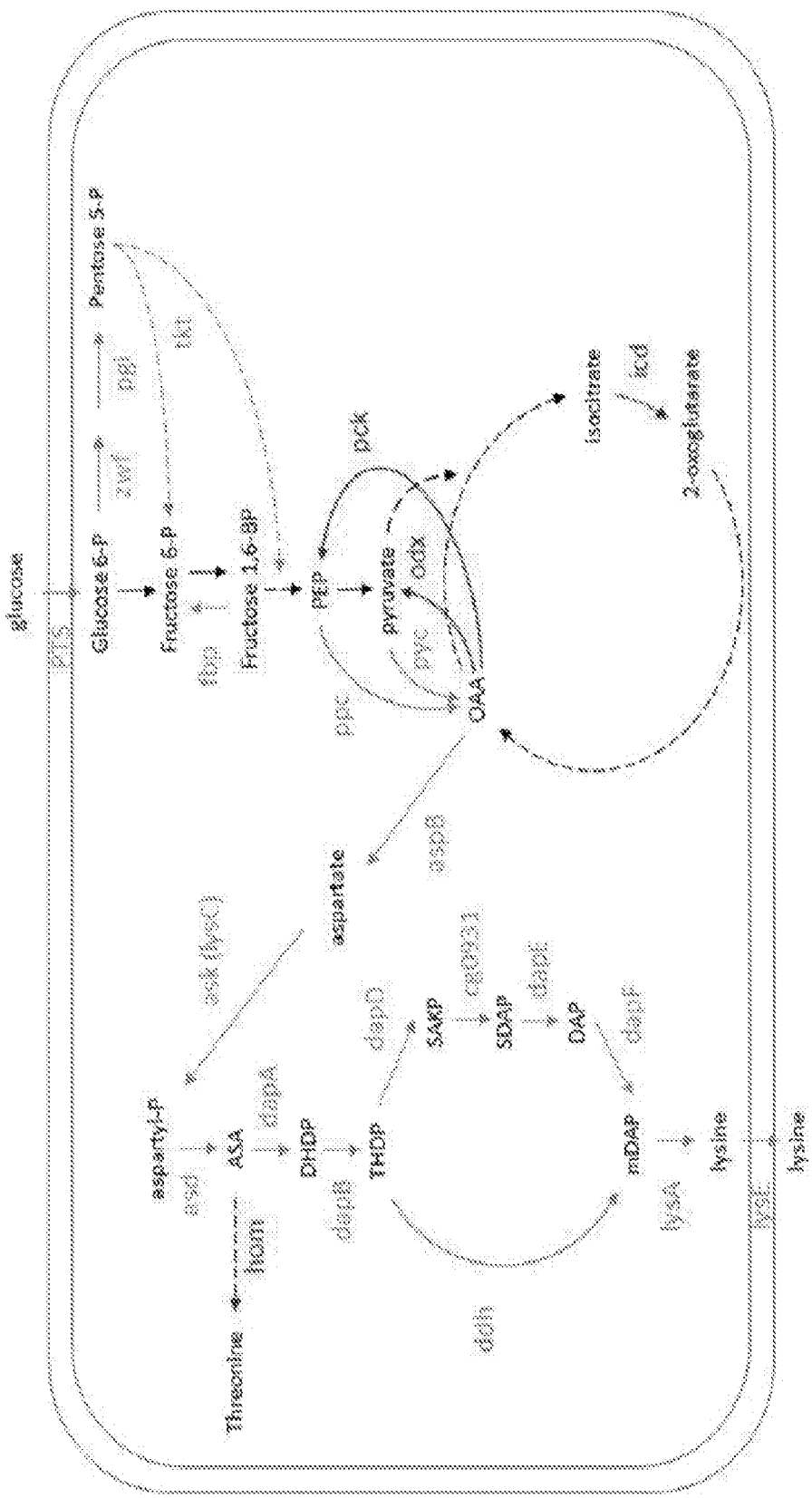
FIG. 3 presents a diagram of the genetic and biochemical pathway for the biosynthesis of the amino acid L-lysine. Genes that divert intermediates in the biosynthetic pathway (e.g., pck, odx, icd, and hom) are underlined.

Example 3: Application of Candidate Promoters to the L-Lysine Biosynthetic Pathway The promoters of the present disclosure are useful for improved processes for the production of biomolecules in host cells. An example of the application and use of the promotor of the present disclosure is directed to the production of the amino acid L-lysine. FIG. 3 presents the biosynthetic pathway for the production of L-lysine and includes the genes pck, odx, icd, and hom (e.g., the homoserine/threonine synthase pathway), that divert intermediates from the pathway leading to reductions in overall L-lysine yield. The symbols, gene names, Enzyme Commission number (EC number), and map position in *C. glutamicum* strain ATCC 13032 are provided below in Table 3.

Recombinant vectors comprising a promoter of SEQ ID NOs: 1 to 8 functionally linked to a target gene as provided in Table 3 are cloned into *Corynebacterium* cloning vectors using yeast homologous recombination cloning techniques to assemble a vector in which each promoter was flanked by direct repeat regions to provide for homologous recombination in *Corynebacterium glutamican* at the target gene locus.

Cultures of *Corynebacterium* identified as having successful integrations of the insert cassette are cultured on media containing 5% sucrose to counter select for loop outs of the sacb selection gene. Sucrose resistance frequency for various homology direct repeat arms do not vary significantly with arm length. These results suggest that loopout efficiencies remain steady across homology arm lengths of 0.5 kb to 5 kb.

In order to further validate loop out events, colonies exhibiting sucrose resistance are cultured and analyzed via sequencing. The results for the sequencing of the insert genomic regions are summarized below in Table 6.

TABLE 6

Loop-out Validation Frequency

| Outcome | Frequency (sampling error 95% confidence) |
|---|---|
| Successful Loop out | 13% (9%/20%) |

TABLE 6-continued

Loop-out Validation Frequency

| Outcome | Frequency (sampling error 95% confidence) |
| --- | --- |
| Loop Still present | 42% (34%/50%) |
| Mixed read | 44% (36%/52%) |

Sequencing results show a 10-20% efficiency in loop outs. Not to be limited by any particular theory, loop-out may be dependent on insert sequence. Even if correct, picking 10-20 sucrose-resistant colonies leads to high success rates.

Upon integration, the recombinant vectors replace the endogenous promoter sequences with a promoter selected from the group consisting of Pcg1860 (SEQ ID NO:2), Pcg0007 (SEQ ID NO:3), Pcg0755 (SEQ ID NO:4), Pcg0007_lib_265 (SEQ ID NO:5), Pcg3381 (SEQ ID NO:6), Pcg007_lib_119 (SEQ ID NO:7), and Pcg3121 (SEQ ID NO:8). A list of the resulting recombinant strains is provided below in Table 7.

Multiple single colonies (N in Table 7) are picked, inoculated and grown as a small scale culture. Each newly created strain comprising a test promoter is tested for lysine yield in small scale cultures designed to assess product titer performance. Small scale cultures are conducted using media from industrial scale cultures. Product titer is optically measured at carbon exhaustion (i.e., representative of single batch yield) with a standard colorimetric assay. Briefly, a concentrated assay mixture is prepared and is added to fermentation samples such that final concentrations of reagents are 160 mM sodium phosphate buffer, 0.2 mM Amplex Red, 0.2 U/mL Horseradish Peroxidase and 0.005 U/mL of lysine oxidase. Reactions proceed to completion and optical density is measured using a Tecan M1000 plate spectrophotometer at a 560 nm wavelength.

As shown in Table 7, the yield of L-lysine is increased by over 24% (e.g., recombinant strain 7000007840) over the non-engineered strain. In other embodiments, the yield of L-lysine is decreased by nearly 90% (e.g., recombinant strain 700000773). As provided in Table 7, replacement of the promoter for the pgi and zwf results in greater than 10% improvements to L-lysine production.

Figure 4:
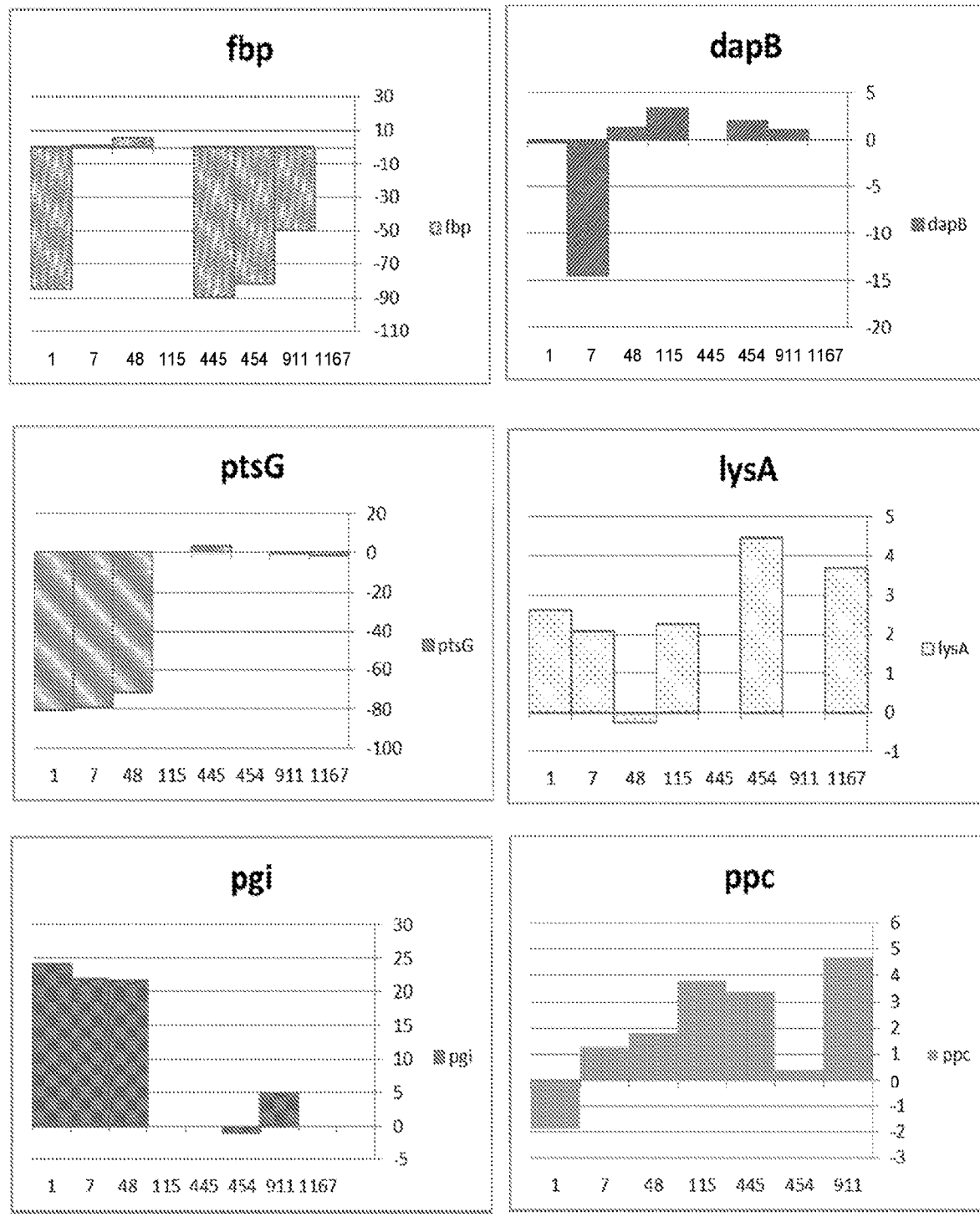
FIG. 4 presents a graph of the results of exemplary embodiments according to the present specification of changes to L-lysine production in host cells of *C. glutamicum* transformed with recombinant nucleic acid molecules having promoter polynucleotide sequences selected from the group consisting of SEQ ID NOs:1 to 8 functionally linked to the heterologous target genes fbp, dapB, ptsG, lysA, pgi, and ppc, from *C. glutamicum*.
Figure 5:
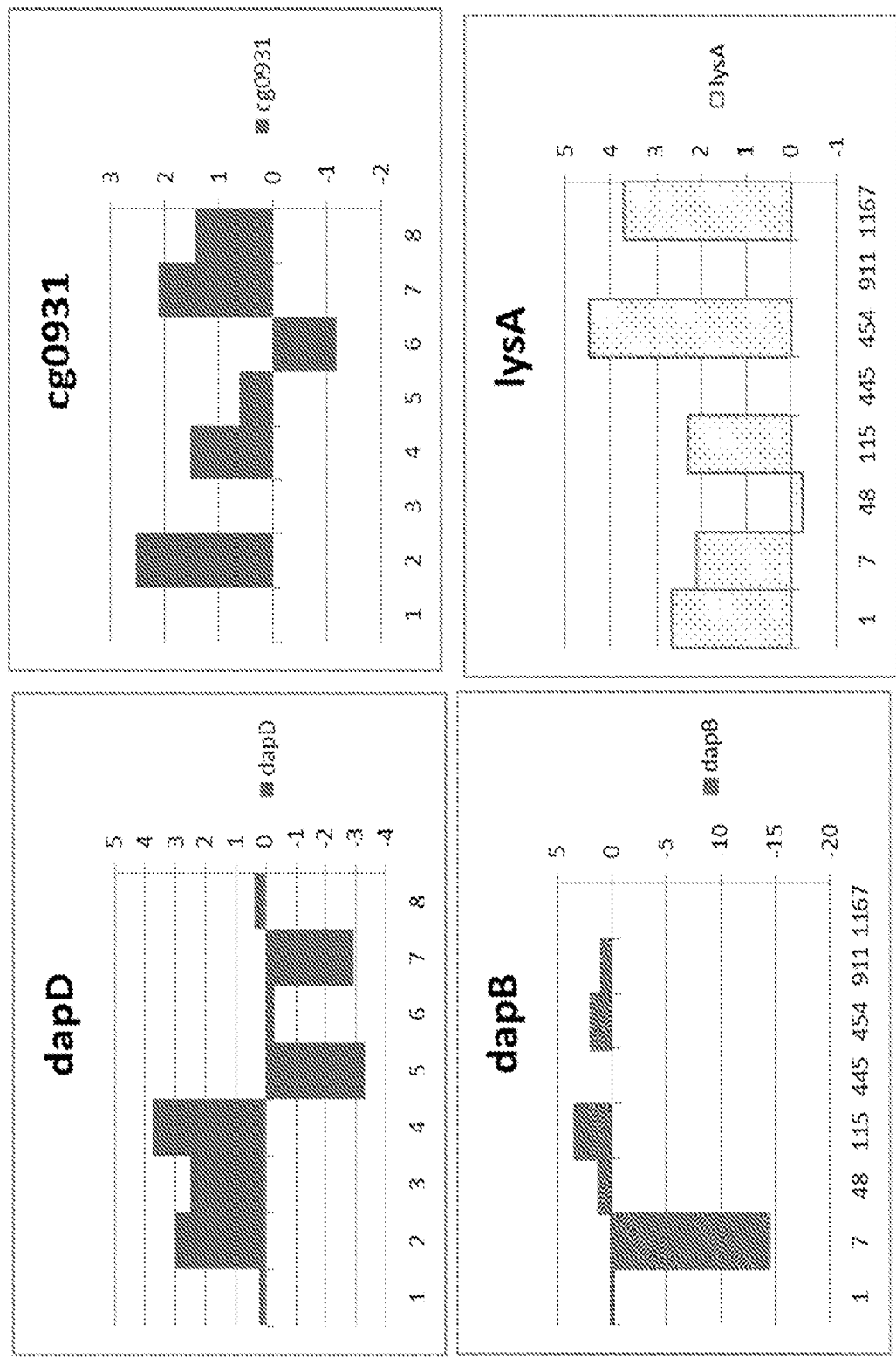
FIG. 5 presents a graph of the results of exemplary embodiments according to the present specification of changes to L-lysine production in host cells of *C. glutamicum* transformed with recombinant nucleic acid molecules having promoter polynucleotide sequences selected from the group consisting of SEQ ID NOs:1 to 8 functionally linked to the heterologous target genes dapS, cg0931, DapB, and lysA, from *C. glutamicum*.

Notably, the production of L-lysine is not a simple dependence on incorporating the most active promoters. As illustrated in FIG. 4, lysine yield is maximized by a relatively weak promoter (e.g., pgi having relative promoter expression of 1, 7x, or 48x, or dapB at a relative promoter strength of 7x) or maximized by intermediate expression (e.g., lysA at having a relative promoter expression of 454x). In certain cases, expression is maximal when the relative promoter strength is maximized (e.g., ppc). As exemplified in FIG. 5, the location of the gene in the genetic pathway (FIG. 3) does not reliably predict the relative increase or decrease in L-lysine yield or the optimal promoter strength. For example, high level expression of cg0931 results in improved yield while higher levels of dapD result in no improvement or decreased yield.

TABLE 7

Recombinant strains of C. glutamicum having modified expression of L-lysine Biosynthetic Genes

| Strain | promoter-target | N | Mean ($A_{560}$) | Std Error | % Yield Change From Base |
| --- | --- | --- | --- | --- | --- |
| 7000007713 | Pcg1860-asd | 8 | 0.84595 | 0.00689 | 3.927615 |
| 7000007736 | Pcg0755-asd | 4 | 0.84036 | 0.00974 | 3.240866 |
| 7000007805 | Pcg0007_119-asd | 8 | 0.82493 | 0.00689 | 1.345242 |
| 7000007828 | Pcg3121-asd | 8 | 0.8246 | 0.00689 | 1.3047 |
| 7000007759 | Pcg0007_265-asd | 8 | 0.81155 | 0.00689 | −0.29853 |
| 7000007782 | Pcg3381-asd | 8 | 0.8102 | 0.00689 | −0.46438 |
| 7000007712 | Pcg1860-ask | 8 | 0.83958 | 0.00689 | 3.14504 |
| 7000007735 | Pcg0755-ask | 8 | 0.81673 | 0.00689 | 0.337846 |
| 7000007827 | Pcg3121-ask | 8 | 0.81498 | 0.00689 | 0.122853 |
| 7000007804 | Pcg0007_119-ask | 8 | 0.81492 | 0.00689 | 0.115482 |
| 7000007758 | Pcg0007_265-ask | 8 | 0.80381 | 0.00689 | −1.24942 |
| 7000007781 | Pcg3381-ask | 8 | 0.80343 | 0.00689 | −1.2961 |
| 7000007780 | Pcg3381-aspB | 8 | 0.84072 | 0.00689 | 3.285093 |
| 7000007803 | Pcg0007_119-aspB | 8 | 0.82106 | 0.00689 | 0.8698 |
| 7000007809 | Pcg0007_119-cg0931 | 8 | 0.83446 | 0.00689 | 2.516032 |
| 7000007717 | Pcg1860-cg0931 | 4 | 0.83129 | 0.00974 | 2.126588 |
| 7000007763 | Pcg0007_265-cg0931 | 4 | 0.82628 | 0.00974 | 1.511094 |
| 7000007671 | Pcg0007_39-cg0931 | 8 | 0.82554 | 0.00689 | 1.420182 |
| 7000007740 | Pcg0755-cg0931 | 8 | 0.81921 | 0.00689 | 0.642522 |
| 7000007694 | Pcg0007-cg0931 | 8 | 0.80444 | 0.00689 | −1.17202 |
| 7000007691 | Pcg0007-dapA | 8 | 0.8299 | 0.00689 | 1.955822 |
| 7000007783 | Pcg3381-dapA | 8 | 0.80951 | 0.00689 | −0.54915 |
| 7000007760 | Pcg0007_265-dapA | 8 | 0.76147 | 0.00689 | −6.45102 |
| 7000007806 | Pcg0007_119-dapA | 8 | 0.35394 | 0.00689 | −56.5174 |
| 7000007761 | Pcg0007_265-dapB | 8 | 0.84157 | 0.00689 | 3.389518 |
| 7000007738 | Pcg0755-dapB | 4 | 0.84082 | 0.00974 | 3.297378 |
| 7000007692 | Pcg0007-dapB | 8 | 0.83088 | 0.00689 | 2.076218 |
| 7000007784 | Pcg3381-dapB | 8 | 0.82474 | 0.00689 | 1.3219 |
| 7000007715 | Pcg1860-dapB | 8 | 0.82232 | 0.00689 | 1.024595 |
| 7000007830 | Pcg3121-dapB | 8 | 0.81236 | 0.00689 | −0.19902 |
| 7000007807 | Pcg0007_119-dapB | 4 | 0.69622 | 0.00974 | −14.4672 |
| 7000007762 | Pcg0007_265-dapD | 8 | 0.84468 | 0.00689 | 3.771591 |
| 7000007808 | Pcg0007_119-dapD | 8 | 0.83869 | 0.00689 | 3.035701 |
| 7000007785 | Pcg3381-dapD | 8 | 0.83397 | 0.00689 | 2.455834 |
| 7000007670 | Pcg0007_39-dapD | 8 | 0.81698 | 0.00689 | 0.368559 |
| 7000007831 | Pcg3121-dapD | 4 | 0.8155 | 0.00974 | 0.186737 |

TABLE 7-continued

Recombinant strains of C. glutamicum having modified expression of L-lysine Biosynthetic Genes

| Strain | promoter-target | N | Mean ($A_{560}$) | Std Error | % Yield Change From Base |
|---|---|---|---|---|---|
| 7000007693 | Pcg0007-dapD | 8 | 0.8117 | 0.00689 | −0.28011 |
| 7000007716 | Pcg1860-dapD | 8 | 0.79044 | 0.00689 | −2.89196 |
| 7000007739 | Pcg0755-dapD | 8 | 0.78694 | 0.00689 | −3.32195 |
| 7000007787 | Pcg3381-dapE | 8 | 0.83814 | 0.00689 | 2.968132 |
| 7000007833 | Pcg3121-dapE | 8 | 0.83721 | 0.00689 | 2.853878 |
| 7000007741 | Pcg0755-dapE | 8 | 0.83263 | 0.00689 | 2.291211 |
| 7000007810 | Pcg0007_119-dapE | 8 | 0.83169 | 0.00689 | 2.175729 |
| 7000007718 | Pcg1860-dapE | 8 | 0.81855 | 0.00689 | 0.561439 |
| 7000007672 | Pcg0007_39-dapE | 8 | 0.80932 | 0.00689 | −0.5725 |
| 7000007765 | Pcg0007_265-dapF | 8 | 0.8327 | 0.00689 | 2.299811 |
| 7000007788 | Pcg3381-dapF | 8 | 0.82942 | 0.00689 | 1.896853 |
| 7000007811 | Pcg0007_119-dapF | 8 | 0.82926 | 0.00689 | 1.877196 |
| 7000007696 | Pcg0007-dapF | 8 | 0.82099 | 0.00689 | 0.861201 |
| 7000007719 | Pcg1860-dapF | 8 | 0.82067 | 0.00689 | 0.821888 |
| 7000007673 | Pcg0007_39-dapF | 8 | 0.82062 | 0.00689 | 0.815745 |
| 7000007789 | Pcg3381-ddh | 8 | 0.84817 | 0.00689 | 4.200349 |
| 7000007835 | Pcg3121-ddh | 8 | 0.82141 | 0.00689 | 0.912799 |
| 7000007812 | Pcg0007_119-ddh | 8 | 0.82093 | 0.00689 | 0.853829 |
| 7000007674 | Pcg0007_39-ddh | 8 | 0.81494 | 0.00689 | 0.117939 |
| 7000007720 | Pcg1860-ddh | 8 | 0.81473 | 0.00689 | 0.09214 |
| 7000007766 | Pcg0007_265-ddh | 8 | 0.81427 | 0.00689 | 0.035627 |
| 7000007743 | Pcg0755-ddh | 8 | 0.80655 | 0.00689 | −0.9128 |
| 7000007697 | Pcg0007-ddh | 8 | 0.80621 | 0.00689 | −0.95457 |
| 7000007779 | Pcg3381-fbp | 8 | 0.85321 | 0.00689 | 4.819529 |
| 7000007802 | Pcg0007_119-fbp | 4 | 0.81425 | 0.00974 | 0.03317 |
| 7000007710 | Pcg1860-fbp | 4 | 0.40253 | 0.00974 | −50.5479 |
| 7000007687 | Pcg0007-fbp | 8 | 0.14881 | 0.00689 | −81.7182 |
| 7000007825 | Pcg3121-fbp | 4 | 0.12471 | 0.00974 | −84.679 |
| 7000007733 | Pcg0755-fbp | 4 | 0.08217 | 0.00974 | −89.9052 |
| 7000007746 | Pcg0755-hom | 8 | 0.81925 | 0.00689 | 0.647436 |
| 7000007792 | Pcg3381-hom | 4 | 0.77674 | 0.00974 | −4.57505 |
| 7000007723 | Pcg1860-hom | 8 | 0.71034 | 0.00689 | −12.7325 |
| 7000007838 | Pcg3121-hom | 8 | 0.559 | 0.00689 | −31.3251 |
| 7000007800 | Pcg0007_119-icd | 8 | 0.83236 | 0.00689 | 2.258041 |
| 7000007823 | Pcg3121-icd | 8 | 0.83155 | 0.00689 | 2.15853 |
| 7000007777 | Pcg3381-icd | 8 | 0.82844 | 0.00689 | 1.776456 |
| 7000007708 | Pcg1860-icd | 8 | 0.82384 | 0.00689 | 1.211332 |
| 7000007662 | Pcg0007_39-icd | 12 | 0.82008 | 0.00562 | 0.749404 |
| 7000007685 | Pcg0007-icd | 8 | 0.81257 | 0.00689 | −0.17322 |
| 7000007754 | Pcg0007_265-icd | 4 | 0.81172 | 0.00974 | −0.27765 |
| 7000007698 | Pcg0007-lysA | 4 | 0.8504 | 0.00974 | 4.474311 |
| 7000007675 | Pcg0007_39-lysA | 8 | 0.84414 | 0.00689 | 3.705251 |
| 7000007836 | Pcg3121-lysA | 4 | 0.83545 | 0.00974 | 2.637657 |
| 7000007767 | Pcg0007_265-lysA | 8 | 0.83249 | 0.00689 | 2.274012 |
| 7000007813 | Pcg0007_119-lysA | 8 | 0.83096 | 0.00689 | 2.086046 |
| 7000007790 | Pcg3381-lysA | 8 | 0.8118 | 0.00689 | −0.26782 |
| 7000007676 | Pcg0007_39-lysE | 8 | 0.84394 | 0.00689 | 3.68068 |
| 7000007699 | Pcg0007-lysE | 4 | 0.83393 | 0.00974 | 2.45092 |
| 7000007768 | Pcg0007_265-lysE | 8 | 0.83338 | 0.00689 | 2.383351 |
| 7000007837 | Pcg3121-lysE | 4 | 0.83199 | 0.00974 | 2.212585 |
| 7000007791 | Pcg3381-lysE | 8 | 0.81476 | 0.00689 | 0.095825 |
| 7000007814 | Pcg0007_119-lysE | 8 | 0.81315 | 0.00689 | −0.10197 |
| 7000007775 | Pcg3381-odx | 8 | 0.82237 | 0.00689 | 1.030738 |
| 7000007752 | Pcg0007_265-odx | 8 | 0.81118 | 0.00689 | −0.34399 |
| 7000007729 | Pcg0755-odx | 8 | 0.81103 | 0.00689 | −0.36242 |
| 7000007683 | Pcg0007-odx | 8 | 0.80507 | 0.00689 | −1.09462 |
| 7000007706 | Pcg1860-odx | 4 | 0.79332 | 0.00974 | −2.53815 |
| 7000007660 | Pcg0007_39-odx | 8 | 0.79149 | 0.00689 | −2.76297 |
| 7000007798 | Pcg0007_119-odx | 8 | 0.77075 | 0.00689 | −5.31094 |
| 7000007821 | Pcg3121-odx | 4 | 0.74788 | 0.00974 | −8.12059 |
| 7000007822 | Pcg3121-pck | 8 | 0.85544 | 0.00689 | 5.093491 |
| 7000007776 | Pcg3381-pck | 8 | 0.8419 | 0.00689 | 3.43006 |
| 7000007799 | Pcg0007_119-pck | 8 | 0.83851 | 0.00689 | 3.013588 |
| 7000007753 | Pcg0007_265-pck | 8 | 0.82738 | 0.00689 | 1.646232 |
| 7000007730 | Pcg0755-pck | 4 | 0.81785 | 0.00974 | 0.475442 |
| 7000007661 | Pcg0007_39-pck | 8 | 0.80976 | 0.00689 | −0.51844 |
| 7000007684 | Pcg0007-pck | 8 | 0.79007 | 0.00689 | −2.93742 |
| 7000007707 | Pcg1860-pck | 8 | 0.71566 | 0.00689 | −12.0789 |
| 7000007840 | Pcg3121-pgi | 4 | 1.01046 | 0.00974 | 24.13819 |
| 7000007817 | Pcg0007_119-pgi | 7 | 0.99238 | 0.00736 | 21.917 |
| 7000007794 | Pcg3381-pgi | 7 | 0.99008 | 0.00736 | 21.63444 |
| 7000007771 | Pcg0007_265-pgi | 8 | 0.94665 | 0.00689 | 16.29893 |
| 7000007725 | Pcg1860-pgi | 8 | 0.85515 | 0.00689 | 5.057864 |
| 7000007702 | Pcg0007-pgi | 4 | 0.8056 | 0.00974 | −1.02951 |

TABLE 7-continued

Recombinant strains of *C. glutamicum* having modified expression of L-lysine Biosynthetic Genes

| Strain | promoter-target | N | Mean ($A_{560}$) | Std Error | % Yield Change From Base |
|---|---|---|---|---|---|
| 7000007658 | Pcg0007_39-ppc | 4 | 0.85221 | 0.00974 | 4.696676 |
| 7000007750 | Pcg0007_265-ppc | 8 | 0.84486 | 0.00689 | 3.793705 |
| 7000007727 | Pcg0755-ppc | 8 | 0.84166 | 0.00689 | 3.400575 |
| 7000007773 | Pcg3381-ppc | 4 | 0.82883 | 0.00974 | 1.824369 |
| 7000007796 | Pcg0007_119-ppc | 8 | 0.82433 | 0.00689 | 1.27153 |
| 7000007704 | Pcg1860-ppc | 8 | 0.81736 | 0.00689 | 0.415244 |
| 7000007819 | Pcg3121-ppc | 8 | 0.79898 | 0.00689 | −1.8428 |
| 7000007732 | Pcg0755-ptsG | 8 | 0.84055 | 0.00689 | 3.264208 |
| 7000007709 | Pcg1860-ptsG | 8 | 0.81075 | 0.00689 | −0.39682 |
| 7000007663 | Pcg0007_39-ptsG | 8 | 0.80065 | 0.00689 | −1.63763 |
| 7000007778 | Pcg3381-ptsG | 8 | 0.23419 | 0.00689 | −71.229 |
| 7000007801 | Pcg0007_119-ptsG | 8 | 0.17295 | 0.00689 | −78.7525 |
| 7000007824 | Pcg3121-ptsG | 8 | 0.16035 | 0.00689 | −80.3005 |
| 7000007705 | Pcg1860-pyc | 8 | 0.85143 | 0.00689 | 4.60085 |
| 7000007728 | Pcg0755-pyc | 8 | 0.79803 | 0.00689 | −1.95951 |
| 7000007659 | Pcg0007_39-pyc | 8 | 0.75539 | 0.00689 | −7.19797 |
| 7000007751 | Pcg0007_265-pyc | 8 | 0.73664 | 0.00689 | −9.50146 |
| 7000007682 | Pcg0007-pyc | 4 | 0.73142 | 0.00974 | −10.1428 |
| 7000007774 | Pcg3381-pyc | 4 | 0.66667 | 0.00974 | −18.0975 |
| 7000007797 | Pcg0007_119-pyc | 4 | 0.52498 | 0.00974 | −35.5046 |
| 7000007820 | Pcg3121-pyc | 8 | 0.52235 | 0.00689 | −35.8277 |
| 7000007841 | Pcg3121-tkt | 8 | 0.82565 | 0.00689 | 1.433696 |
| 7000007818 | Pcg0007_119-tkt | 8 | 0.81674 | 0.00689 | 0.339075 |
| 7000007749 | Pcg0755-tkt | 8 | 0.81496 | 0.00689 | 0.120396 |
| 7000007703 | Pcg0007-tkt | 4 | 0.76763 | 0.00974 | −5.69424 |
| 7000007795 | Pcg3381-tkt | 8 | 0.72213 | 0.00689 | −11.2841 |
| 7000007772 | Pcg0007_265-tkt | 8 | 0.68884 | 0.00689 | −15.3738 |
| 7000007701 | Pcg0007-zwf | 4 | 0.95061 | 0.00974 | 16.78542 |
| 7000007747 | Pcg0755-zwf | 8 | 0.92595 | 0.00689 | 13.75587 |
| 7000007770 | Pcg0007_265-zwf | 8 | 0.9029 | 0.00689 | 10.9241 |
| 7000007724 | Pcg1860-zwf | 8 | 0.79309 | 0.00689 | −2.5664 |
| 7000007839 | Pcg3121-zwf | 4 | 0.13379 | 0.00974 | −83.5635 |

Example 4: Engineering the L-Lysine Biosynthetic Pathway

The yield of L-lysine is modified by swapping pairs of promoters for target genes as provided in Table 8. The constructs of Example 3 are used to prepare recombinant organisms as provided in Table 8. As shown, the combination of Pcg0007-lysA and Pcg3121-pgi provide for the highest yields of L-lysine.

TABLE 8

Paired Promoter Swapping of Target Genes in the L-lysine biosynthetic pathway

| Strain ID | Number | PRO Swap 1 | PRO Swap 2 | Mean Yield ($A_{560}$) | Std Dev |
|---|---|---|---|---|---|
| 7000008489 | 4 | Pcg0007-lysA | Pcg3121-pgi | 1.17333 | 0.020121 |
| 7000008530 | 8 | Pcg1860-pyc | Pcg0007-zwf | 1.13144 | 0.030023 |
| 7000008491 | 7 | Pcg0007-lysA | Pcg0007-zwf | 1.09836 | 0.028609 |
| 7000008504 | 8 | Pcg3121-pck | Pcg0007-zwf | 1.09832 | 0.021939 |
| 7000008517 | 8 | Pcg0007_39-ppc | Pcg0007-zwf | 1.09502 | 0.030777 |
| 7000008502 | 4 | Pcg3121-pck | Pcg3121-pgi | 1.09366 | 0.075854 |
| 7000008478 | 4 | Pcg3381-ddh | Pcg0007-zwf | 1.08893 | 0.025505 |
| 7000008465 | 4 | Pcg0007_265-dapB | Pcg0007-zwf | 1.08617 | 0.025231 |
| 7000008535 | 8 | Pcg0007-zwf | Pcg3121-pgi | 1.06261 | 0.019757 |
| 7000008476 | 6 | Pcg3381-ddh | Pcg3121-pgi | 1.04808 | 0.084307 |
| 7000008510 | 8 | Pcg3121-pgi | Pcg1860-pyc | 1.04112 | 0.021087 |
| 7000008525 | 8 | Pcg1860-pyc | Pcg0007_265-dapB | 1.0319 | 0.034045 |
| 7000008527 | 8 | Pcg1860-pyc | Pcg0007-lysA | 1.02278 | 0.043549 |
| 7000008452 | 5 | Pcg1860-asd | Pcg0007-zwf | 1.02029 | 0.051663 |
| 7000008463 | 4 | Pcg0007_265-dapB | Pcg3121-pgi | 1.00511 | 0.031604 |

TABLE 8-continued

Paired Promoter Swapping of Target Genes in the L-lysine biosynthetic pathway

| Strain ID | Number | PRO Swap 1 | PRO Swap 2 | Mean Yield ($A_{560}$) | Std Dev |
|---|---|---|---|---|---|
| 7000008524 | 8 | Pcg1860-pyc | Pcg1860-asd | 1.00092 | 0.026355 |
| 7000008458 | 4 | Pcg3381-aspB | Pcg1860-pyc | 1.00043 | 0.020083 |
| 7000008484 | 8 | Pcg3381-fbp | Pcg1860-pyc | 0.99686 | 0.061364 |
| 7000008474 | 8 | Pcg3381-ddh | Pcg3381-fbp | 0.99628 | 0.019733 |
| 7000008522 | 8 | Pcg0755-ptsG | Pcg3121-pgi | 0.99298 | 0.066021 |
| 7000008528 | 8 | Pcg1860-pyc | Pcg3121-pck | 0.99129 | 0.021561 |
| 7000008450 | 4 | Pcg1860-asd | Pcg3121-pgi | 0.98262 | 0.003107 |
| 7000008448 | 8 | Pcg1860-asd | Pcg3381-fbp | 0.97814 | 0.022285 |
| 7000008494 | 8 | Pcg0007_39-lysE | Pcg3381-fbp | 0.97407 | 0.027018 |
| 7000008481 | 8 | Pcg3381-fbp | Pcg0007-lysA | 0.9694 | 0.029315 |
| 7000008497 | 8 | Pcg0007_39-lysA | Pcg1860-pyc | 0.9678 | 0.028569 |
| 7000008507 | 8 | Pcg3121-pgi | Pcg3381-fbp | 0.96358 | 0.035078 |
| 7000008501 | 8 | Pcg3121-pck | Pcg0007-lysA | 0.96144 | 0.018665 |
| 7000008486 | 8 | Pcg0007-lysA | Pcg0007_265-dapB | 0.94523 | 0.017578 |
| 7000008459 | 8 | Pcg0007_265-dapB | Pcg1860-asd | 0.94462 | 0.023847 |
| 7000008506 | 2 | Pcg3121-pgi | Pcg0007_265-dapD | 0.94345 | 0.014014 |
| 7000008487 | 8 | Pcg0007-lysA | Pcg3381-ddh | 0.94249 | 0.009684 |
| 7000008498 | 8 | Pcg3121-pck | Pcg1860-asd | 0.94154 | 0.016802 |
| 7000008485 | 8 | Pcg0007-lysA | Pcg1860-asd | 0.94135 | 0.013578 |
| 7000008499 | 8 | Pcg3121-pck | Pcg0007_265-dapB | 0.93805 | 0.013317 |
| 7000008472 | 8 | Pcg3381-ddh | Pcg1860-asd | 0.93716 | 0.012472 |
| 7000008511 | 8 | Pcg0007_39-ppc | Pcg1860-asd | 0.93673 | 0.015697 |
| 7000008514 | 8 | Pcg0007_39-ppc | Pcg0007-lysA | 0.93668 | 0.027204 |
| 7000008473 | 8 | Pcg3381-ddh | Pcg0007_265-dapB | 0.93582 | 0.030377 |
| 7000008461 | 7 | Pcg0007_265-dapB | Pcg3381-fbp | 0.93498 | 0.037862 |
| 7000008512 | 8 | Pcg0007_39-ppc | Pcg0007_265-dapB | 0.93033 | 0.017521 |
| 7000008456 | 8 | Pcg3381-aspB | Pcg3121-pck | 0.92544 | 0.020075 |
| 7000008460 | 8 | Pcg0007_265-dapB | Pcg0007_265-dapD | 0.91723 | 0.009508 |
| 7000008492 | 8 | Pcg0007_39-lysE | Pcg3381-aspB | 0.91165 | 0.012988 |
| 7000008493 | 8 | Pcg0007_39-lysE | Pcg0007_265-dapD | 0.90609 | 0.031968 |
| 7000008453 | 8 | Pcg3381-aspB | Pcg0007_265-dapB | 0.90338 | 0.013228 |
| 7000008447 | 8 | Pcg1860-asd | Pcg0007_265-dapD | 0.89886 | 0.028896 |
| 7000008455 | 8 | Pcg3381-aspB | Pcg0007-lysA | 0.89531 | 0.027108 |
| 7000008454 | 6 | Pcg3381-aspB | Pcg3381-ddh | 0.87816 | 0.025807 |
| 7000008523 | 8 | Pcg0755-ptsG | Pcg1860-pyc | 0.87693 | 0.030322 |
| 7000008520 | 8 | Pcg0755-ptsG | Pcg3381-fbp | 0.87656 | 0.018452 |
| 7000008533 | 4 | Pcg0007-zwf | Pcg3381-fbp | 0.84584 | 0.017012 |
| 7000008519 | 8 | Pcg0755-ptsG | Pcg0007_265-dapD | 0.84196 | 0.025747 |

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments described herein have been described herein for purposes of illustration, various modifications may be made without deviating from the spirit and scope described herein. Accordingly, the disclosure is not limited except as by the appended claims.

What is claimed is:

1. A promoter ladder comprising at least three promoter polynucleotide sequences selected from the group consisting of SEQ ID NOs: 1-8, wherein said promoter ladder comprises a plurality of promoters with incrementally increasing levels of promoter activity.

2. The promoter ladder according to claim 1, wherein at least one of said promoter polynucleotide sequences is selected from the group consisting of SEQ ID NOs: 1, 5 and 7.

3. The promotor ladder according to claim 1, wherein at least one of said promoter polynucleotide sequences is selected from the group consisting of SEQ ID NOs: 1-2.

4. The promoter ladder according to claim 1, wherein at least one of said promoter polynucleotide sequences is selected from the group consisting of SEQ ID NOs: 3, 4 and 5.

5. The promotor ladder according to claim 1, wherein at least one of said promoter polynucleotide sequences is selected from the group consisting of SEQ ID NOs: 6-8.

6. The promoter ladder according to claim 1, wherein each promoter of said promoter ladder is functionally linked to at least one heterologous target gene.

7. The promotor ladder according to claim 6, wherein said at least one heterologous target gene is a gene that is a component of a biosynthetic pathway producing a biomolecule selected from the group consisting of amino acids, organic acids, proteins and polymers.

8. The promoter ladder accordingly to claim 7, wherein said at least one heterologous target gene is a gene that is selected from the group consisting of: aspartate-semialdehyde dehydrogenase, 4-hydroxy-tetrahydrodipicolinate synthase, dihydrodipicolinate reductase, 2,3,4,5-tetrahydropyridine-2-carboxylate N-succinyltransferase, N-succinyldiaminopimelate aminotransferase, succinyl-diaminopimelate desuccinylase, diaminopimelate epimerase, diaminopimelate decarboxylase, diaminopimelate dehydrogenase, aspartokinase lysc alpha and beta subunits, aspartate aminotransferase, glucose-specific enzyme II BC component of phosphotransferase System (PTS), glucose-6-phosphate 1-dehydrogenase, glucose-6-phosphate isomerase, transketolase, 6-phosphofructokinase 1, phosphoenolpyruvate carboxylase, pyruvate carboxylase, isocitrate dehydrogenase, phosphoenolpyruvate carboxykinase (GTP), oxaloacetate decarboxylase, homoserine kinase, homoserine dehydrogenase, and threonine synthase.

9. A recombinant polynucleotide comprising the promoter ladder of claim 1 functionally linked to a heterologous target gene.

10. A plurality of recombinant polynucleotides comprising the promoter ladder of claim 1, wherein each recombinant polynucleotide comprises one promoter from the promoter ladder functionally linked to a heterologous target gene.

11. A plurality if recombinant vectors comprising the promoter ladder of claim 1, the recombinant polynucleotide of claim 9, or the plurality of recombinant polynucleotides of claim 10.

12. A plurality of recombinant vectors comprising the promoter ladder of claim 1, the recombinant polynucleotide of claim 9, or the plurality of recombinant polynucleotides of claim 10.

13. The plurality of host cells according to claim 12, wherein the host cells belong to the genus *Corynebacterium*.

14. A plurality of transformed host cells comprising a combination of at least three promoter polynucleotide sequences selected from the group consisting of SEQ ID NOs: 1-8 each functionally linked to at least one heterologous target gene, wherein said combination of promoter polynucleotide sequences comprises a plurality of promoters with incrementally increasing levels of promoter activity.

15. The plurality of transformed host cells according to claim 14, wherein said target gene is associated with a biosynthetic pathway producing a biomolecule selected from: amino acids, organic acids, flavors and fragrances, biofuels, proteins and enzymes, polymers/monomers and other biomaterials, lipids, nucleic acids, small molecule therapeutics, protein therapeutics, fine chemicals, and nutraceuticals.

16. The plurality of transformed host cells according to claim 14, wherein said target gene is associated with a biosynthetic pathway producing a secondary metabolite selected from: antibiotics, alkaloids, terpenoids, and polyketides.

17. The plurality of transformed host cells according to claim 14, wherein each promoter polynucleotide sequence is functionally linked to a different heterologous target gene.

18. The plurality of transformed host cells according to claim 14, wherein two or more promoter polynucleotide sequences are functionally linked to at least one heterologous target gene.

19. The plurality of transformed host cells according to claim 18, wherein the two or more promoter polynucleotide sequences are the same.

20. The plurality of transformed host cells according to claim 18, wherein the two or more promoter polynucleotide sequences are different.

* * * * *

UNITED STATES PATENT AND TRADEMARK OFFICE
CERTIFICATE OF CORRECTION

| | | |
|---|---|---|
| PATENT NO. | : 11,293,029 B2 | Page 1 of 1 |
| APPLICATION NO. | : 16/060375 | |
| DATED | : April 5, 2022 | |
| INVENTOR(S) | : Zachariah Serber et al. | |

It is certified that error appears in the above-identified patent and that said Letters Patent is hereby corrected as shown below:

In the Claims

Column 69, Claim 3, Line 11:
"promotor"
Should read:
-- promoter --

Column 69, Claim 5, Line 18:
"promotor"
Should read:
-- promoter --

Column 69, Claim 7, Line 24:
"promotor"
Should read:
-- promoter --

Column 70, Claim 11, Line 6:
"plurality if recombinant"
Should read:
-- plurality of recombinant --

Signed and Sealed this
Fourteenth Day of June, 2022

Katherine Kelly Vidal
*Director of the United States Patent and Trademark Office*

SEQUENCE LISTING

<160> NUMBER OF SEQ ID NOS: 16

<210> SEQ ID NO 1
<211> LENGTH: 97
<212> TYPE: DNA
<213> ORGANISM: Corynebacterium glutamicum
<220> FEATURE:
<221> NAME/KEY: source
<223> OTHER INFORMATION: /note="Pcg0007_39"

<400> SEQUENCE: 1
tgccgtttct cgcgttgtgt gtggtactac gtggggacct aagcgtgtat tatggaaacg  60
tctgtatcgg ataagtagcg aggagtgttc gttaaaa  97

<210> SEQ ID NO 2
<211> LENGTH: 97
<212> TYPE: DNA
<213> ORGANISM: Corynebacterium glutamicum
<220> FEATURE:
<221> NAME/KEY: source
<223> OTHER INFORMATION: /note="Pcg0007"

<400> SEQUENCE: 2
tgccgtttct cgcgttgtgt gtggtactac gtggggacct aagcgtgtaa gatggaaacg  60
tctgtatcgg ataagtagcg aggagtgttc gttaaaa  97

<210> SEQ ID NO 3
<211> LENGTH: 93
<212> TYPE: DNA
<213> ORGANISM: Corynebacterium glutamicum
<220> FEATURE:
<221> NAME/KEY: source
<223> OTHER INFORMATION: /note="Pcg1860"

<400> SEQUENCE: 3
cttagctttg acctgcacaa atagttgcaa attgtcccac atacacataa agtagcttgc  60
gtatttaaaa ttatgaacct aaggggttta gca  93

<210> SEQ ID NO 4
<211> LENGTH: 98
<212> TYPE: DNA
<213> ORGANISM: Corynebacterium glutamicum
<220> FEATURE:
<221> NAME/KEY: source
<223> OTHER INFORMATION: /note="Pcg0755"

<400> SEQUENCE: 4
aataaattta taccacacag tctattgcaa tagaccaagc tgttcagtag ggtgcatggg  60
agaagaattt cctaataaaa actcttaagg acctccaa  98

<210> SEQ ID NO 5
<211> LENGTH: 97
<212> TYPE: DNA
<213> ORGANISM: Corynebacterium glutamicum
<220> FEATURE:
<221> NAME/KEY: source
<223> OTHER INFORMATION: /note="Pcg0007_265"

<400> SEQUENCE: 5
tgccgtttct cgcgttgtgt gtggtactac gtggggacct aagcgtgtac gctggaaacg  60
tctgtatcgg ataagtagcg aggagtgttc gttaaaa  97

<210> SEQ ID NO 6
<211> LENGTH: 86
<212> TYPE: DNA
<213> ORGANISM: Corynebacterium glutamicum
<220> FEATURE:
<221> NAME/KEY: source
<223> OTHER INFORMATION: /note="Pcg3381"

<400> SEQUENCE: 6
cgccggataa atgaattgat tattttaggc tcccagggat taagtctagg gtggaatgca    60
gaaatatttc ctacggaagg tccgtt                                         86

<210> SEQ ID NO 7
<211> LENGTH: 97
<212> TYPE: DNA
<213> ORGANISM: Corynebacterium glutamicum
<220> FEATURE:
<221> NAME/KEY: source
<223> OTHER INFORMATION: /note="Pcg0007_119"

<400> SEQUENCE: 7
tgccgtttct cgcgttgtgt gtggtactac gtggggacct aagcgtgttg catggaaacg    60
tctgtatcgg ataagtagcg aggagtgttc gttaaaa                             97

<210> SEQ ID NO 8
<211> LENGTH: 87
<212> TYPE: DNA
<213> ORGANISM: Corynebacterium glutamicum
<220> FEATURE:
<221> NAME/KEY: source
<223> OTHER INFORMATION: /note="Pcg3121"

<400> SEQUENCE: 8
gtggctaaaa cttttggaaa cttaagttac ctttaatcgg aaacttattg aattcgggtg    60
aggcaactgc aactctggac ttaaagc                                        87

<210> SEQ ID NO 9
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 9
tcatgaccaa aatcccttaa cgtg                                           24

<210> SEQ ID NO 10
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 10
gcgtactctt cgatggtgaa aacatctc                                       28

<210> SEQ ID NO 11
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 11
gacctaaaat gtgtaaaggg caaagtgtat acaacaacaa gacccatcat agtttgc       57

<210> SEQ ID NO 12
<211> LENGTH: 44

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
cacgttaagg gattttggtc atgacacatg cagtcatgtc gtgc                    44

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
gcttgcatgc ctgcaggtcg a                                             21

<210> SEQ ID NO 14
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
atggtgagca agggcgagga gc                                            22

<210> SEQ ID NO 15
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
ggaaacgtct gtatcggata agtag                                         25

<210> SEQ ID NO 16
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (27)..(30)
<223> OTHER INFORMATION: a, c, t, g, unknown or other

<400> SEQUENCE: 16
ctacttatcc gatacagacg tttccannnn acacgcttag gtccccacgt agtacca      57
```